US010820920B2

(12) United States Patent
Scoggins et al.

(10) Patent No.: US 10,820,920 B2
(45) Date of Patent: Nov. 3, 2020

(54) REUSABLE ULTRASONIC MEDICAL DEVICES AND METHODS OF THEIR USE

(71) Applicant: Ethicon LLC, Guaynabo, PR (US)

(72) Inventors: Patrick J. Scoggins, Loveland, OH (US); Tylor C. Muhlenkamp, Cincinnati, OH (US); David C. Groene, Cincinnati, OH (US); William D. Dannaher, Cincinnati, OH (US); Benjamin D. Dickerson, Cincinnati, OH (US); Phillip H. Clauda, Cincinnati, OH (US); Rafael J. Ruiz Ortiz, Mason, OH (US); Matthew C. Miller, Cincinnati, OH (US); Kevin A. Bash, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 342 days.

(21) Appl. No.: 15/641,858

(22) Filed: Jul. 5, 2017

(65) Prior Publication Data
US 2019/0008543 A1 Jan. 10, 2019

(51) Int. Cl.
*A61B 17/32* (2006.01)
*A61B 17/295* (2006.01)
(Continued)

(52) U.S. Cl.
CPC .... *A61B 17/320068* (2013.01); *A61B 17/295* (2013.01); *A61B 17/320092* (2013.01);
(Continued)

(58) Field of Classification Search
CPC .......... A61B 17/295; A61B 17/320068; A61B 17/320092; A61B 2017/00017;
(Continued)

(56) References Cited

U.S. PATENT DOCUMENTS 969,528 A 9/1910 Disbrow
1,570,025 A 1/1926 Young
(Continued)

FOREIGN PATENT DOCUMENTS

CA 2535467 A1 4/1993
CA 2214413 A1 9/1996
(Continued)

OTHER PUBLICATIONS

Campbell et al, "Thermal Imaging in Surgery," p. 19-3, in Medical Infrared Imaging, N. A. Diakides and J. D. Bronzino, Eds. (2008).
(Continued)

*Primary Examiner* — Mohamed G Gabr

(57) ABSTRACT

A variety of methods for managing a re-usable ultrasonic medical device may include a medical device control module capable of receiving functional data from a user assembled or reassembled ultrasonic medical device, and notifying the user if a value of the functional data lies within an acceptance range. If the value of the functional data does not lie within the acceptance range, the control module may prompt a user to reassemble the device or to clean or replace one or more components thereof. The functional data may relate to a clamp force of a jaw assembly, an impedance or resonant frequency value of an ultrasonic blade, or a mechanical displacement value of one or more moving components of the device.

26 Claims, 25 Drawing Sheets

(51) Int. Cl.
*A61B 90/00* (2016.01)
*A61B 17/00* (2006.01)
*A61B 17/29* (2006.01)

(52) U.S. Cl.
CPC ...... *A61B 90/08* (2016.02); *A61B 2017/0003* (2013.01); *A61B 2017/0011* (2013.01); *A61B 2017/00017* (2013.01); *A61B 2017/00039* (2013.01); *A61B 2017/0046* (2013.01); *A61B 2017/00119* (2013.01); *A61B 2017/00725* (2013.01); *A61B 2017/2925* (2013.01); *A61B 2017/320071* (2017.08); *A61B 2017/320075* (2017.08); *A61B 2017/320093* (2017.08); *A61B 2017/320094* (2017.08); *A61B 2090/064* (2016.02); *A61B 2090/081* (2016.02); *A61B 2090/0808* (2016.02); *A61B 2090/0809* (2016.02); *A61B 2090/0811* (2016.02); *A61B 2090/0812* (2016.02); *A61B 2090/0814* (2016.02)

(58) Field of Classification Search
CPC .. A61B 2017/0003; A61B 2017/00039; A61B 2017/0011; A61B 2017/00119; A61B 2017/0046; A61B 2017/00725; A61B 2017/2925; A61B 2017/320071; A61B 2017/320075; A61B 2017/320093; A61B 2017/320094; A61B 2090/064; A61B 2090/0808; A61B 2090/0809; A61B 2090/081; A61B 2090/0811; A61B 2090/0812; A61B 2090/0814; A61B 90/09

See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,503,396 A | 3/1970 | Pierie et al. |
| 3,503,397 A | 3/1970 | Fogarty et al. |
| 3,503,398 A | 3/1970 | Fogarty et al. |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,832,776 A | 9/1974 | Sawyer |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,173,725 A | 11/1979 | Asai et al. |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,663,677 A | 5/1987 | Griffith et al. |
| 4,674,502 A | 6/1987 | Imonti |
| 4,708,127 A | 11/1987 | Abdelghani |
| 4,712,722 A | 12/1987 | Hood et al. |

(56) References Cited

U.S. PATENT DOCUMENTS

| | | |
|---|---|---|
| 4,735,603 A | 4/1988 | Goodson et al. |
| 4,750,488 A | 6/1988 | Wuchinich et al. |
| 4,761,871 A | 8/1988 | O'Connor et al. |
| 4,808,154 A | 2/1989 | Freeman |
| 4,819,635 A | 4/1989 | Shapiro |
| 4,821,719 A | 4/1989 | Fogarty |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,061,269 A | 10/1991 | Muller |
| 5,084,052 A | 1/1992 | Jacobs |
| 5,088,687 A | 2/1992 | Stender |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,354,265 A | 10/1994 | Mackool |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |

(56) References Cited

U.S. PATENT DOCUMENTS

| | | |
|---|---|---|
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |

(56) References Cited

U.S. PATENT DOCUMENTS

| | | |
|---|---|---|
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,007,552 A | 12/1999 | Fogarty et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |

(56) References Cited

U.S. PATENT DOCUMENTS

| | | |
|---|---|---|
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,902 B1 | 8/2001 | Fogarty et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,299,621 B1 | 10/2001 | Fogarty et al. |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,333,488 B1 | 12/2001 | Lawrence et al. |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,387,112 B1 | 5/2002 | Fogarty et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,425,907 B1 | 7/2002 | Shibata et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,286 B2 | 10/2002 | Mastri et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,883 B2 | 11/2003 | Francischelli et al. |

(56) References Cited

U.S. PATENT DOCUMENTS

| | | |
|---|---|---|
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |

(56) References Cited

U.S. PATENT DOCUMENTS

| | | |
|---|---|---|
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |

(56) References Cited

U.S. PATENT DOCUMENTS

| | | |
|---|---|---|
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |

(56) References Cited

U.S. PATENT DOCUMENTS

| | | |
|---|---|---|
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |

(56) References Cited

U.S. PATENT DOCUMENTS

| | | |
|---|---|---|
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,659,208 B1 | 2/2014 | Rose et al. |

(56) References Cited

U.S. PATENT DOCUMENTS

| | | |
|---|---|---|
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |

(56) References Cited

U.S. PATENT DOCUMENTS

| | | |
|---|---|---|
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |

(56) References Cited

U.S. PATENT DOCUMENTS

| | | |
|---|---|---|
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,368,892 B2 | 8/2019 | Stulen et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |

(56) References Cited

U.S. PATENT DOCUMENTS

| | | |
|---|---|---|
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |

(56) References Cited

U.S. PATENT DOCUMENTS

| | | |
|---|---|---|
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0324998 A1* | 12/2013 | Kimball ............ A61B 17/32009 606/41 |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |

(56) References Cited

U.S. PATENT DOCUMENTS

| | | |
|---|---|---|
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0257780 A1 | 9/2015 | Houser |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0114355 A1 | 4/2016 | Sakai et al. |
| 2016/0121143 A1 | 5/2016 | Mumaw et al. |
| 2016/0128769 A1 | 5/2016 | Rontal et al. |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0346001 A1 | 12/2016 | Vakharia et al. |
| 2016/0367281 A1 | 12/2016 | Gee et al. |
| 2016/0374709 A1 | 12/2016 | Timm et al. |
| 2017/0000541 A1 | 1/2017 | Yates et al. |
| 2017/0014152 A1 | 1/2017 | Noui et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0172608 A1* | 6/2017 | Madan ............. A61B 17/32009 |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014848 A1 | 1/2018 | Messerly et al. |
| 2018/0049767 A1 | 2/2018 | Gee et al. |
| 2018/0055529 A1 | 3/2018 | Messerly et al. |
| 2018/0055531 A1 | 3/2018 | Messerly et al. |
| 2018/0055532 A1 | 3/2018 | Messerly et al. |
| 2018/0055533 A1 | 3/2018 | Conlon et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0125523 A1 | 5/2018 | Johnson |
| 2018/0146975 A1 | 5/2018 | Zhang |
| 2018/0168680 A1 | 6/2018 | Houser et al. |
| 2018/0177521 A1 | 6/2018 | Faller et al. |
| 2018/0199957 A1 | 7/2018 | Robertson et al. |
| 2018/0206881 A1 | 7/2018 | Price et al. |
| 2018/0221049 A1 | 8/2018 | Faller et al. |
| 2019/0053822 A1 | 2/2019 | Robertson et al. |
| 2019/0090900 A1 | 3/2019 | Rhee et al. |
| 2019/0133633 A1 | 5/2019 | Neurohr et al. |
| 2019/0239919 A1 | 8/2019 | Witt et al. |
| 2019/0262029 A1 | 8/2019 | Messerly et al. |

FOREIGN PATENT DOCUMENTS

| | | |
|---|---|---|
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 202027624 U | 11/2011 |
| CN | 102335778 A | 2/2012 |
| CN | 103668171 A | 3/2014 |
| CN | 103921215 A | 7/2014 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2964554 A1 | 3/2012 |
| GB | 2032221 A | 4/1980 |
| GB | 2317566 A | 4/1998 |
| GB | 2318298 A | 4/1998 |
| GB | 2425480 A | 11/2006 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |

(56) References Cited

FOREIGN PATENT DOCUMENTS

| | | |
|---|---|---|
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210299 A | 8/2000 |
| JP | 2000271145 A | 10/2000 |
| JP | 2000287987 A | 10/2000 |
| JP | 2000312682 A | 11/2000 |
| JP | 2001029353 A | 2/2001 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | D1339835 S | 8/2008 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0195810 A2 | 12/2001 |
| WO | WO-02080799 A1 | 10/2002 |
| WO | WO-2004037095 A2 | 5/2004 |
| WO | WO-2004078051 A2 | 9/2004 |
| WO | WO-2004098426 A1 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |
| WO | WO-2012044606 A2 | 4/2012 |
| WO | WO-2012066983 A1 | 5/2012 |
| WO | WO-2013048963 A2 | 4/2013 |

OTHER PUBLICATIONS

F. A. Duck, "Optical Properties of Tissue Including Ultraviolet and Infrared Radiation," pp. 43-71 in Physical Properties of Tissue (1990).

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Sullivan, "Optimal Choice for Number of Strands in a Litz-Wire Transformer Winding," IEEE Transactions on Power Electronics, vol. 14, No. 2, Mar. 1999, pp. 283-291.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

Walsh, S. J., White, R. G., "Vibrational Power Transmission in Curved Beams," Journal of Sound and Vibration, 233(3), 455-488 (2000).

http://www.apicalinstr.com/generators.htm.

http://www.dotmed.com/listing/electrosurical-unit/ethicon/ultracision-g110-/1466724.

http:/www.ethicon.com/gb-en/healthcare-professionals/products/energy-devices/capital//ge . . . .

http://www.medicalexpo.com/medical-manufacturer/electrosurgical-generator-6951.html.

http://www.megadyne.com/es_generator.php.

http://www.valleylab.com/product/es/generators/index.html.

Covidien 501(k) Summary Sonicision, dated Feb. 24, 2011 (7 pages).

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Fowler, K.R., "A Programmable, Arbitrary Waveform Electrosurgical Device," IEEE Engineering in Medicine and Biology Society 10th Annual International Conference, pp. 1324, 1325 (1988).

LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

(56) References Cited

OTHER PUBLICATIONS

Gerhard, Glen C., "Surgical Electrotechnology: Quo Vadis?," IEEE Transactions on Biomedical Engineering, vol. BME-31, No. 12, pp. 787-792, Dec. 1984.
http://www.4-traders.com/JOHNSON-JOHNSON-4832/news/Johnson-Johnson-Ethicon-E . . . .
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

\* cited by examiner

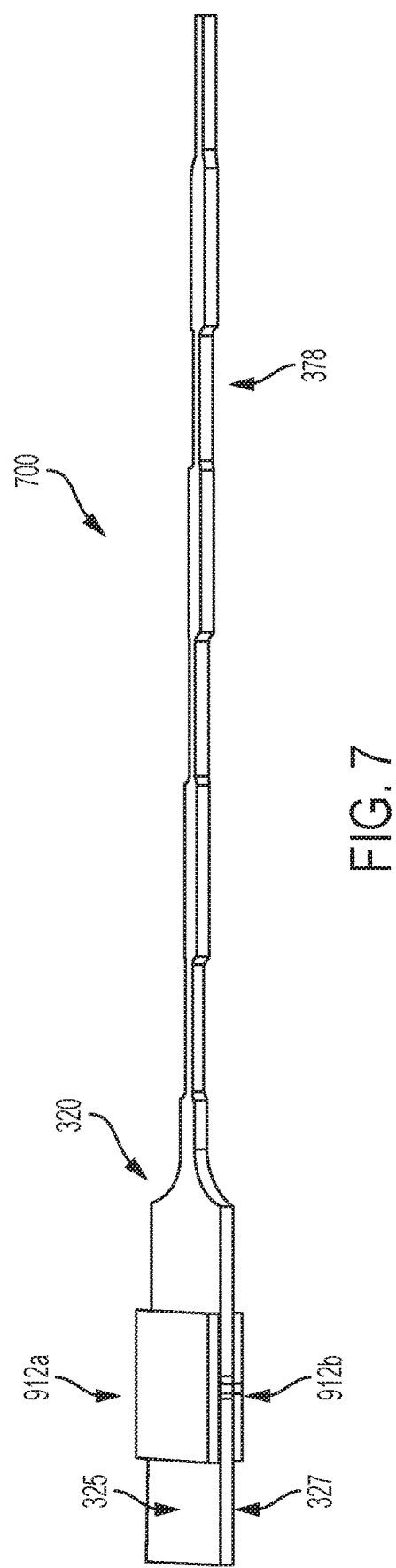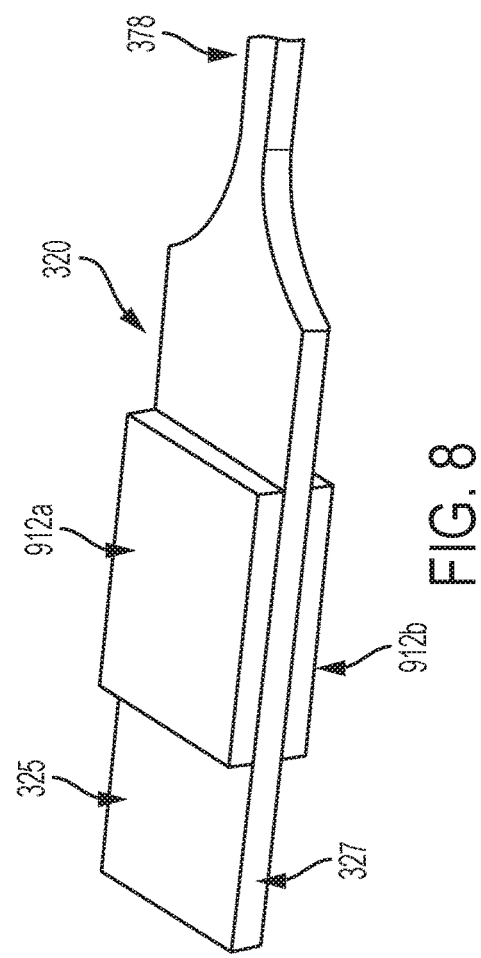
FIG. 7
FIG. 8

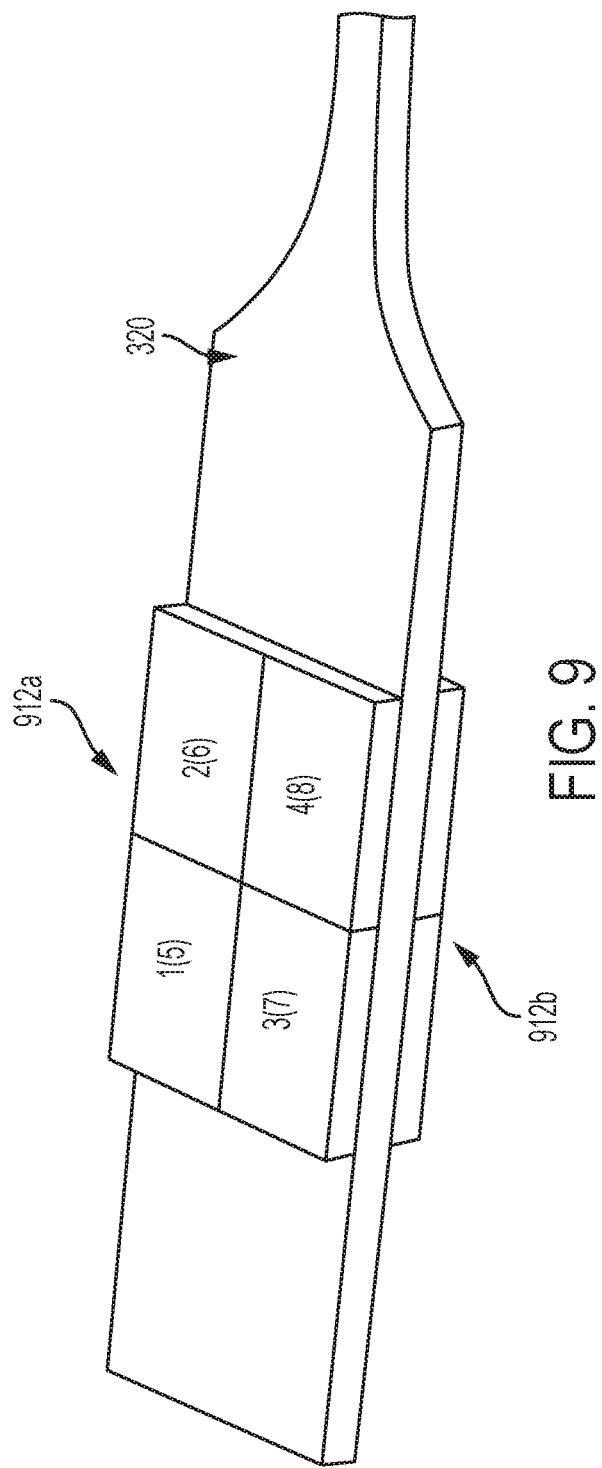

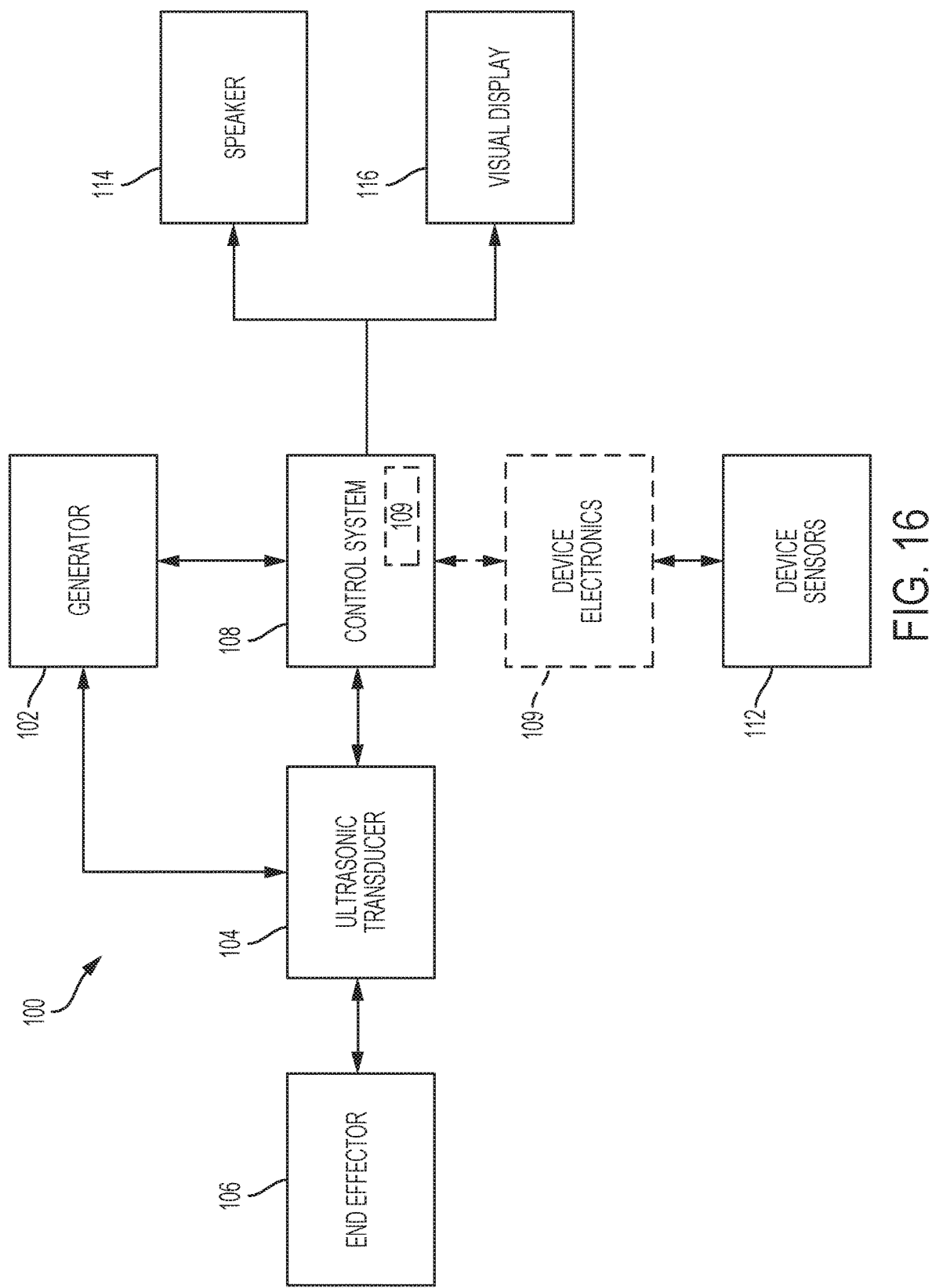

REUSABLE ULTRASONIC MEDICAL DEVICES AND METHODS OF THEIR USE

BACKGROUND

Ultrasonic surgical devices are finding increasingly widespread applications in surgical procedures by virtue of their unique performance characteristics. Depending upon specific device configurations and operational parameters, ultrasonic surgical devices can provide substantially simultaneous transection of tissue and hemostasis by coagulation, desirably minimizing patient trauma. An ultrasonic surgical device may comprise a handpiece containing an ultrasonic transducer, and an instrument coupled to the ultrasonic transducer having a distally mounted end effector (e.g., a blade tip and clamp arm) to cut and seal tissue. In some cases, the instrument may be permanently affixed to the handpiece. In other cases, the instrument may be detachable from the handpiece, as in the case of a reusable instrument or an instrument that is interchangeable between different handpieces. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electro surgical procedures. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a hemostatic seal. A surgeon can control the cutting speed and coagulation by the force applied to the tissue by the end effector, the time over which the force is applied and the selected excursion level of the end effector.

It may be recognized that portions of an ultrasonic medical device may be contaminated with tissue and other medical debris during use, and therefore the device, or portions of the device, must be cleaned and sterilized prior to use on each patient. Further, the vibrational energy imparted to components of an ultrasonic medical device may result in component wear or failure including, for example, breakage of the ultrasonic blade. As a result, over time and use, some components of the ultrasonic medical device should be replaced or repaired before the device may be reused. To some extent, the device may be disassembled in order to effect component cleaning, replacement, or repair.

Device cleaning, repair, or part replacement may be performed by the manufacturer or by a third party authorized by the manufacturer, but such a process may remove the device from use for an unacceptable period of time. Thus, an ultrasonic medical device configured for cleaning, repair, or part replacement by the end user would be preferable to one requiring servicing at a separate facility. However, it may be further recognized that an end user may not have the skill to assure that a reassembled cleaned, repaired, or refurbished medical device is in an acceptable state for reuse after reassembly. Therefore, it is desirable to incorporate features within the reusable ultrasonic medical device to assure that a user may be able to successfully reassemble the device after cleaning, repair, or part replacement.

BRIEF SUMMARY

In one aspect, a method of managing a re-usable ultrasonic medical device, includes receiving, by an ultrasonic medical device control module, an electrical connection from an ultrasonic medical device reassembled by a user, prompting, by the ultrasonic medical device control module, the user to operate a jaw control component configured to close a jaw of an end effector of the re-assembled ultrasonic medical device, receiving, by the ultrasonic medical device control module, closure data from a closure sensor disposed within the ultrasonic medical device indicating that the jaw of the end effector is in a closed configuration, receiving, by the ultrasonic medical device control module, functional data from the ultrasonic medical device referencing a functional state of at least one component of the re-assembled ultrasonic medical device, comparing, by the ultrasonic medical device control module, a value of the functional data with one or more predetermined acceptance reference values, and providing, by the ultrasonic medical device control module, to the user an acceptability indication based on the comparison of the value of the functional data and the one or more predetermined acceptance reference values.

In an aspect of the method, receiving an electrical connection from an ultrasonic medical device reassembled by a user includes receiving an electrical connection from an ultrasonic medical device having at least one component re-cleaned or re-sterilized by the user.

In an aspect of the method, receiving an electrical connection from an ultrasonic medical device reassembled by a user includes receiving an electrical connection from an ultrasonic medical device having at least one repaired component.

In an aspect of the method, receiving an electrical connection from an ultrasonic medical device reassembled by a user includes receiving an electrical connection from an ultrasonic medical device having at least one replaced component.

An aspect of the method further includes determining, by the ultrasonic medical device control module, that the value of the functional data is within the acceptance range, and providing to the user an acceptability indication based on the comparison of the value of the functional data and the one or more predetermined acceptance reference values includes providing to the user an indication of device acceptability for medical use.

An aspect of the method further includes determining, by the ultrasonic medical device control module, that the value of the functional data is not within the acceptance range, and providing to the user an acceptability indication based on the comparison of the value of the functional data and the one or more predetermined acceptance reference values includes providing to the user an indication of device non-acceptability for medical use.

An aspect of the method further includes receiving, by the ultrasonic medical device control module, the one or more predetermined acceptance reference values from a programmable memory device disposed within the re-assembled ultrasonic medical device.

An aspect of the method further includes programming the programmable memory device with the one or more predetermined acceptance reference values during an initial manufacture of the re-assembled ultrasonic medical device.

In the aspect of the method, receiving functional data from the ultrasonic medical device includes receiving functional data from the ultrasonic medical device referencing a displacement value of a tubular actuating member configured to actuate a jaw of the re-assembled ultrasonic medical device.

In an aspect of the method, receiving functional data from the ultrasonic medical device referencing a displacement value of a tubular actuating member includes receiving data from a Hall Effect sensor configured to measure a displacement value of the tubular actuating member.

In an aspect of the method, receiving functional data from the ultrasonic medical device includes receiving functional data from the ultrasonic medical device referencing a displacement value of a spring stack in mechanical communication with a tubular actuating member configured to actuate the jaw of the re-assembled ultrasonic medical device.

In an aspect of the method, receiving functional data from the ultrasonic medical device referencing a displacement value of a spring stack includes receiving data from a Hall Effect sensor configured to measure a displacement value of the spring stack.

An aspect of the method further includes providing, by the ultrasonic medical device control module, a current to a piezoelectric actuator acoustically coupled to an ultrasonic waveguide, and receiving functional data from the ultrasonic medical device includes receiving functional data from the ultrasonic medical device referencing an impedance associated with the ultrasonic waveguide.

In an aspect of the method, providing, to a user, an acceptability indication based on the comparison of the value of the functional data and the one or more predetermined acceptance reference values includes providing an indication of the presence of a vibration damping membrane in the re-assembled ultrasonic medical device.

In an aspect of the method, providing a current to a piezoelectric actuator acoustically coupled to an ultrasonic waveguide includes providing a current to a piezoelectric actuator configured to induce a transverse mechanical wave in the ultrasonic waveguide.

In an aspect of the method, providing a current to a piezoelectric actuator acoustically coupled to an ultrasonic waveguide includes providing a current to a piezoelectric actuator configured to induce a non-transverse mechanical wave in the ultrasonic waveguide.

In an aspect of the method, providing a current to a piezoelectric actuator acoustically coupled to an ultrasonic waveguide includes providing a current to one or more of a plurality of piezoelectric elements acoustically coupled to the ultrasonic waveguide, in which each of the one or more of the plurality of piezoelectric actuators is configured to induce a non-transverse mechanical wave in the ultrasonic waveguide.

In an aspect of the method, providing, to a user, an acceptability indication based on the comparison of the value of the functional data and the one or more predetermined acceptance reference values includes prompting the user to replace the ultrasonic waveguide or replace an ultrasonic knife acoustically coupled to the ultrasonic waveguide.

An aspect of the method further includes providing, by the ultrasonic medical device control module, a current to a piezoelectric actuator acoustically coupled to an ultrasonic waveguide, and receiving, by the ultrasonic medical device control module, functional data from the ultrasonic medical device referencing a mechanical resonant frequency associated with an ultrasonic waveguide acoustically coupled to the ultrasonic waveguide.

In an aspect of the method, providing, to the user, an acceptability indication includes prompting the user to re-assemble the re-assembled ultrasonic medical device.

In an aspect of the method, receiving functional data from the ultrasonic medical device includes receiving functional data from the ultrasonic medical device referencing a clamp force value of a pad in mechanical communication with the jaw of the ultrasonic medical device against an ultrasonic knife of the re-assembled ultrasonic medical device.

In an aspect of the method, receiving functional data from the ultrasonic medical device referencing a clamp force value includes receiving data from a piezoelectric force sensor mechanically coupled to a component of an actuating member drive assembly configured to actuate the jaw of the re-assembled ultrasonic medical device.

In an aspect of the method, receiving functional data from the ultrasonic medical device includes receiving functional data from the ultrasonic medical device referencing a distance between a distal flange in mechanical communication with an extension tube and a proximal flange in mechanical communication with the extension tube, in which the extension tube is configured to actuate a jaw of the re-assembled ultrasonic medical device.

An aspect of the method further includes prompting, by the ultrasonic medical device control module, the user to initiate a pre-run process comprising a burn-in process, activating, by the ultrasonic medical device control module, the pre-run process for a pre-determined period of time, and determining, by the ultrasonic medical device control module, from the closure data, that the jaw of the end effector is in a closed configuration for the pre-determined period of time, in which receiving functional data from the ultrasonic medical device referencing a functional state of at least one component of the ultrasonic medical device includes receiving functional data referencing a resonant frequency of an ultrasonic knife over the pre-determined period of time.

An aspect of a re-usable ultrasonic medical device includes a handle assembly, an elongated shaft assembly, mechanically coupled to the handle assembly, having an interior distal portion over-molded with an electrically insulating material, in which at least a portion of a proximal interior surface of the elongated shaft assembly is electrically conducting, a first electrical contact electrically coupled to the electrically conducting interior surface of the elongated shaft assembly, an electrically conducting waveguide disposed within the elongated shaft assembly, a second electrical contact electrically coupled to the electrically conducting waveguide, an electrically conducting ultrasonic knife acoustically and electrically coupled to the waveguide, having a distal portion coated with an electrically insulating coating, a generator configured to deliver power to an ultrasonic transducer acoustically coupled to the waveguide, and a controller module configured to control the generator. In the aspect of the re-usable ultrasonic medical device, the controller module includes a processor and a memory circuit configured to contain instructions. In the aspect of the re-usable ultrasonic medical device, the instructions, when executed by the processor, cause the processor to apply an electrical potential between the first contact and the second contact, measure an electrical current flowing between the first contact and the second contact, and notify a user of the re-usable ultrasonic medical device when the voltage has a value outside a tolerance range.

In an aspect of the ultrasonic medical device, the electrically insulating coating of the distal portion of the electrically conducting ultrasonic blade has a proximal coating edge that is distal to a distal edge of the electrically insulating material over-molded on the interior distal portion of the elongated shaft assembly.

An aspect of a method of managing a re-usable ultrasonic medical device, includes receiving, by an ultrasonic medical device control module, an electrical connection from an ultrasonic medical device reassembled by a user, applying, by the ultrasonic medical device control module, an electrical potential between a first contact electrically coupled to an electrically conducting waveguide and a second contact electrically coupled to an electrically conducting inner surface of an elongated shaft assembly, in which the waveguide is disposed in an interior space within the elongated shaft assembly, measuring, by the ultrasonic medical device control module, an electrical current flowing between the first contact and the second contact, comparing, by the ultrasonic medical device control module, a value of the electrical current with one or more values of an acceptance range, and providing, by the ultrasonic medical device control module, to the user an acceptability indication based on the comparison of the value of the electrical current and the one or more predetermined acceptance reference values.

An aspect of the method further includes determining, by the ultrasonic medical device control module, that the value of the electrical current is within the acceptance range, and in which providing to the user an acceptability indication based on the comparison of the value of the electrical current and the one or more predetermined acceptance reference values includes providing to the user an indication of device acceptability for medical use.

An aspect of the method further includes determining, by the ultrasonic medical device control module, that the value of the electrical current is not within the acceptance range, and in which providing to the user an acceptability indication based on the comparison of the value of the electrical current and the one or more predetermined acceptance reference values includes providing to the user an indication of device non-acceptability for medical use.

An aspect of the method further includes prompting, by the ultrasonic medical device control module, the user to clean or re-sterilize a component of the reassembled ultrasonic medical device.

Another aspect of a re-usable ultrasonic medical device includes a handle assembly, an elongated shaft assembly mechanically coupled to the handle assembly at a proximal end, an end effector assembly mechanically coupled at a distal end of the elongated shaft assembly, and a controller module. In the aspect, the handle assembly includes a trigger assembly; a trigger sensor configured to determine a position of the trigger assembly, a yoke mechanically coupled to the trigger assembly, and an actuating member drive assembly. In the aspect, the actuating member drive assembly includes a coupling assembly, having a tube collar having a distal flange and a proximal flange, a spring stack disposed between the distal flange and the proximal flange, and a force sensor mechanically coupled to the spring stack, in which the coupling assembly is configured to receive the yoke between the distal flange and the proximal flange. In the aspect, the elongated shaft assembly includes an outer sheath, a tubular actuating member disposed within the outer sheath, in which a proximal portion of the tubular actuating member is mechanically coupled to the actuating member drive assembly. In the aspect, the end effector assembly includes an ultrasonic knife and a jaw assembly configured to releasably engage the ultrasonic knife, in which the jaw assembly is mechanically coupled to a distal end of the tubular actuating member. In the aspect, the controller module is configured to receive trigger position data from the trigger sensor and force data from the force sensor. In the aspect, one or more components of the re-usable ultrasonic medical device is configured to be replaceable by a user of the medical device.

In the aspect of the re-usable ultrasonic medical device, the force sensor comprises a piezoelectric disk.

In the aspect of the re-usable ultrasonic medical device, the controller module includes a processor and a first memory circuit configured to contain instructions. In the aspect, the instructions, when executed by the processor, cause the processor to determine a value of an electrical potential between a first contact disposed on a first side of the piezoelectric disk and a second contact disposed on a second side of the piezoelectric disk, calculate a force value based on the electrical potential, and notify a user of the re-usable ultrasonic medical device when the force value is outside a tolerance range.

In an aspect of the re-usable ultrasonic medical device, the handle assembly further includes a programmable memory circuit configured to contain stored values corresponding to the tolerance range, and the controller module is configured to receive the stored valued from the memory circuit.

In an aspect of the re-usable ultrasonic medical device, the handle assembly further includes a programmable memory circuit configured to contain potential/force standardization data. Further, in the aspect, the instructions executed by the processor to calculate a force value based on the electrical potential includes instructions to cause the processor to calculate a force value based on the electrical potential and the potential/force standardization data.

The details of one or more implementations are set forth in the accompanying drawings and the description below. Other features and advantages will become apparent from the description, the drawings, and the claims.

BRIEF DESCRIPTION OF THE DRAWINGS

FIG. 7 depicts a perspective view of another aspect of an ultrasonic transducer with associated waveguide in accordance with the present disclosure.

FIG. 8 is an expanded perspective view of an aspect of a portion of the ultrasonic transducer depicted in FIG. 7.

FIG. 9 is a perspective view of an aspect of a portion of an ultrasonic medical device having multiple pairs of piezoelectric transducers in accordance with the present disclosure.

FIG. 16 depicts a diagram of a surgical instrument in accordance with one aspect of the present disclosure.

DETAILED DESCRIPTION

Various aspects described herein are directed to ultrasonic medical devices comprising an ultrasonically actuated, or ultrasonic, blade. In some aspects, an ultrasonic medical device may further include a jaw assembly, located as part of an end effector, which may be used to grasp tissue and move it towards the ultrasonic blade.

The jaw assembly may be articulatable and may pivot about at least two axes. A first axis, or wrist pivot axis, may be substantially perpendicular to a longitudinal axis of the device shaft. The jaw assembly may pivot about the wrist pivot axis from a first position where the jaw assembly is substantially parallel to the ultrasonic blade to a second position where the jaw assembly is not substantially parallel to the ultrasonic blade. In addition, the jaw assembly may comprise first and second jaw members that are pivotable about a second axis or jaw pivot axis. The jaw pivot axis may be substantially perpendicular to the wrist pivot axis. In some aspects, the jaw pivot axis itself may pivot as the jaw assembly pivots about the wrist pivot axis. The first and second jaw members may be pivotably relative to one another about the jaw pivot axis such that the first and second jaw members may "open" and "close." Additionally, in some aspects, the first and second jaw members are also pivotable about the jaw pivot axis together such that the direction of the first and second jaw members may change.

Reference will now be made in detail to several aspects, of ultrasonic medical devices with end effectors comprising ultrasonic surgical elements with or without jaw assemblies. Wherever practicable similar or like reference numbers may be used in the figures and may indicate similar or like functionality. The figures depict example aspects of the disclosed surgical devices and/or methods of use for purposes of illustration only. One skilled in the art will readily recognize from the following description that alternative example aspects of the structures and methods illustrated herein may be employed without departing from the principles described herein.

Particularly, reference will now be made in detail to aspects of an ultrasonic medical device comprising one or more components designed to be cleaned, sterilized, replaced and/or repaired by a user of the device at a medical facility where the device is used. Such a facility may include, without limitation, a hospital, a clinic, or any other facility where the device is used as part of a medical procedure on a patient. For the purpose of this disclosure, a "user" of such an ultrasonic medical device is a person at the medical facility who interacts with the device before, during, and/or after the medical procedure. Such a person may include, without limitation, a physician, a nurse, a physician assistant, a technician, a technologist, or a biomedical engineer.

Figure 1:
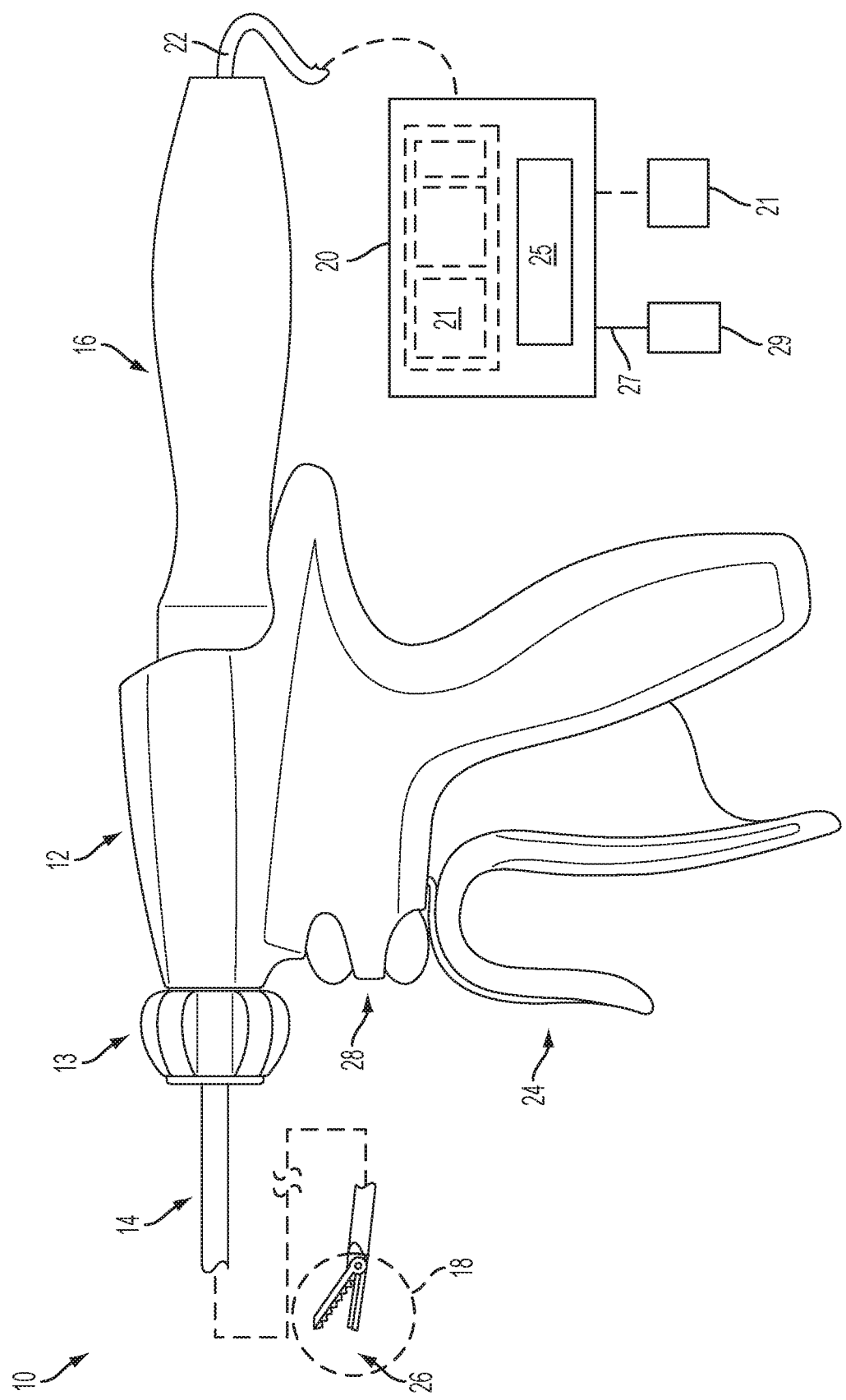
FIGS. 1-2 depict example surgical instruments in in accordance with one aspect of the present disclosure.

FIG. 1 is a right side view of an aspect of an ultrasonic surgical device 10. In the illustrated aspect, the ultrasonic surgical device 10 may be employed in various surgical procedures including endoscopic or traditional open surgical procedures. In an example aspect, the ultrasonic surgical device 10 comprises a handle assembly 12, an elongated shaft assembly 14, and an ultrasonic transducer 16. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical device 10 may be employed in more traditional open surgical procedures and in other aspects, may be configured for use in endoscopic procedures. For the purposes herein, the ultrasonic surgical device 10 is described in terms of an endoscopic device; however, it is contemplated that an open and/or laparoscopic version of the ultrasonic surgical device 10 also may include the same or similar operating components and features as described herein.

In various aspects, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical device 10. In the example aspect illustrated in FIG. 1, the generator 20 includes a control system 25 integral with the generator 20, and a foot switch 29 connected to the generator via a cable 27. The generator 20 may also comprise a triggering mechanism for activating a surgical device, such as the device 10. The triggering mechanism may include a power switch (not shown) as well as a foot switch 29. When activated by the foot switch 29, the generator 20 may provide energy to drive the acoustic assembly of the surgical device 10 and to drive the end effector 18 at a predetermined excursion level. The generator 20 drives or excites the acoustic assembly at any suitable resonant frequency of the acoustic assembly.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

When the generator 20 is activated via the triggering mechanism, electrical energy is continuously applied by the generator 20 to a transducer stack or assembly of the acoustic assembly. In another aspect, electrical energy is intermittently applied (e.g., pulsed) by the generator 20. A phaselocked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a pre-selected constant level in order to achieve substantially constant excursion at the end effector 18 of the acoustic assembly. In yet another aspect, a third feedback loop in the control system 25 monitors impedance between electrodes located in the end effector assembly 26. Although FIGS. 1-4 show a manually operated ultrasonic surgical device, it will be appreciated that ultrasonic surgical devices may also be used in robotic applications, for example, as described herein as well as combinations of manual and robotic applications.

In one aspect, the electrical signal supplied to the acoustic assembly may cause an ultrasonic blade at the distal end of the end effector 18, to vibrate longitudinally (transverse mode) in the range of, for example, approximately 20 kHz to 250 kHz. However, alternative aspects of an ultrasonic medical device, as disclosed herein below, may cause the ultrasonic blade to operate in one or more non-transverse modes. According to various aspects, the blade 22 may vibrate in the range of about 54 kHz to 56 kHz, for example, at about 55.5 kHz. In other aspects, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GENII available from Ethicon Endo-Surgery, Inc.

Figure 2:
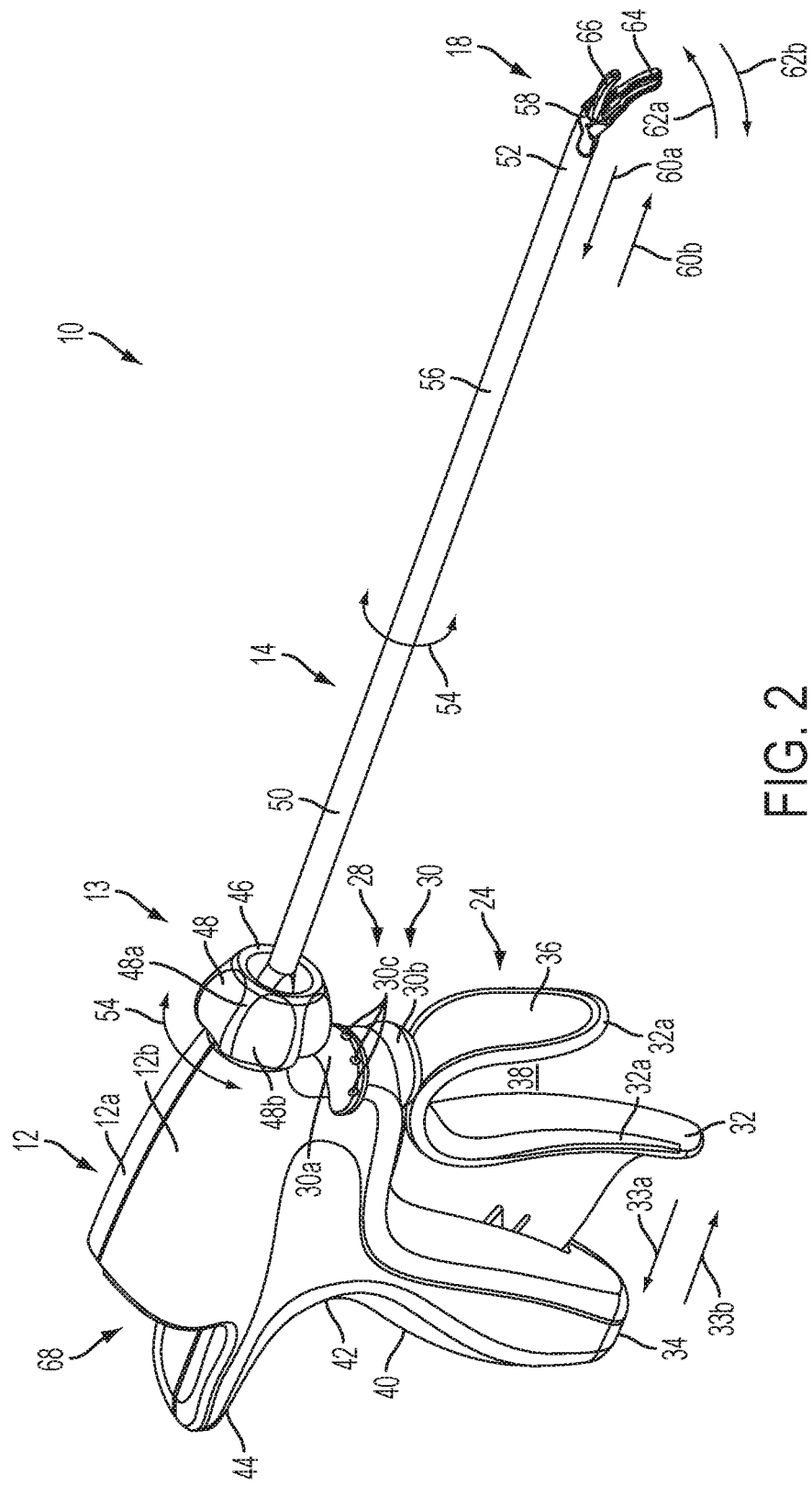

FIG. 2 is a left perspective view of one example aspect of the ultrasonic surgical device 10 showing the handle assembly 12, the distal rotation assembly 13, and the elongated shaft assembly 14. In the illustrated aspect the elongated shaft assembly 14 comprises a distal end 52 dimensioned to mechanically engage the end effector assembly 18 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated shaft assembly 14, the handle assembly 12, and the distal rotation assembly 13 are provided in the description of FIG. 4. In the illustrated aspect, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical device 10. The trigger 32 is pivotally movable in direction 33A toward the fixed handle 34 when the user applies a squeezing force against the trigger 32. A spring element 98 (FIG. 4) causes the trigger 32 to pivotally move in direction 33B when the user releases the squeezing force against the trigger 32.

In one example aspect, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The overmolded resilient portion 32a is formed to provide a more comfortable contact surface for control of the trigger 32 in outward direction 33B. In one example aspect, the overmolded resilient portion 32a may be provided over a portion of the elongated trigger hook 36. The proximal surface of the elongated trigger hook 32 remains uncoated or coated with a non-resilient substrate to enable the user to easily slide their fingers in and out of the aperture 38. In another aspect, the geometry of the trigger forms a fully closed loop which defines an aperture suitably sized to receive one or multiple fingers of the user therethrough. The fully closed loop trigger also may comprise a resilient portion molded over the trigger substrate.

In one example aspect, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example aspect, the switch assembly 28 may comprise a toggle switch 30. The toggle switch 30 may be implemented as a single component with a central pivot 304 located within inside the handle assembly 12 to eliminate the possibility of simultaneous activation. In one example aspect, the toggle switch 30 comprises a first projecting knob 30a and a second projecting knob 30b to set the power setting of the ultrasonic transducer 16 between a minimum power level (e.g., MIN) and a maximum power level (e.g., MAX). In another aspect, the rocker switch may pivot between a standard setting and a special setting. The special setting may allow one or more special programs, processes, or algorithms and described herein to be implemented by the device. The toggle switch 30 rotates about the central pivot as the first projecting knob 30a and the second projecting knob 30b are actuated The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the device to rotate in the hand when the toggle switch 30 is activated.

In one example aspect, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers. In the illustrated aspect, the first projecting knob 30a comprises a plurality of tactile elements 30c, e.g., textured projections or "bumps" in the illustrated aspect, to allow the user to differentiate the first projecting knob 30a from the second projecting knob 30b. It will be appreciated by those skilled in the art that several ergonomic features may be incorporated into the handle assembly 12. Such ergonomic features are described in U.S. Pat. No. 8,623,027 entitled "Ergonomic Surgical Instruments" which is incorporated by reference herein in its entirety.

In one example aspect, the toggle switch 30 may be operated by the hand of the user. The user may easily access the first and second projecting knobs 30a, 30b at any point while also avoiding inadvertent or unintentional activation at any time. The toggle switch 30 may readily operated with a finger to control the power to the ultrasonic assembly 16. For example, the index finger may be employed to activate the first contact portion 30a to turn on the ultrasonic assembly 16 to a maximum (MAX) power level. The index finger may be employed to activate the second contact portion 30b to turn on the ultrasonic assembly 16 to a minimum (MIN) power level. In another aspect, the rocker switch may pivot the device 10 between a standard setting and a special setting. The special setting may allow one or more special programs to be implemented by the device 10. The toggle switch 30 may be operated without the user having to look at the first or second projecting knob 30a, 30b. For example, the first projecting knob 30a or the second projecting knob 30b may comprise a texture or projections to tactilely differentiate between the first and second projecting knobs 30a, 30b without looking.

In one example aspect, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion that is exposed at the distal end. The end cap portion of the hub 46 may contact the surface of a trocar during laparoscopic procedures. The hub 46 may be formed of a hard durable plastic such as polycarbonate to alleviate any friction that may occur between the end cap portion 46a and the trocar. The rotation knob 48 may comprise "scallops" or flutes formed of raised ribs 48a and concave portions 48b located between the ribs 48a to provide a more precise rotational grip. In one example aspect, the rotation knob 48 may comprise a plurality of flutes (e.g., three or more flutes). In other aspects, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example aspect, the handle assembly 12 is formed from two (2) housing portions or shrouds comprising a first portion 12a and a second portion 12b. From the perspective of a user viewing the handle assembly 12 from the distal end towards the proximal end, the first portion 12a is considered the right portion and the second portion 12b is considered the left portion. Each of the first and second portions 12a, 12b includes a plurality of interfaces 69 (FIG. 4) dimensioned to mechanically align and engage each another to form the handle assembly 12 and enclosing the internal working components thereof. The fixed handle 34, which is integrally associated with the handle assembly 12, takes shape upon the assembly of the first and second portions 12a and 12b of the handle assembly 12. A plurality of additional interfaces (not shown) may be disposed at various points around the periphery of the first and second portions 12a and 12b of the handle assembly 12 for ultrasonic welding purposes, e.g., energy direction/deflection points. The first and second portions 12a and 12b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example aspect, the elongated shaft assembly 14 comprises a proximal end 50 adapted to mechanically engage the handle assembly 12 and the distal rotation assembly 13; and a distal end 52 adapted to mechanically engage the end effector assembly 18. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 18. A series of linkages translate the pivotal rotation of the trigger 32 to axial movement of a yoke coupled to an actuation mechanism, which controls the opening and closing of the jaws of the clamping mechanism of the end effector assembly 18. The distal end of the tubular reciprocating tubular actuating member 58 is mechanically engaged to the end effector assembly 18. In the illustrated aspect, the distal end of the tubular reciprocating tubular actuating member 58 is mechanically engaged to a clamp arm assembly 64, which is pivotable about a pivot point 70 (FIG. 3), to open and close the clamp arm assembly 64 in response to the actuation and/or release of the trigger 32. For example, in the illustrated aspect, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example aspect, the end effector assembly 18 is attached at the distal end 52 of the elongated shaft assembly 14 and includes a clamp arm assembly 64 and a blade 66. The jaws of the clamping mechanism of the end effector assembly 18 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad 330, for example mechanically coupled to a surface of the clamp arm assembly 64, to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example aspect, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 326 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 4) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user the may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

Figure 3:
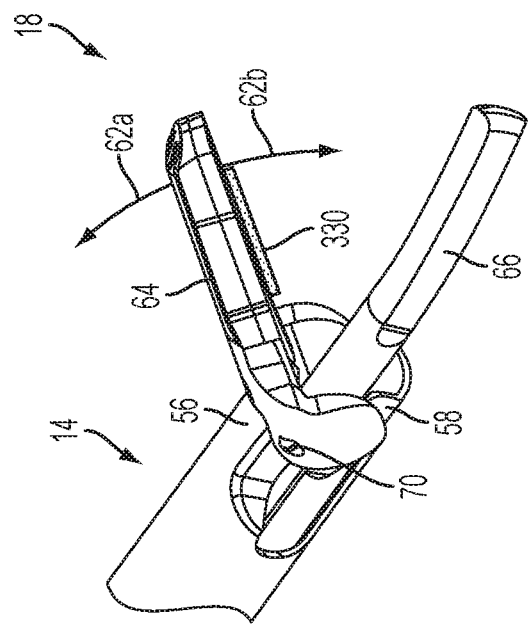
FIG. 3 depicts an example of an end effector and a shaft of a surgical instrument in accordance with one aspect of the present disclosure.

FIG. 3 illustrates the connection of the elongated shaft assembly 14 relative to the end effector assembly 18. As previously described, in the illustrated aspect, the end effector assembly 18 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad 330 to engage tissue between the blade 66 and the clamp arm 64. The distal end of the tubular reciprocating tubular actuating member 58 is mechanically engaged to the end effector assembly 18. In the illustrated aspect, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated aspect, the clamp arm assembly 64 is movable from an open position to a closed position in direction 62B about a pivot point 70 when the trigger 32 is squeezed in direction 33A. The clamp arm assembly 64 is movable from a closed position to an open position in direction 62A about the pivot point 70 when the trigger 32 is released or outwardly contacted in direction 33B.

Figure 4:
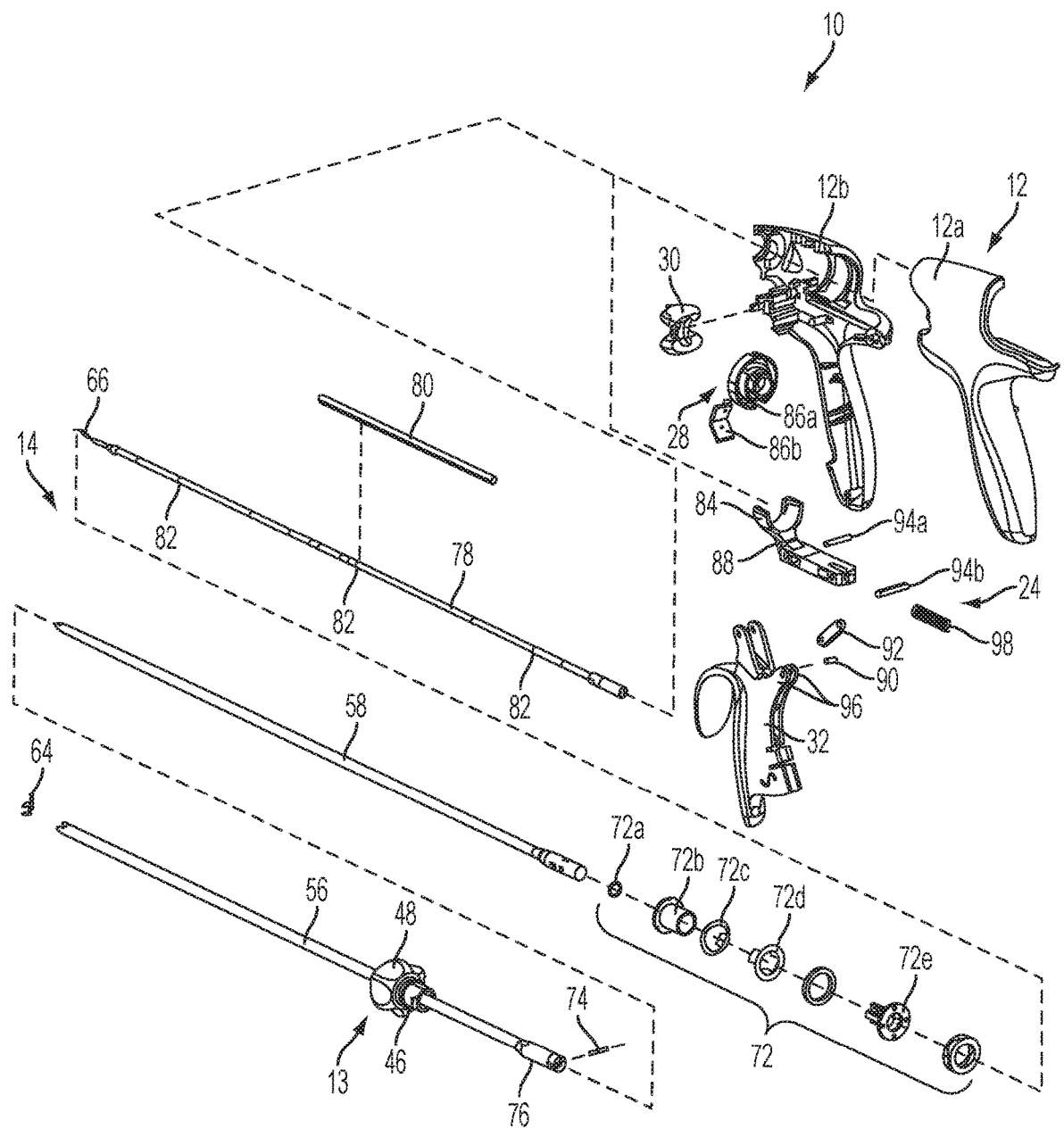
FIG. 4 depicts an exploded view of an aspect of a surgical instrument in in accordance with one aspect of the present disclosure.

FIG. 4 is an exploded view of the ultrasonic surgical device 10 shown in FIG. 2. In the illustrated aspect, the exploded view shows the internal elements of the handle assembly 12, the handle assembly 12, the distal rotation assembly 13, the switch assembly 28, and the elongated shaft assembly 14. In the illustrated aspect, the first and second portions 12a, 12b mate to form the handle assembly 12. The first and second portions 12a, 12b each comprises a plurality of interfaces 69 dimensioned to mechanically align and engage one another to form the handle assembly 12 and enclose the internal working components of the ultrasonic surgical device 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72a, a tube collar cap 72b, a distal washer 72c, a proximal washer 72d, and a thread tube collar 72e. The reciprocating tubular actuating member 58 is located within a reciprocating yoke 84, which is retained between the first and second portions 12a, 12b of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical device 10. In one example aspect, a four-link design provides mechanical advantage in a relatively short rotation span, for example.

In one example aspect, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16. The ultrasonic transmission waveguide 78 is isolated from the other elements of the elongated shaft assembly 14 by a protective sheath 80 and a plurality of isolation elements 82, such as silicone rings. In some aspects, the protective sheath 80 may serve as a vibration damping membrane that may isolate the user from the mechanical vibrations induced in the waveguide and/or ultrasonic blade. In some examples, the protective sheath 80 may be fabricated as a tubular component in which the ultrasonic transmission waveguide 78 is disposed. In other examples, the protective sheath may be fabricated as a flat membrane that is formed into a partial cylindrical plate for insertion into the ultrasonic medical device 10. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86a,b to electrically energize the ultrasonic transducer 16 in accordance with the activation of the first or second projecting knobs 30a, 30b.

In one example aspect, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 24 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 may allow the assembly to be torqued to a required level. In one example aspect, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example aspect, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example aspect, the trigger 32 is coupled to a linkage mechanism to translate the rotational motion of the trigger 32 in directions 33A and 33B to the linear motion of the reciprocating tubular actuating member 58 in corresponding directions 60a and 60b (FIG. 2). The trigger 32 comprises a first set of flanges 98 with openings formed therein to receive a first yoke pin 94a. The first yoke pin 94a is also located through a set of openings formed at the distal end of the yoke 84. The trigger 32 also comprises a second set of flanges 96 to receive a first end of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12a, 12b of the handle assembly 12 to form a trigger pivot point for the trigger 32. A second end of the link 92 is received in a slot formed in a proximal end of the yoke 84 and is retained therein by a second yoke pin 94b. As the trigger 32 is pivotally rotated about a pivot point formed by the trigger pin 90, the yoke translates horizontally along a longitudinal axis "T" in a direction indicated by arrows 60a,b.

Figure 5:
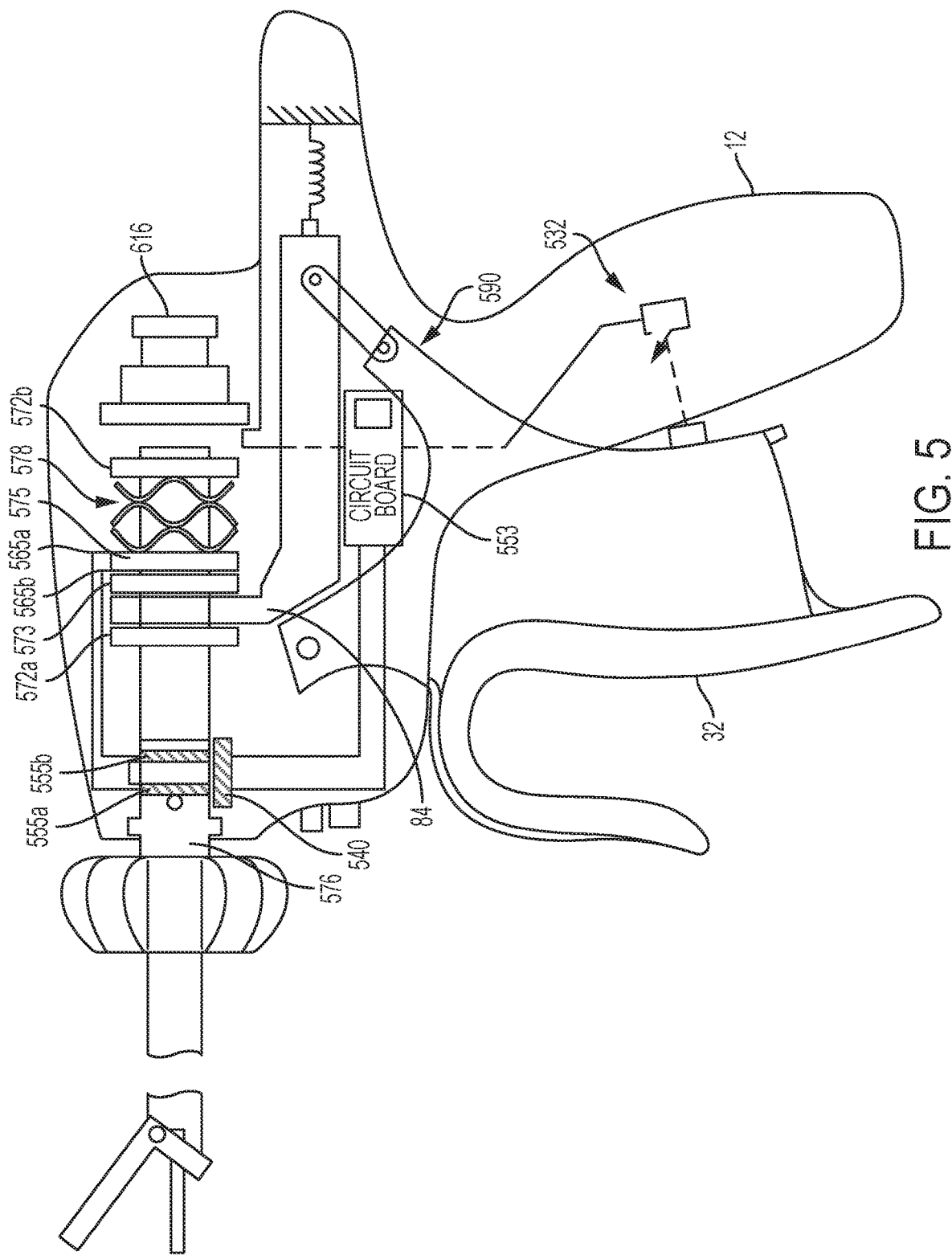
FIG. 5 depicts an interior view of one aspect of an ultrasonic medical device in accordance with the present disclosure.

FIG. 5 depicts another aspect of the ultrasonic medical device 10, including additional components. Thus, the reciprocating tubular actuating member 58 may be coupled to a reciprocating collar comprising a distal flange 572a and a proximal flange 572b. The reciprocating yoke 84 may engage the reciprocating collar in some position disposed between the distal flange 572a and proximal flange 572b. The reciprocating collar may be disposed within a spring stack 578. The spring stack 578 may be disposed between the reciprocating yoke 84 and the proximal flange 572b. An additional bearing plate 573 may be positioned between the reciprocating yoke 84 and a distal end of the spring stack 578, thereby protecting the spring stack 578 from mechanical deformation by the reciprocating yoke 84 when the trigger 32 is actuated.

When the trigger 32 is actuated, the reciprocating yoke 84 may be pulled in a proximal direction, thereby pulling the reciprocating tubular actuating member 58 in a proximal direction. As the reciprocating yoke 84 moves proximally, it may pull against the bearing plate 573 and compressing the spring stack 578. Once the trigger is released, the compressed spring stack 578 provides a restoring force to the reciprocating tubular actuating member 58 thereby pushing it back in a distal direction.

The ultrasonic medical device 10 may also include an ultrasonic transducer 16 acoustically coupled to the waveguide 78. The ultrasonic medical device 10 may further include any number of sensors and sensor electronics adapted to measure functional data associated with the operation of one or more of the components of the ultrasonic medical device 10, as will be detailed below.

Figure 6:
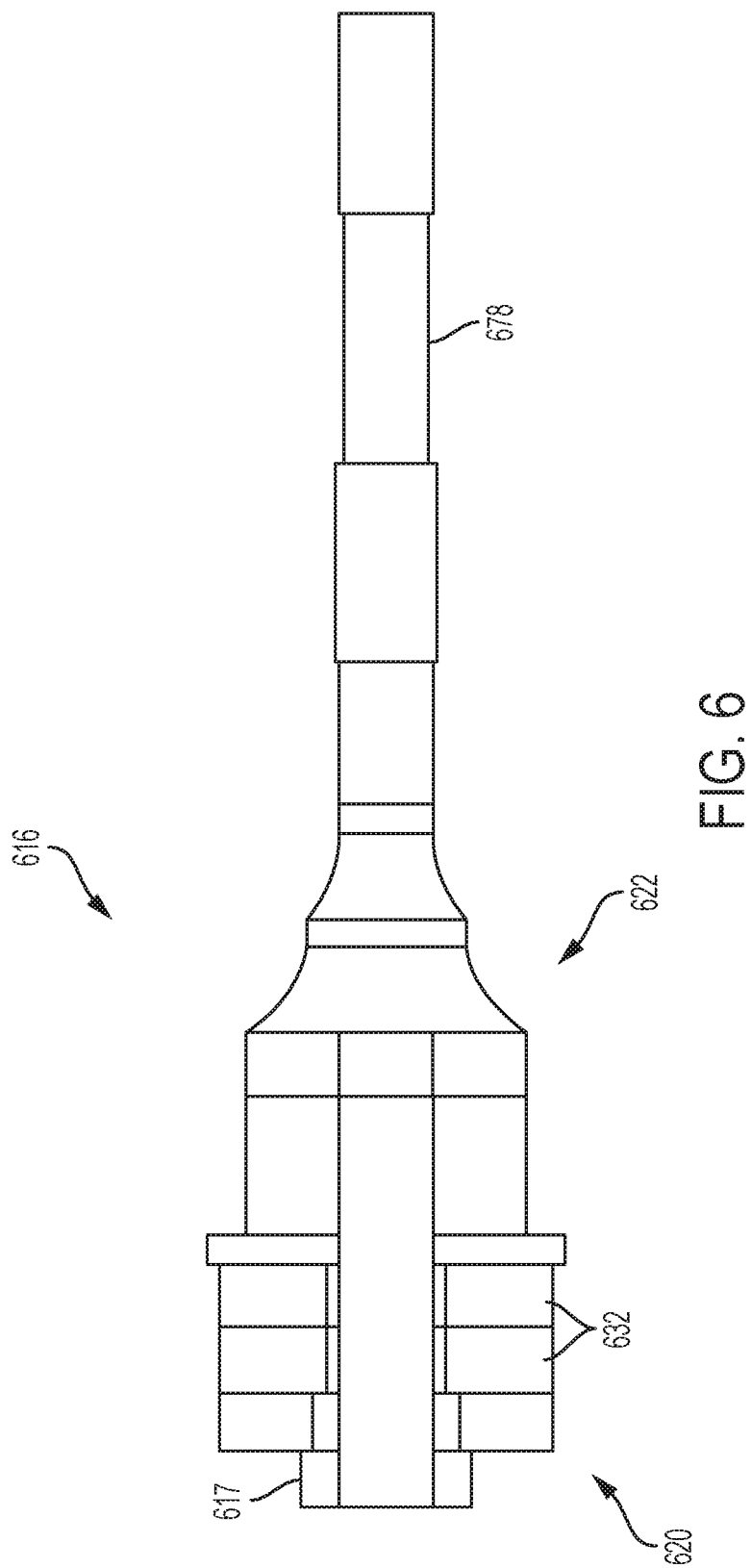
FIG. 6 depicts a view of one aspect of an ultrasonic transducer in accordance with the present disclosure.

FIG. 6 depicts one aspect of an ultrasonic transducer 16 may comprise an ultrasonic transducer assembly 616. One aspect of the ultrasonic medical device 10 comprises an ultrasonic signal generator module 21 electrically coupled to an ultrasonic transducer 16. In one aspect, the ultrasonic transducer assembly 616, may comprise a plurality of cylindrical piezoelectric transducers 632 disposed in a "Langevin stack." Such a "Langevin stack," may induce a transverse acoustic wave in an ultrasonic waveguide 678 when acoustically coupled thereto. Each of the piezoelectric transducers 632 may be actuated by the application of a voltage across opposing faces thereof. The ultrasonic transducer assembly 616 may further include a first resonator or end-bell 620 coupled proximally to the piezoelectric transducers 632, and a second resonator or fore-bell 622 coupled distally to the piezoelectric transducers 632, and ancillary components. In various aspects, the ultrasonic transducer assembly 616 is preferably an integral number of one-half system wavelengths (nλ/2) in length as will be described in more detail below. The ultrasonic acoustic assembly 616 can further include a mount and a velocity transformer.

The distal end of the end-bell 620 is connected to the proximal end of the "Langevin stack," and the proximal end of the fore-bell 622 is connected to the distal end of the Langevin stack." The fore-bell 622 and the end-bell 620 have a length determined by a number of variables, including the thickness of the Langevin stack," the density and modulus of elasticity of the material used to manufacture the end-bell 620 and the fore-bell 622, and the resonant frequency of the ultrasonic transducer assembly 616. The fore-bell 622 may be tapered inwardly from its proximal end to its distal end to amplify the ultrasonic vibration amplitude. Alternatively, the fore-bell 622 may have no amplification.

Referring again to FIG. 6, the end-bell 620 can include a threaded member extending therefrom which can be configured to be threadably engaged with a threaded aperture in fore-bell 622. In various aspects, piezoelectric elements, such as piezoelectric elements 632, for example, can be compressed between the end-bell 620 and the fore-bell 622 when the end-bell 620 and the fore-bell 622 are assembled together. The ultrasonic transducer assembly 616 may include a tail portion 617 that may also provide compressive force to the piezoelectric elements 632 through the end-bell 620. It may be recognized that proper compression of the piezoelectric elements 632 between the end-bell 620 and the fore-bell 622 may be useful to assure good mechanical coupling between the piezoelectric elements 632 and the fore-bell 622. Good mechanical coupling may optimize the transmission of the motion induced in the piezoelectric elements 632 by an electrical field into the distal components of the ultrasonic system 10. Piezoelectric elements 632 may be fabricated from any suitable material, such as, for example, lead zirconate-titanate, lead meta-niobate, lead titanate, and/or any suitable piezoelectric crystal or ceramic material, for example.

In various aspects, as discussed in greater detail below, ultrasonic transducer assembly 616 can further comprise electrodes, such as positive electrodes and negative electrodes for example, which can be configured to create a voltage potential across one or more piezoelectric elements 632. Each of the positive electrodes, negative electrodes, and the piezoelectric elements 632 can comprise a bore extending through the center which can be configured to receive the threaded member of end-bell 620. In various aspects, the positive and negative electrodes are electrically coupled to wires encased within a cable and electrically connectable to the ultrasonic signal generator 21 of the ultrasonic system 10.

In various aspects, the ultrasonic transducer 616 having piezoelectric elements 632 disposed in a "Langevin stack" converts the electrical signal from the ultrasonic signal generator 21 into mechanical energy that results in primarily longitudinal (transverse mode) vibratory motion at ultrasonic frequencies of the ultrasonic transducer assembly 616 through a waveguide 678 to the end effector assembly 18. A suitable generator is available as model number GEN11, from Ethicon Endo-Surgery, Inc., Cincinnati, Ohio. When the ultrasonic transducer assembly 616 is energized, a vibratory motion standing wave is generated through the waveguide 678. A suitable vibrational frequency range may be about 20 Hz to 120 kHz and a well-suited vibrational frequency range may be about 30-70 kHz and one example operational vibrational frequency may be approximately 50 kHz.

The amplitude of the vibratory motion at any point along the ultrasonic transducer assembly 616 and waveguide 678 (together comprising an acoustic assembly) may depend upon the location along the acoustic assembly at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength (λ/4).

In various aspects, the ultrasonic energy produced by ultrasonic transducer assembly 616 can be transmitted to the end effector assembly 18 via the ultrasonic transmission waveguide 678. In order for the acoustic assembly to deliver energy to the end effector assembly 18, the components of the acoustic assembly are acoustically coupled to the end effector assembly 18. For example, the distal end of the ultrasonic transducer 616 may be acoustically coupled the proximal end of the ultrasonic transmission waveguide 678 by a threaded connection.

The components of the acoustic assembly can be acoustically tuned such that the length of any assembly is an integral number of one-half wavelengths (nλ/2), where the wavelength λ is the wavelength of a pre-selected or operating longitudinal vibration drive frequency $f_d$ of the acoustic assembly, and where n is any positive integer. It is also contemplated that the acoustic assembly may incorporate any suitable arrangement of acoustic elements.

The ultrasonic end effector 18 may have a length substantially equal to an integral multiple of one-half system wavelengths (λ/2). A distal end of the ultrasonic end effector 18 may be disposed at, or at least near, an antinode in order to provide the maximum, or at least nearly maximum, longitudinal excursion of the distal end for an ultrasonic transducer assembly 616 comprising piezoelectric elements 632 disposed in a "Langevin stack". When the transducer assembly is energized, in various aspects, the distal end of the ultrasonic end effector 18 may be configured to move in the range of, for example, approximately 10 to 500 microns peak-to-peak and preferably in the range of approximately 30 to 150 microns at a predetermined vibrational frequency.

As outlined above, the ultrasonic end effector 18 may be coupled to the ultrasonic transmission waveguide 678. In various aspects, the ultrasonic end effector 18 and the ultrasonic transmission guide 678 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 18 may be separable (and of differing composition) from the ultrasonic transmission waveguide 678, and coupled by, for example, a stud, weld, glue, quick connect, or other suitable known methods. The ultrasonic transmission waveguide 678 may have a length substantially equal to an integral number of one-half system wavelengths (λ/2), for example. The ultrasonic transmission waveguide 678 may be preferably fabricated from a solid core shaft constructed out of material that propagates ultrasonic energy efficiently, such as titanium alloy (i.e., Ti6Al4V) or an aluminum alloy, for example.

In general, a voltage, or power, source can be operably coupled with one or more piezoelectric elements of an ultrasonic transducer assembly, wherein a voltage potential applied to each of the piezoelectric elements can cause the piezoelectric elements to expand and contract or vibrate. As also described above, the voltage potential can be cyclical and, in various aspects, the voltage potential can be cycled at a frequency which is the same as, or nearly the same as, the resonant frequency of the system of components comprising ultrasonic transducer assembly 616, wave guide 678, and end effector 18, for example.

Power may be maximized by operating the piezoelectric elements 632 at a frequency at or near a node or resonant frequency ($f_r$) in which the impedance of the ultrasonic transducer assembly 616 is at a minimum. A minimum amount of power may be required to operate the piezoelectric elements 632 at a frequency at or near an anti-node or anti-resonant frequency ($f_a$) in which the impedance of the ultrasonic transducer assembly 616 is at a maximum.

FIG. 6 depicts one aspect of an acoustic assembly that may be configured to induce a standing transverse wave of mechanical energy to an end effector of an ultrasonic surgical device. FIGS. 7-9 depict additional aspects of acoustic assemblies that may be configured to induce non-transverse mechanical energy to the end effector.

FIG. 7 illustrates an aspect of an ultrasonic acoustic assembly 700 that incorporates one or more piezoelectric transducers 912a,b configured to operate in a D31 mode. The ultrasonic acoustic assembly 700 may include a waveguide 378 and a transducer mounting portion 320. In some aspects, the acoustic assembly 700 may be fabricated from sheet stock and have essentially flat faces 325 and side edges 327 orthogonal to the flat faces 325. The waveguide 378 may be acoustically coupled to an end effector 18 at a distal end and the transducer mounting portion 320 located at a proximal end of the acoustic assembly 700. One or more piezoelectric transducers 912a,b may be affixed to the transducer mounting portion 320 of the acoustic assembly 700. In certain aspects, the waveguide 378 may also include one or more stabilizing silicone rings or compliant supports positioned at, or at least near, a plurality of vibration nodes, which may dampen undesirable vibration and isolate the ultrasonic energy from a sheath at least partially surrounding the acoustic assembly 700. In order for the piezoelectric transducers 912a,b to operate in a D31 mode, a first electrode may be electrically coupled to an exposed face of a transducer (for example 912a) that is opposite to the face of the transducer in mechanical communication with a face 325 of the acoustic assembly 700. In some aspects, a conductive electrode (for example, a silver electrode) may be painted or screen printed on an exposed face of the piezoelectric transducers 912a,b and conducting wires may then be soldered onto the conductive electrodes. Alternatively, the wires may be affixed to the exposed faces of the piezoelectric transducers 912a,b by means of a conductive epoxy. The acoustic assembly 700 may be electrically coupled to a second electrode, thereby permitting an electric field to be imposed on the acoustic assembly 700 orthogonal to a longitudinal axis of the waveguide 378.

FIG. 8 is a close-up view of the transducer mounting portion 320 of the acoustic assembly 700 of FIG. 7, illustrating the mechanical contacts that may be made between a face of each of the piezoelectric transducers 912a,b and a face 325 of the acoustic assembly 700. In the aspect illustrated in FIG. 8, a single pair of piezoelectric transducers 912a,b contact the acoustic assembly 700, each transducer contacting an opposing face of the acoustic assembly 700. It may be observed that each of the pair of piezoelectric transducers 912a,b is positioned opposite the other. As disclosed above with respect to FIG. 6, the piezoelectric transducers 912a,b may be activated by a power source at a predetermined frequency to induce a standing mechanical wave along the body of the acoustic assembly 700. The standing wave may be proportional to the predetermined frequency component of the electrical signal. The standing wave induced along the body of the acoustic assembly 700 may be characterized by one or more nodes and anti-nodes. The standing wave nodes may be effectively centered at one or more node locations on the acoustic assembly 700, and the standing wave anti-nodes may be effectively centered at one or more anti-node locations on the acoustic assembly 700. Each piezoelectric transducer 912a,b may be symmetrically disposed about a node location in the transducer mounting portion 320 of the acoustic assembly 700. Such a disposition may result in each transducer 912a,b contacting a portion of the acoustic assembly 700 at a location having minimal mechanical displacement during the activation of the transducers 912a,b.

FIG. 9 illustrates an aspect in which a first transducer 912a comprises a first planar array of first transducer plates and the second transducer 912b comprises a second planar array of second transducer plates. As illustrated in FIG. 9, the first transducer 912a comprises a first planar array of first transducer plates indicated by numbers 1, 2, 3, and 4. The second transducer 912b comprises a second planar array of second transducer plates (not visible in the perspective view of FIG. 9) indicated by numbers in parentheses (5), (6), (7), and (8). It may be understood that second transducer plate (5) is disposed on an opposing side of the transducer mounting portion 320 with respect to first transducer plate 1, second transducer plate (6) is disposed on an opposing side of the transducer mounting portion 320 with respect to first transducer plate 2, second transducer plate (7) is disposed on an opposing side of the transducer mounting portion 320 with respect to first transducer plate 3, and second transducer plate (8) is disposed on an opposing side of the transducer mounting portion 320 with respect to first transducer plate 4. Transducer plates 1, (5), 3, and (7) may be disposed about one side of a node location and transducer plates 2, (6), 4, and (8) may be disposed about an opposing side of the node location.

It may be understood that the transducers or transducer plates depicted in the aspects in FIGS. 7-9 may all be made of the same material. Alternatively, the transducers or transducer plates depicted in the aspects in FIGS. 7-9 may be made of different materials. For example the transducers or transducer plates may be fabricated from piezoelectric materials that differ in their respective strain constants, dielectric dissipation or dampening properties, dielectric constants, voltage sensitivities, or Currie temperatures. Similarly, the transducers or transducer plates may all have the same shape and size. Alternatively, transducers or transducer plates may differ in shape, size, or both shape and size depending on their respective placements on the surgical tool or on each other.

Each transducer or transducer plate illustrated in FIGS. 7-9 may be individually activated. In some aspects, each transducer or transducer plate may be activated by a separate ultrasonic signal generator in which the individual ultrasonic signal generators have a common ground in electrical communication with the acoustic assembly. In such an aspect, each transducer or transducer plate may be activated by a separate electric signal. In some examples, the electrical characteristics of the separate electrical signals may be the same, for example having the same amplitude, frequency, and phase. In alternative examples, the electrical characteristics of the separate electrical signals may differ in one or more of amplitude, frequency, and phase. In alternative aspects, each transducer or transducer plate may be activated by the same ultrasonic signal generator, but may be separately activatable by one or more transducer activation switches. Such switches may direct a first polarity of an ultrasonic signal to one set of transducers or transducer plates and a second polarity of the ultrasonic signal to a second set of transducers or transducer plates. It may be understood that such switches may also be used to disconnect one or more transducers or transducer plates from the ultrasonic signal generator while allowing other transducers or transducer plates to receive an ultrasonic signal from the ultrasonic signal generator.

In at least one such aspect, the ultrasonic surgical device can comprise one or more switches which can be configured to selectively actuate the transducers or transducer plates. For example, a switch can be moved from an off position to a first position in order to actuate a first transducer or set of transducer plates, to a second position to actuate the second transducer or set of transducer plates. It may be recognized that in an aspect such as depicted in FIG. 9, such a switch may have multiple positions, each position configured to actuate a specified group of transducer plates. In certain other aspects, ultrasonic medical device can comprise a first switch configured to selectively actuate a first transducer or set of transducer plates, and, in addition, a second switch configured to selectively actuate the second transducer or set of transducer plates. In such aspects, the surgeon can select the power to be supplied to the surgical tool and/or end effector. In an alternative aspect, control of the power supplied to any one or more of the transducers or set of transducer plates may be automated according to instructions resident in a memory component of the control system 25.

It may be recognized that switched activation of the transducers or transducer plates may result in vibrational patterns of the surgical tool that are more complex than a single transverse standing mechanical wave. Such complex mechanical waves may be used to impart complex movement to the end effector of the ultrasonic medical device. For example, with respect to the aspect illustrated in FIG. 9, a predominantly transverse flapping motion may be induced in the end effector if transducer plates 1, 2, (5), and (6) are activated with a first polarity ultrasonic signal while transducer plates 3, 4, (7), and (8) are activated with a second and opposing polarity ultrasonic signal. A predominantly transverse hooking motion may be induced in the end effector if transducer plates 1, (5), 3, and (7) are activated with a first polarity ultrasonic signal while transducer plates 2, (6), 4, and (8) are activated with a second and opposing polarity ultrasonic signal. A predominantly torsional motion may be induced in the end effector if transducer plates 1, (7), 2, and (8) are activated with a first polarity ultrasonic signal while transducer plates 3, (5), 4, and (6) are activated with a second and opposing polarity ultrasonic signal. A combination of torsional and transverse motions may be induced in the end effector if transducer plates 1, (7), 4, and (6) are activated with a first polarity ultrasonic signal while transducer plates (5), 3, 2, and (8) are activated with a second and opposing polarity ultrasonic signal. Additional motions may be achieved through the activation of other groups of transducer plates.

From FIGS. 1-9 and the accompanying disclosures, it may be apparent that a number of components of an ultrasonic medical device 10 may require cleaning, sterilization, replacement, or repair as a result of the use of the device. In one example, an ultrasonic blade 66 may become coated with tissue after use, or may suffer from pitting, cracking, and/or crazing due to the induced mechanical vibration during use, thus requiring the blade 66 to be cleaned, sterilized, and/or replaced. The clamp arm assembly 64 may fail to rotate completely about the pivot point 70 due to a build-up of tissue at the pivot, thus requiring cleaning or repair. The pad 330 may similarly suffer from a build-up of tissue material during use, or may develop surface wear due to exposure to the vibrating ultrasonic blade 66, thus requiring cleaning or replacement. A distal end of the outer tubular sheath 56 may similarly accumulate biological debris both on its outer surface and its inner surface and require cleaning. A build-up of biological debris in the interior of the tubular sheath 56 may affect the performance of the reciprocating tubular actuating member 58, reducing or impairing its travel. Induced vibrations in the waveguide (for example 78) may result in material fatigue and ultimately result in cracks or bends in the waveguide, thus requiring repair and/or replacement. Wear may be induced in the protective sheath 80 due to constant exposure to the vibrations of the waveguide, and thus require replacement.

Additional wear may occur to the mechanical components housed in the handle assembly 12. Spring element 98 and spring stack 578 may lose resiliency after multiple expansions or compressions, and thus may require replacement. It may also be recognized that one or more components of an ultrasonic transducer assembly (for example 616) may suffer from mechanical wear and require either repair and/or replacement. In one non-limiting example, mechanical vibrations may cause the components of the ultrasonic transducer assembly 616 (for example, the tail portion 617, the end bell 620, and the fore-bell 622) to loosen, thereby reducing the mechanical coupling between the piezoelectric transducers (for example 632) and the waveguide (for example 678). Similarly, mechanical vibrations at the interface of the waveguide 678 and the ultrasonic transducer assembly 616 may reduce the mechanical coupling of the transducer assembly 616, through the waveguide 678, to the ultrasonic blade 66.

It may be recognized that such examples of wear and tear on the components of the ultrasonic medical device 10 are non-limiting, and that other components not mentioned herein may also require cleaning, replacement, and/or repair. As disclosed above, although it is beneficial for a user of the ultrasonic medical device to effect cleaning, replacement, and/or repair of fouled, broken, and/or damaged components, the user must be able to successfully reassemble the medical device 10 after servicing and before its subsequent reuse. Therefore, it is useful for the reusable medical device to incorporate features to assure that the medical device functions properly upon reassembly or to notify a user that the reassembly was not successful and not use the reassembled medical device 10 until proper reassembly has occurred.

In some aspects, features to assist a user in proper reassembly of the medical device 10 may include a variety of sensors. Such sensors may be disposed in any of a number of locations in the device, and may be configured to measure mechanical functions of the device components. Additionally, such sensors may alert a user that one or more components of the medical device 10 warrant inspection, cleaning, replacement, and/or repair.

Returning to FIG. 5, some non-limiting examples of such sensors may include a trigger sensor 532. Such a trigger sensor 532 may comprise a force sensor, configured to indicate an amount of force being applied to the trigger 32 on actuation. Alternatively, the trigger sensor 532 may comprise a position sensor, configured to determine how far the trigger 32 has been depressed by a user. In one non-limiting aspect, the trigger sensor 532 may be coupled electrically to a circuit board 553 that may include a variety of device electronics which may include electronics configured to accept electrical data from one or more sensors disposed within the medical device 10. Examples of such a trigger sensor 532 may include, without limitation, a magnetic proximity sensor, an inductance sensor, a capacitive sensor, a resistive sensor, and an optical sensor Another example of a sensor may be a spring force sensor configured to measure a compression force on the spring stack 578 by the yoke 84 when the trigger 32 is depressed. The yoke 84 may move in a proximal direction, by means of a trigger assembly linkage 590, when the trigger 32 is depressed. In one non-limiting embodiment, the spring force sensor may comprise a piezoelectric disk 575 disposed between the yoke 84 and the spring stack 578. It is recognized that an electrical potential is created between the two surfaces of a piezoelectric material when the material is compressed. Thus, the spring force sensor comprising a piezoelectric disk 575 may include electrical contacts to the surfaces of the piezoelectric disk 575.

As depicted in FIG. 5, a proximal surface contact 565a and a distal surface contact 565b may be coupled electrically to the respective proximal and distal surfaces of the piezoelectric disk 575. The proximal and distal surface contacts, 565a,b respectively, may be electrically coupled to hub contacts 555a,b, respectively, that may be disposed on the hub 576 of the elongated shaft assembly 14. As disclosed above, the elongated shaft assembly 14 along with the outer tubular sheath 56 and the reciprocating tubular actuating member 58 are configured to rotate about a longitudinal axis with respect to the handle assembly 12. As a result, a rotating slip joint 540 may be provided to allow hub contacts 555a,b to maintain electrical connectivity with wires or other electrical conduction components that may be fixed in the frame of reference in the handle assembly 12. In one non-limiting example, the electrical conduction components may terminate in the circuit board 553 comprising one or more sensor electronics configured to receive one or more electrical signals from sensor components associated with the ultrasonic medical device 10.

Although FIG. 5 depicts that the piezoelectric disk 575 is located between the bearing plate 573 and a distal end of the spring stack 578, it may be recognized that the piezoelectric disk 575 may be suitably placed anywhere along the reciprocating collar between the yoke 84 and the proximal flange 572b in order to measure the compressive force of the spring stack 578. Thus, as non-limiting examples, the piezoelectric disk 575 may also be located between a proximal surface of the yoke 84 and a distal surface of the bearing plate 573, or between a proximal end of the spring stack 578 and a distal surface of the proximal flange 572b.

Several types or configurations of sensors may be employed to assure that the components configured to actuate the jaw of the clamp arm assembly 64 operate properly. Examples of such components may include, without limitation, the reciprocating tubular actuating member 58, the reciprocating collar including the distal flange 572a and the proximal flange 572b thereof, and the spring stack 578. FIGS. 10-15 depict several sensors that may be used individually or in any combination or combinations to sense the motion of the components.

Figure 10A:
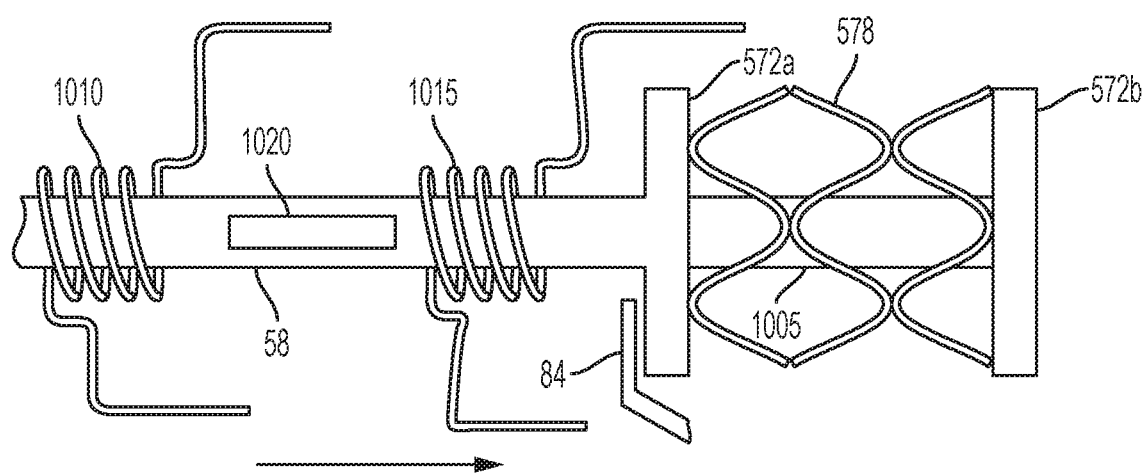
FIGS. 10A and 10B depict an aspect of inductive sensors configured to detect a motion of a reciprocating tube component of an ultrasonic medical device in accordance with the present disclosure.
Figure 10B:
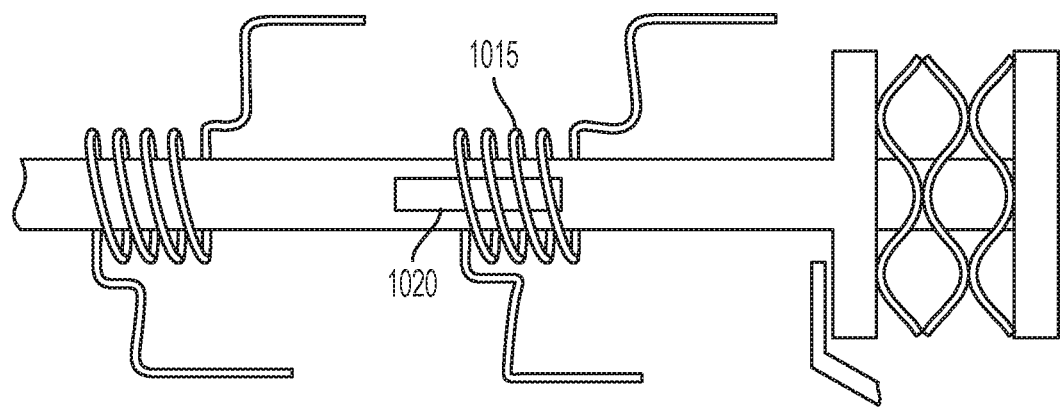

FIGS. 10-11 depict one or more sensors that may provide an indication of the reciprocating motions of the reciprocating tubular actuating member 58. In one aspect, depicted in FIGS. 10A and 10B, the reciprocating tubular actuating member 58 may be disposed within one or more inductive loops 1010, 1015. The reciprocating tubular actuating member 58 may include one or more ferroelectric metallic strips 1020 disposed along a portion of the outer surface of the reciprocating tubular actuating member 58. It may be understood that a tubular collar made of a ferroelectric material may be substituted for the one or more ferroelectric metallic strips 1020. In one non-limiting example, the one or more ferroelectric metallic strips 1020 may be disposed within a sensing inductive loop 1015 when the jaw is in an open state. As the reciprocating tubular actuating member 58 translates in the proximal direction as depicted by the arrow in FIG. 10A (and the jaw changes to a closed state), the one or more ferroelectric metallic strips 1020 may be translated into the sensing inductive loop 1015, as depicted in FIG. 10B, thereby changing the inductance of the sensing inductive loop 1015. The sensing inductive loop 1015 may form a portion of a tuned circuit, and a change in resonant frequency may be detected as the sensing inductance loop 1015 impedance changes. A second, reference, inductive loop 1010 may also be provided as part of an impedance bridge to measure a change in circuit impedance as the reciprocating tubular actuating member 58 translates during jaw actuation. It may be further understood that such an inductive sensing mechanism may operate in a reverse mode, in which the one or more ferroelectric metallic strips 1020 may be translated out of the sensing inductive loop 1015, when the reciprocating tubular actuating member 58 translates during jaw actuation. It may be recognized that the output of the inductive sensing mechanism may provide a measure either of a position of the reciprocating tubular actuating member 58 or an amount of travel of the reciprocating tubular actuating member 58. Drive and detection electronics for the one or more inductive loops 1010, 1015, including an oscillator and measurement electronics (for either a voltage, a current, or both a voltage and current), may be located on circuit board 553.

Figure 11A:
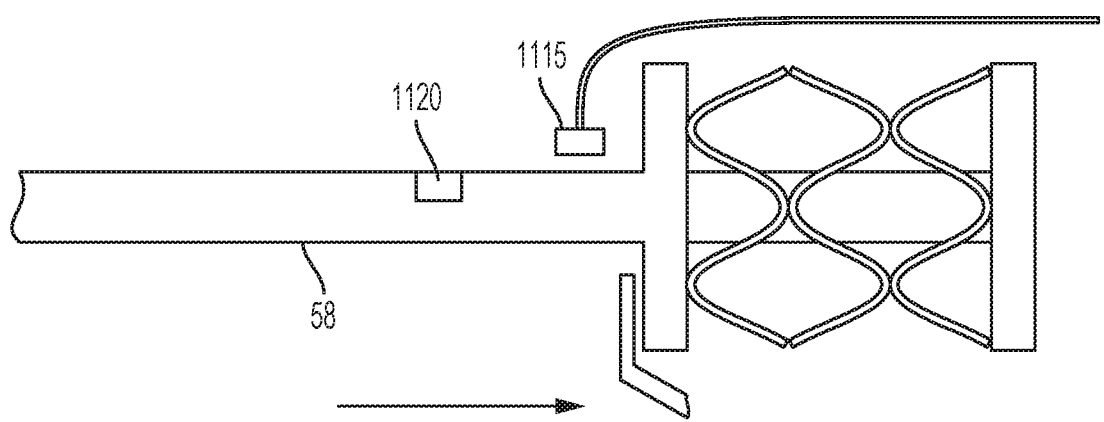
FIGS. 11A and 11B depict an aspect of a magnetic sensor configured to detect a motion of a reciprocating tube component of an ultrasonic medical device in accordance with the present disclosure.
Figure 11B:
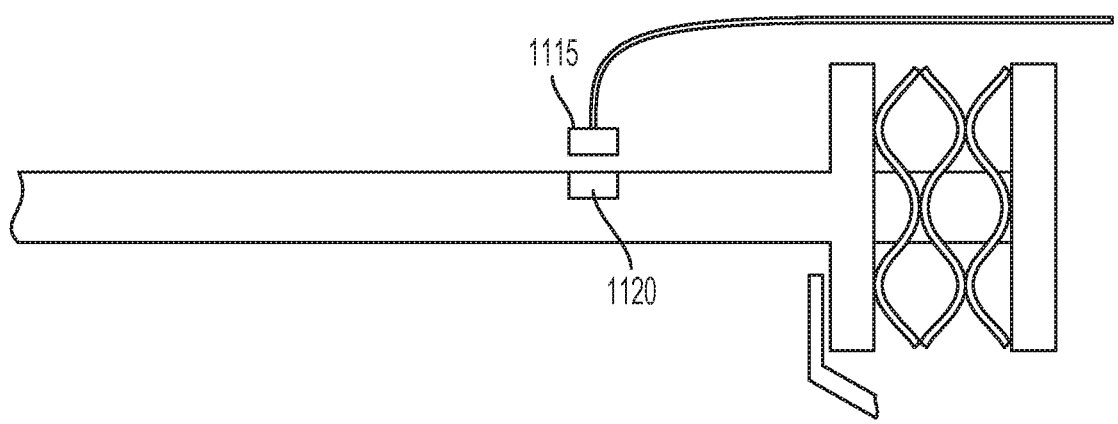

In another aspect, depicted in FIGS. 11A and 11B, the reciprocating tubular actuating member 58 may include a small tube magnet 1120. The motion and/or position of the tube magnet 1120 may be detected by a Hall Effect sensor 1115, positioned proximate to the reciprocating tubular actuating member 58 and fixed within the handle assembly 12. In another aspect, tube magnet 1120 may have north and south poles moving in a line parallel to the face of the Hall Effect sensor 1115, which may be in a fixed position.

The Hall Effect sensor 1115 may include a small electronic chip which may sense magnetic fields and change its electrical output based on the relative proximity of the tube magnet 1120 or the strength of the magnetic fields to the Hall Effect sensor 1115. The tube magnet 1120 may move across the face of the Hall Effect sensor 1115 as the reciprocating tubular actuating member 58 translates in a proximal direction (arrow, FIG. 11A). At the end of the travel of the reciprocating tubular actuating member 58, as depicted in FIG. 11B, tube magnet 1120, may be positioned directly in front of the face of the Hall Effect sensor 1115, as depicted in FIG. 11B.

As the reciprocating tubular actuating member 58 translates in the proximal direction (and the jaw changes to a closed state) as shown by the arrow in FIG. 11A, the tube magnet 1120 may be translated towards the Hall Effect sensor 1115, thereby changing the voltage output of the Hall Effect sensor 1115. It may be further understood that such a tube magnet sensing mechanism may operate in a reverse mode, in which the tube magnet 1120 may be translated away from the Hall Effect sensor 1115 when the reciprocating tubular actuating member 58 translates during jaw actuation. It may be recognized that the output of the magnetic sensing mechanism may provide a measure either of a position of the reciprocating tubular actuating member 58 or an amount of travel of the reciprocating tubular actuating member 58. Drive and detection electronics for the Hall Effect sensor 1115, including a current source and voltage measurement electronics, may be located on circuit board 553.

Figure 12A:
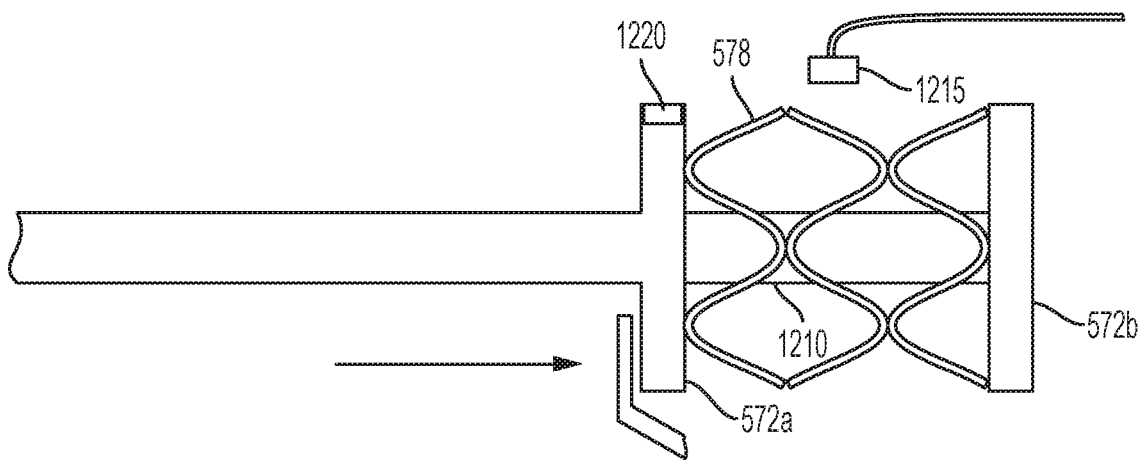
FIGS. 12A and 12B depict an aspect of a magnetic sensor configured to detect a motion of a reciprocating collar flange component of an ultrasonic medical device in accordance with the present disclosure.
Figure 12B:
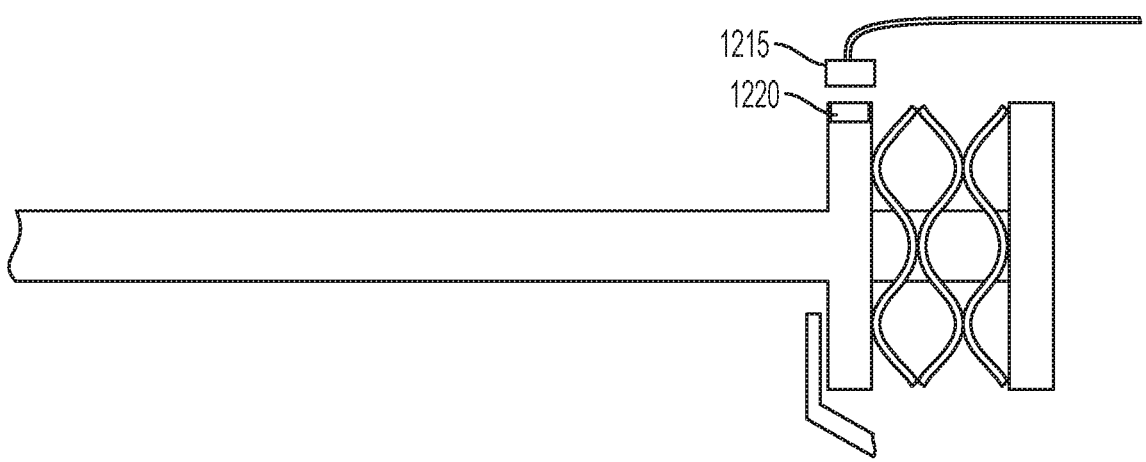
Figure 13A:
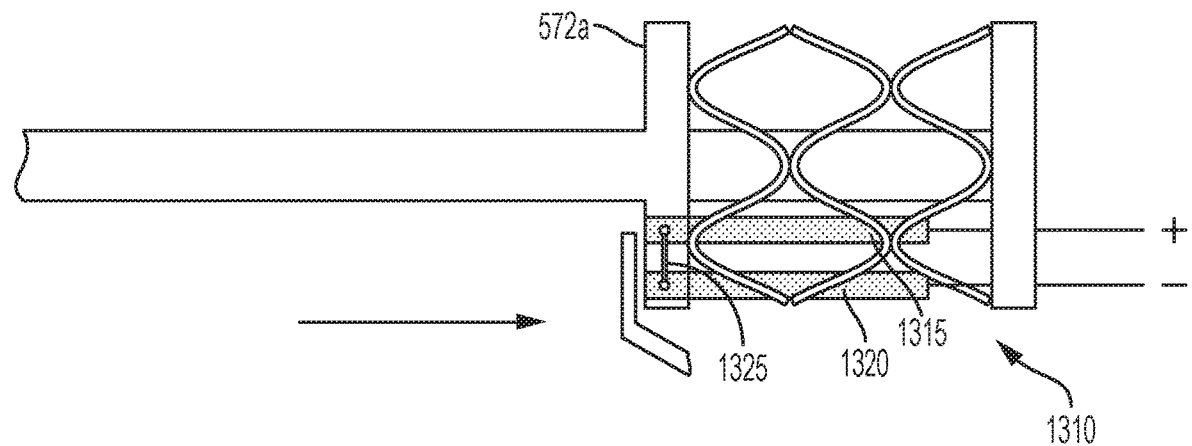
FIGS. 13A and 13B depict an aspect of an electrical resistive sensor configured to detect a motion of a reciprocating collar flange component of an ultrasonic medical device in accordance with the present disclosure.
Figure 13B:
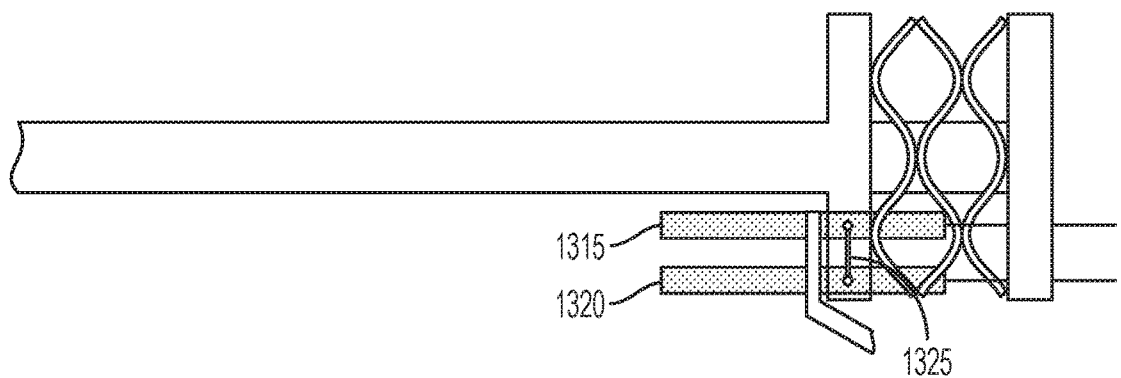
Figure 14A:
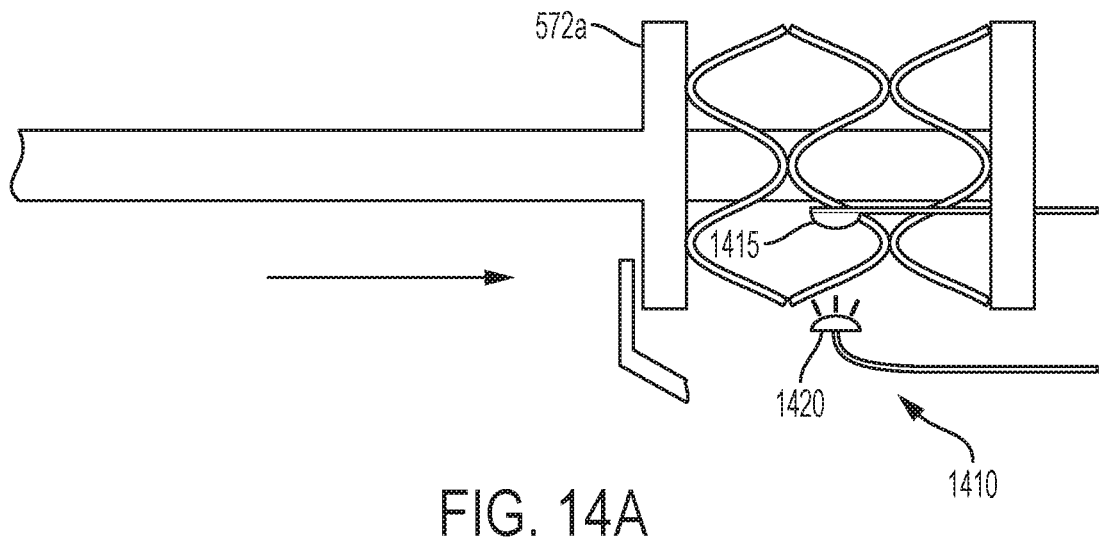
FIGS. 14A and 14B depict an aspect of an optical sensor configured to detect a motion of a reciprocating collar flange component of an ultrasonic medical device in accordance with the present disclosure.

In other aspects, depicted in FIGS. 12-14, the reciprocating tubular actuating member 58 may be mechanically coupled to a reciprocating collar 1210. The reciprocating collar 2010 may comprise a distal flange 572*a* mechanically coupled to the proximal end of the reciprocating tubular actuating member 58. The reciprocating collar 1210 may also comprise a proximal flange 572*b* mechanically coupled to a reciprocating collar body 1210 and fixed in the frame of reference of the handle assembly 12. The reciprocating collar body 1210 may be suitably disposed so that the reciprocating tubular actuating member 58 may slide over the reciprocating collar body 1210. In one alternative aspect, the reciprocating yoke 84 may engage the distal flange 572*a* and cause the distal flange 572*a*, along with the reciprocating tubular actuating member 58, to slide in a proximal direction when the trigger 32 is compressed by a user, as depicted by the arrows in FIGS. 12A, 13A, and 14A.

The spring stack 578 may be disposed around the reciprocating collar body 1210 between the distal flange 572*a* and the proximal flange 572*b*. The spring stack 578 may be compressed when the reciprocating yoke 84 translates in a proximal direction when the trigger 32 is actuated. Upon release of the trigger 32, a restoring force developed in the spring stack 578 due to its compression may cause the distal flange 572*a* and the coupled reciprocating tubular actuating member 58 to advance in a distal direction.

In one aspect, depicted in FIGS. 12A and 12B, the distal flange 572*a* may include a small flange magnet 1220. The motion and/or position of the flange magnet 1220 may be detected by a Hall Effect sensor 1215, positioned in a location proximal to the distal flange 572*a* and fixed within the handle assembly 12. In another aspect, flange magnet 1220 may have north and south poles moving in a line parallel to the face of the Hall Effect sensor 1215, which may be in a fixed position.

The Hall Effect sensor 1215 may include a small electronic chip which may sense magnetic fields and change its electrical output based on the relative proximity of the flange magnet 1220 or the strength of the magnetic fields to the Hall Effect sensor 1215. The flange magnet 1220 may move across the face of the Hall Effect sensor 1215 as the distal flange 572*a* translates in a proximal direction (arrow, FIG. 12A). At the end of the travel of the distal flange 572*a*, as depicted in FIG. 12B, flange magnet 1220, may be positioned directly in front of the face of the Hall Effect sensor 1215, as depicted in FIG. 12B.

As the distal flange 572*a* translates in the proximal direction (and the jaw changes to a closed state) as shown by the arrow in FIG. 12A, the flange magnet 1220 may be translated towards the Hall Effect sensor 1215, thereby changing the voltage output of the Hall Effect sensor 1215. It may be further understood that such a flange magnet sensing mechanism may operate in a reverse mode, in which the flange magnet 1220 may be translated away from the Hall Effect sensor 1215 when the distal flange 572*a* translates during jaw actuation. It may be recognized that the output of the magnetic sensing mechanism may provide a measure either of a position of the distal flange 572*a* or an amount of travel of the distal flange 572*a*. Drive and detection electronics for the Hall Effect sensor 1215, including a current source and voltage measurement electronics, may be located on circuit board 553.

In another aspect, as depicted in FIG. 13A,B, a position of the distal flange 572*a* may be determined by an electrical resistive sensor 1310. The resistive sensor 1310 may comprise a first linear resistive element 1315 coupled to a positive voltage (indicated by the "+" in FIG. 13A) and a second conductive element 1320 coupled to a negative voltage or an electrical ground (indicated by the "−" in FIG. 13A). In one aspect, a rim of the distal flange 572*a* may be electrically conductive and is configured to contact both the linear resistive element 1315 and the conductive element 1320. In another aspect, the distal flange 572*a* may include an electrically conductive wiper 1325 that is configured to contact both the linear resistive element 1315 and the conductive element 1320.

As the distal flange 572a translates in a proximal direction (as shown by the arrow in FIG. 13A), the conductive flange of the distal flange 572a or the wiper 1325 may move along the linear resistive element 1315. As a result, a measurement of an electrical current passing through the electrical resistive sensor 1310 when the distal flange 572a is in a distal position, as depicted in FIG. 13A, may differ from the electrical current passing through the electrical resistive sensor 1310 when the distal flange 572a is in a proximal position, as depicted in FIG. 13B. In one aspect, the current through the electrical resistive sensor 1310 may be greater when the distal flange 572a is in a distal position than when the distal flange 572a is in a proximal position. In another aspect, the current through the electrical resistive sensor 1310 may be greater when the distal flange 572a is in a proximal position than when the distal flange 572a is in a distal position. It may be understood that the position or amount of travel of the distal flange 572a may be measured by the electrical resistive sensor 1310. Drive and detection electronics for the electrical resistive sensor 1310, including a voltage source and current measurement electronics, may be located on circuit board 553.

In another aspect, as depicted in FIG. 14A,B, a position of the distal flange 572a may be determined by an optical sensor 1410. The optical sensor 1410 may comprise an optical source 1420, such as an LED and a light sensor 1415. The light sensor 1415 may be configured to produce either a current or voltage proportional to an amount of light received by the light sensor 1415 from the optical source 1420. In one aspect, the optical source 1420 and the light sensor 1415 may be disposed to permit an edge of the distal flange 572a to move therebetween.

Figure 14B:
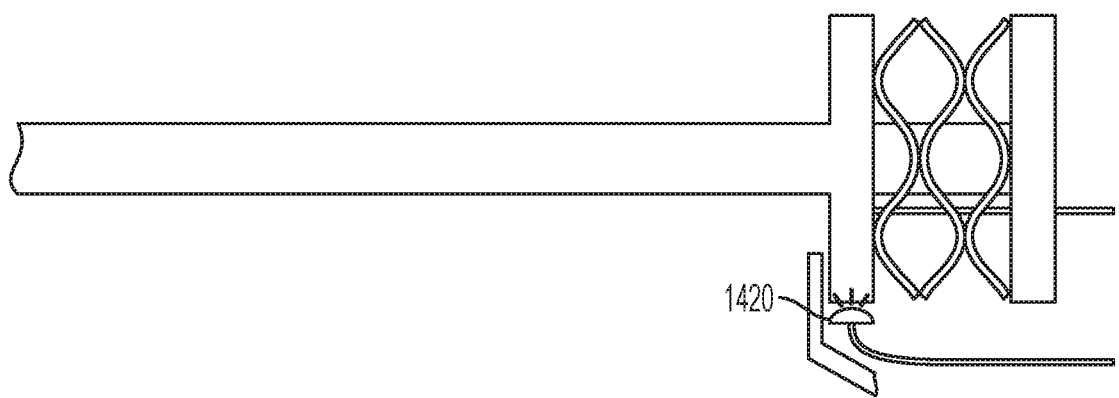

As the distal flange 572a translates in a proximal direction (as shown by the arrow in FIG. 14A), the distal flange 572a may be positioned to partially or totally occlude the light sensor 1415 from receiving the light emitted by the optical source 1420 as depicted in FIG. 14B. Note that the light sensor 1415 is not shown in FIG. 14B because the distal flange 572a is positioned between the light sensor 1415 and the optical source 1420. As a result, a measurement of an electrical voltage or current from the light sensor 1415 when the distal flange 572a is in a distal position, as depicted in FIG. 14A, may differ from the electrical voltage or current from the light sensor 1415 when the distal flange 572a is in a proximal position, as depicted in FIG. 14B. As depicted in FIG. 14A,B, the light sensor 1415 may receive illumination from the optical source 1420 when the distal flange 572a is in a distal position (FIG. 14A), and light from the optical source 1420 may be occluded from the light sensor 1415 by the distal flange 572a when the distal flange 572a is in a proximal position (FIG. 14B). However, in an alternative embodiment, the light sensor 1415 may receive illumination from the optical source 1420 when the distal flange 572a is in a proximal position, and light from the optical source 1420 may be occluded from the light sensor 1415 by the distal flange 572a when the distal flange 572a is in a distal position (FIG. 14B).

Although FIG. 14A,B depict a single optical source 1420 and a single light sensor 1415, such a sensor configuration is not limiting. For example, multiple optical sources may be disposed in a linear array along an axis parallel to the travel of the distal flange 572a. Similarly, multiple light sensors may be disposed in a linear array along an c, in which each of the multiple light sensors is configured to receive illumination from one of the linear array of optical sources. The distance traveled or position of the distal flange 572a as it transits in the proximal or distal direction may be determined from a measurement of a current or a voltage generated by each of the light sensors. In some aspects, the current or voltage may have a high value when the distal flange 572a occludes a particular light sensor. In other aspects, the current or voltage may have a low value when the distal flange 572a occludes a particular light sensor. Therefore, the position of the distal flange 572a may be determined based on which of the linear array of light sensors has the electrical characteristics corresponding to a low light level due to the position of the distal flange 572a.

In another aspect, a single optical source may illuminate multiple light sensors. As one non-limiting example, the single optical source may comprise an electroluminescent strip disposed along an axis parallel to the travel of the distal flange 572a. Drive and detection electronics for the optical sensor 1410, including a voltage source and current measurement electronics, may be located on circuit board 553.

Figure 15A:
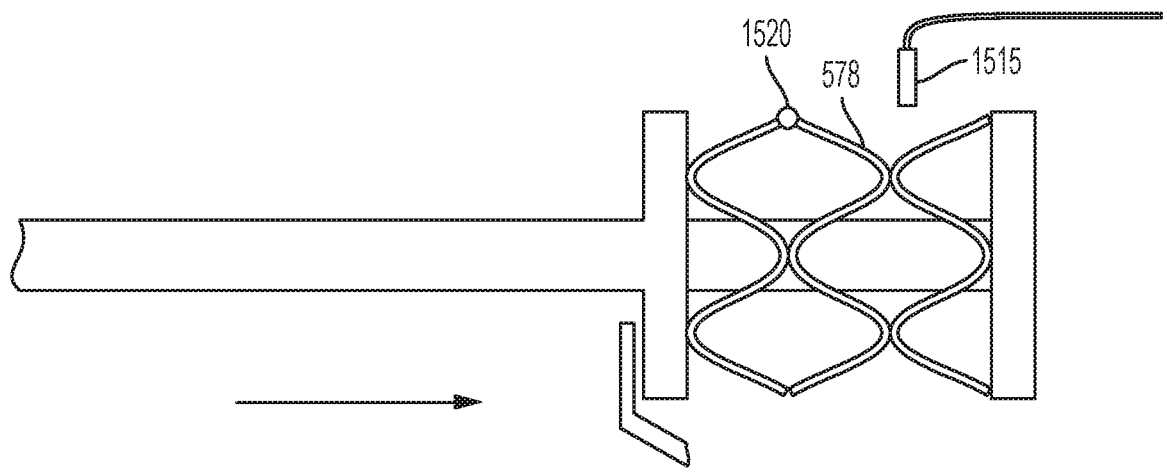
FIGS. 15A and 15B depict an aspect of a magnetic sensor configured to detect a motion of a spring stack component of an ultrasonic medical device in accordance with the present disclosure.
Figure 15B:
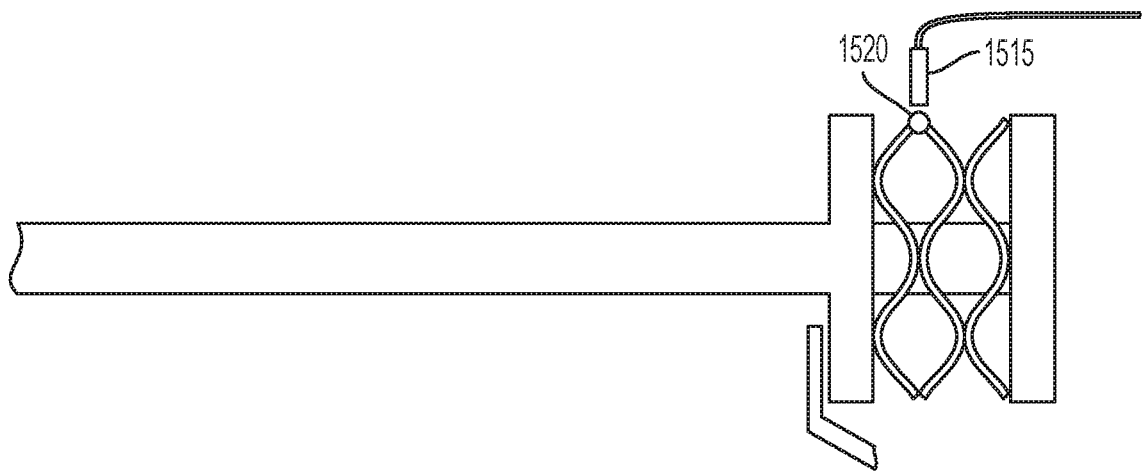

In one aspect, depicted in FIGS. 15A and 15B, the spring stack 578 may include a small spring magnet 1520 at a distal end of the spring stack 578. The motion and/or position of the spring magnet 1520 may be detected by a Hall Effect sensor 1515, positioned at a location proximal to the distal end of the spring stack 578 and fixed within the handle assembly 12. In another aspect, spring magnet 1520 may have north and south poles moving in a line parallel to the face of the Hall Effect sensor 1515, which may be in a fixed position.

The Hall Effect sensor 1515 may include a small electronic chip which may sense magnetic fields and change its electrical output based on the relative proximity of the spring magnet 1520 or the strength of the magnetic fields to the Hall Effect sensor 1515. The spring magnet 1520 may move towards the face of the Hall Effect sensor 1515 as the spring stack 578 is compressed (arrow, FIG. 15A) and the distal end of the spring stack 578 approaches the Hall Effect sensor 1515. When the spring stack 578 is at a maximal compression, the spring magnet 1520, may be positioned directly in front of the face of the Hall Effect sensor 1515, as depicted in FIG. 15B.

As the spring stack 578 is compressed in the proximal direction (and the jaw changes to a closed state) as shown by the arrow in FIG. 15A, the spring magnet 1520 may be translated towards the Hall Effect sensor 1515, thereby changing the voltage output of the Hall Effect sensor 1515. It may be further understood that such a spring magnet sensing mechanism may operate in a reverse mode, in which the spring magnet 1520 may be translated away from the Hall Effect sensor 1515 located at a distal end of the spring stack 578 when the spring stack 578 is compressed during jaw actuation. It may be recognized that the output of the magnetic sensing mechanism may provide a measure either an amount or degree of compression of the spring stack 578. Drive and detection electronics for the Hall Effect sensor 1515, including a current source and voltage measurement electronics, may be located on circuit board 553.

As depicted in FIGS. 5, and 10-15 and disclosed above, a number of sensors may be employed to measure functions of mechanical components of the medical device 10. Although specific sensors, such a piezoelectric sensors, inductive sensors, resistive sensors, optical sensors, and magnetic sensors have been explicitly disclosed, it may be recognized that any suitable sensor may be used to measure such mechanical functions. Additional sensors may also include, without limitation, capacitive sensors, magnetostrictive sensors, acoustic sensors, and strain-gauge sensors.

Such sensors may provide data related to the mechanical functions in any appropriate form including, without limitation, signal voltages, signal currents, impedances, resistances, signal frequencies, and signal phases. Such data may include analog data or digital data, or combination or combinations thereof. Further, the data provided by such sensors may refer directly to such mechanical functions or may refer indirectly to such functions. Further, the data provided by such sensors may be conditioned electronically to provide a user with measures of the mechanical functions of the components of the medical device 10. Such conditioning electronics may comprise analog components, digital components, or combination or combinations thereof. Conditioning electronics may include, without limitation, discrete components such as resistors, capacitors, and inductors. Conditioning electronics may include, without limitation, integrated circuits such as amplifiers, comparators, and filters. Conditioning electronics may further include, without limitation, digital electronic components such as ADCs, DACs, microprocessors, and capacitors, and inductors. It may be understood that conditioning electronics may include any combination or combinations of such discrete components, integrated circuits, and digital electronic components.

As noted above, the mechanical functions that may be sensed may include, without limitation, any one or more of absolute mechanical position, relative mechanical position of one component with respect to another component, mechanical motion including direction, rate, and/or acceleration of a component, mechanical deformation (such as spring compression), force applied to a component, and a force generated by a component.

In a broader sense, a mechanical function that may be sensed may include, without limitation, a mechanical integrity of a component. Measures of mechanical integrity may provide data related to component warping, chipping, crazing, pitting, cracking, or other indications of mechanical wear and/or damage that may adversely affect the intended function of a component.

In a still broader sense, a mechanical function that may be sensed may include, without limitation, the presence or absence of a component.

FIG. 16 illustrates a block diagram of one aspect of an ultrasonic medical device 100 which may include or implement many of the features described herein. For example, in an aspect, medical device 100 may be similar to or representative of ultrasonic medical device 10. The medical device 100 may include a generator 102 configured to supply an electric potential across the faces of one or more ultrasonic transducers 104. The ultrasonic medical device 100 may also include an ultrasonic end effector acoustically coupled to the ultrasonic transducers 104. The medical device 100 may also include a control system 108 that may control any of the functions of the medical device 100, for example controlling an operation of the generator 102.

The control system 108 may also provide functional feedback to a user of the medical device 100 including, without limitation, audio feedback via speakers 114 and visual feedback via one or more visual displays 116. For example, a speaker 114 may emit a signal indicative of the end effector power. According to various aspects, the speaker 114 may emit a series of pulse sounds, where the frequency of the sound pulses is indicative of the amount of power supplied to the end effector. In addition to, or instead of the speaker 114, the device may include a visual display 116. The visual display 116 may indicate end effector power according to any suitable method. For example, the visual display 116 may include a series of light emitting diodes (LEDs), where end effector power is indicated by the number of illuminated LEDs.

The control system 108 may also receive data signals from one or more sets of device electronics 109. Such device electronics 109, as disclosed above, may receive one or more types of electrical signals from any one or more of device sensors 112. Non-limiting examples of such device sensors and the electrical signals they may produce are disclosed above with respect to FIGS. 5, and 10-15. The device electronics 109 may communicate data to the control system 108 referencing a mechanical function or functions of one or more mechanical components of the medical device 100. On receipt of the device electronics data, the control system 108 may communicate with a user regarding the state of the medical device 100.

The control system 109 may comprise a processor device and one or more memory devices. The one or more memory devices may be configured to store instructions that may direct one or more functions of the processor device. In some non-limiting examples, such instructions may direct the processor device to initiate one or more pre-surgical processes in which the processor communicates with a user of the medical device 100. Such pre-surgical processes may include any step or steps carried out by the user, such as compressing a trigger of the medical device 100. Such pre-surgical processes may also comprise a step or steps carried out by the processor, such as actuating the one or more ultrasonic transducer 104. The pre-surgical processes may further include directing the processor to measure or determine one or more mechanical functions of the medical device 100 based on the electrical data produced by the device sensors 112 and communicated through the device electronics 109 to the control system 108. The control system 109, upon completion of the pre-surgical processes, may notify the user of the results of the pre-surgical processes. In some non-limiting aspects, the control system 109, upon determining from the pre-surgical processes that the medical device 100 or a component thereof is not capable of functioning properly, may prevent a user from actuating any one or more functions of the medical device 100.

In one non-limiting aspect, the device electronics 109 may be located on a circuit board (for example 553 in FIG. 5) disposed within a handle assembly of the medical device 100. 'Examples of such device electronics 109 have been disclosed above. In one aspect, such device electronics 109 may be electrically coupled to the control system 108 and may be configured to receive data signals from the device sensors 112. The device electronics 109 may then communicate data based on the signals received from the device sensors 112 to the control system 108. In an alternative aspect, as indicated by the dotted lines in FIG. 16, the device electronics 109 may be incorporated in the control system 108. In some aspects, the control system 108 may be located within the handle assembly of the medical device 100. In alternative aspects, the control system 108 may be incorporated in a device separate from the medical handle assembly, such as in a separate housing. The separate housing may further include the generator.

As disclosed above, an ultrasonic medical device may comprise a variety of mechanical and electrical components that may fowl, wear, and/or break over time as a result of the intended use of the medical device. In some circumstances, it may be desirable to send the medical device back to its original manufacturer or to a third party authorized by the manufacturer for cleaning, repair, or replacement of the fowled, worn, or broken components. In some alternative circumstances, it may be desirable to have personnel at a user's facility perform the cleaning, repair, and/or replacement of the components of the medical device. It may be recognized that the personnel at the user's facility may not have expertise in the disassembly and reassembly of the medical device, which may be required to affect the cleaning, repair, or replacement of the components. As a result, a reassembled medical device may not function properly during use.

As disclosed above, an ultrasonic medical device may be fabricated to include features to test the functional integrity of various components of the reassembled medical device and to notify the user if the device does not function properly after reassembly. Such features may comprise one or more sensors (including sensor-related electronics) configured to measure one or more of the functions of the mechanical components of the medical device. As disclosed above, examples of such mechanical components may include, without limitation, an ultrasonic blade, a jaw assembly, a reciprocating tubular actuating member configured to actuate the jaw assembly, a waveguide, and one or more components configured to permit a user to actuate the reciprocating tubular actuating member. As disclosed above, a number of sensors may be incorporated in the medical device to measure and/or sense the function or functions of such mechanical components.

Additional features of the medical device configured to determine if the device does not function properly after reassembly may include one or more sets of instructions to be executed by a processor located in the medical device. The instructions may embody one or more methods to test the medical device for proper reassembly and component function. Such instructions may further notify the user of the outcome of such tests, including recommendations to address detected faults or anomalies in reassembly. Such instructions may be encoded in any suitable manner for execution by a computing processor. The computing processor may be incorporated in a control module configured to control the operation or operations of the medical device. The computing processor may be incorporated in a component such as a circuit board located in the handle of the medical device. The instructions may be stored in a non-volatile memory component accessible to the computing processor. Such memory components may include, without limitation, one or more of a PROM, a ROM, an EPROM, an EEPROM, and a flash memory. In some aspects, a medical device may include multiple computing processors any or all of which may execute one or more of the instructions that may encode one or more methods to test the medical device for proper reassembly and component functioning. These methods may be incorporated in one or more pre-surgical processes to test the functional integrity of the medical device prior to medical use.

The methods may include, without limitation, an instruction to a user to manipulate one or more controls of the device, an instruction for the processor device to receive data from a sensor, and an instruction for the processor to compare the received sensor data with one or more acceptance reference values. Depending on the result of the comparison of the received sensor data with the acceptance reference values, the processor may execute additional instructions to notify the user that the instrument is acceptable for use or that the instrument is not acceptable for use. If the processor executes instructions to notify the user that the instrument is not acceptable for use, the processor may additionally execute instructions to notify the user to reassemble the device again, or to send the device back to the manufacturer, or to a facility authorized by the manufacture, for additional cleaning, part repair, or part replacement.

For the purposes of the methods disclosed herein, an acceptance reference value or group of acceptance reference values may be a value or range of values (for example, as expressed as the endpoints of the range of values) indicative of acceptable values associated with a function tested by a method. In some non-limiting aspects, such acceptance reference values may represent an acceptable position of a component, an acceptable range of motion of a component, an acceptable direction of motion of a component, an acceptable measured voltage, current, impedance, frequency or phase of an electrically actuated component, or an acceptable force or pressure exerted on or by a component.

The acceptance reference value or values may be calculated values. The acceptance reference value or values may be values derived from measurements of the components during fabrication and/or initial assembly of the medical device. The one or more acceptance reference value or values may be encoded or stored in a non-volatile memory electronic component disposed within the ultrasonic medical device. The one or more acceptance reference value or values may be encoded or stored in a non-volatile memory electronic component disposed within the ultrasonic medical device during device manufacture by a manufacturer or by a third party suitably authorized by the manufacturer during a repair procedure. The non-volatile memory component may comprise, without limitation, a ROM, an EPROM, an EEPROM, a flash memory, or any other electronic component configured to retain data. The non-volatile memory component may be physically disposed in any suitable portion of the medical device, for example in a control circuit, a generator, or in one or more circuit boards (for example, circuit board 553 in FIG. 5) that may be disposed within the handle assembly 12.

Disclosed below are examples of processes, procedures, and/or methods by which a medical device may be tested for acceptable use for a medical procedure. Although such processes, procedures, and/or methods may be intended for use prior to the performance of a medical procedure, it may be recognized that at least some of the processes, procedures, and/or methods may be used during a hiatus of the medical procedure in order to re-assess the suitability of the medical device for continued use.

Such processes, procedures, and/or methods may be included in one or more self-test procedures or burn-in procedures as may be appropriate. For the purpose of simplifying the descriptions disclosed below, the processes, procedures, and/or methods may all be referred to generally as "methods for testing a medical device." Although the descriptions of components with respect to the methods for testing a medical device may be particularly associated with an ultrasonic medical device such as depicted in FIGS. 1-9, it may be understood that such methods may also be applicable to testing medical devices that do not include one or more of the specifically named components. It may be further understood that such methods may also be applicable to testing medical devices that include mechanically or functionally similar components as those disclosed above with an ultrasonic medical device such as depicted in FIGS. 1-9.

Even if not explicitly described below, the methods may all be initiated by a user forming an appropriate electrical connection between a reassembled ultrasonic medical device and a control system or control module configured to control the operation of the medical device, for example as disclosed above with reference to FIG. 16.

One aspect of a method for testing a medical device may include a method for determining if all of the components of the medical device have been included during reassembly. For example, it may be possible for a user to reassemble a medical device 10 and omit the protective sheath 80 that may isolate the user from the mechanical vibrations induced in the waveguide and/or ultrasonic blade. If a user attempts to use the device without the protective sheath 80, the user may experience vibrations that may distract the user from properly performing the medical procedure.

In one aspect, a method of testing a medical device for the omission of a protective sheath 80 may be based on a measured impedance of the piezoelectric transducers (for example 616 In FIG. 6 or 912*a,b* in FIG. 7).

Without being bound by theory, it may be recognized that the electromechanical coupling factor of a piezoelectric transducer may be related to the ratio of the stored mechanical energy to the input electrical energy of the transducer. Therefore, changes in the mechanical components acoustically coupled to the piezoelectric transducers (which may be considered the acoustic or mechanical load on the transducers) may have an effect on the coupling factor through changes in the stored mechanical energy. The protective sheath 80 may dampen the vibrations induced in the waveguide (for example 678 of FIG. 6 and 378 of FIG. 7). In order for the protective sheath 80 to dampen the vibrations in the waveguide, the protective sheath 80 may be acoustically coupled to the waveguide. Because the waveguide is acoustically coupled to the piezoelectric transducers, the protective sheath 80, in turn, may be acoustically coupled to the piezoelectric transducer. Therefore, the presence or absence of the protective sheath upon reassembly of the ultrasonic medical device may be detected as a change in the coupling factor of the piezoelectric transducer.

Again, without being bound by theory, the coupling factor may also be related to the resonance and anti-resonance frequencies of the piezoelectric transducer. It may additionally be understood that the impedance of the piezoelectric transducer may be a function of the resonance and anti-resonance frequencies. Thus, a change in a measured impedance of a piezoelectric transducer may reflect a change in the coupling factor of the piezoelectric transducer. It may therefore be recognized that an omission of the protective sheath 80 during reassembly of the medical device may result in a change in the measured impedance of the piezoelectric transducer due to the change in the coupling factor.

In one aspect, an electrical impedance may be calculated as a ratio of a voltage measured across the piezoelectric transducers to the current supplied to the piezoelectric transducers by the ultrasonic generator for example at a nominal resonance frequency under constant current conditions. In some aspects, a circuit board (for example 553 of FIG. 5) may incorporate device electronics configured to measure either the voltage, the current, or both voltage and current of the piezoelectric transducers. The electronics may also calculate the impedance from the current and voltage measurements. Alternatively, the circuit board may include electronics configured to transmit any one or more of the voltage, the current, and the calculated impedance to the ultrasonic signal generator 21 and/or the generator controller 25.

Figure 17A:
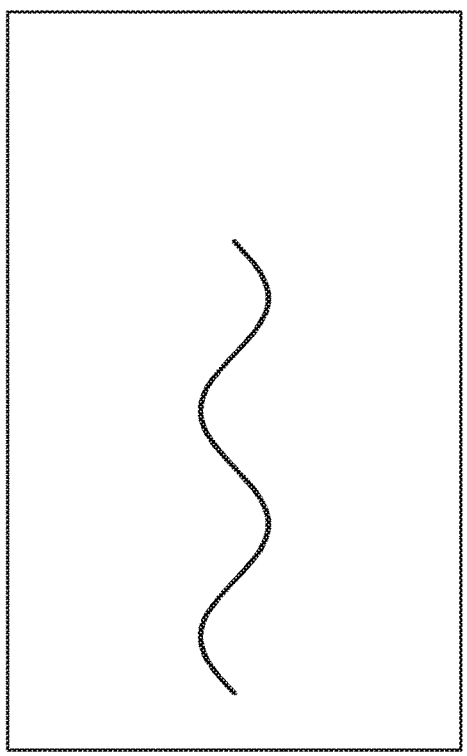
FIGS. 17A and 17B depict, respectively, graphs of applied current to and measured voltage of, a piezoelectric transducer of an ultrasonic medical device having a vibration damping membrane in accordance with the present disclosure.
Figure 17B:
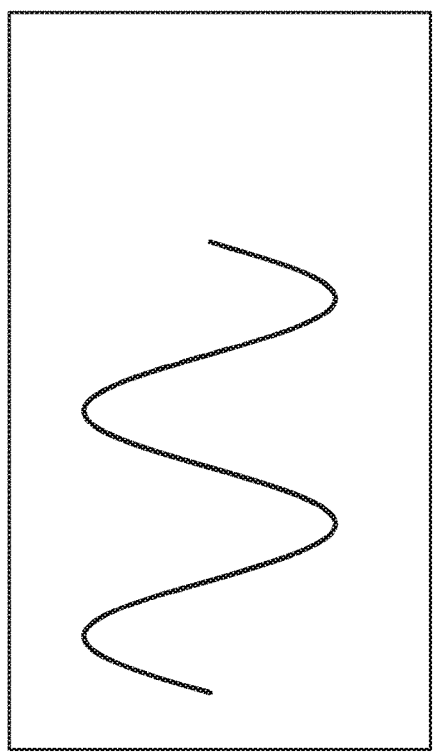
Figure 17C:
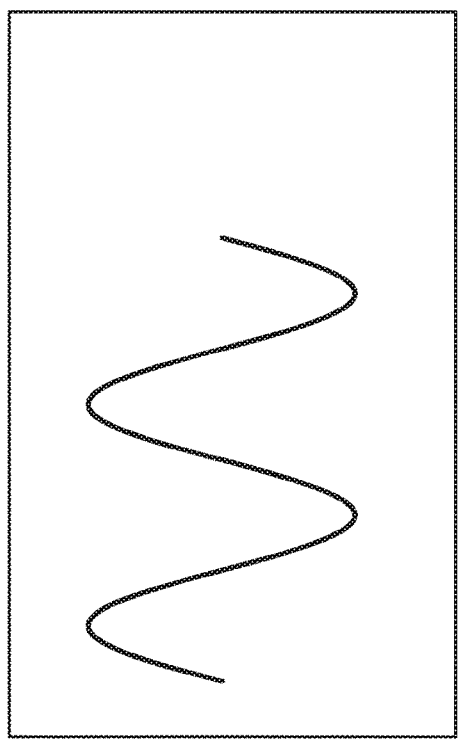
FIGS. 17C and 17D depict, respectively, graphs of applied current to and measured voltage of, a piezoelectric transducer of an ultrasonic medical device lacking a vibration damping membrane in accordance with the present disclosure.
Figure 17D:
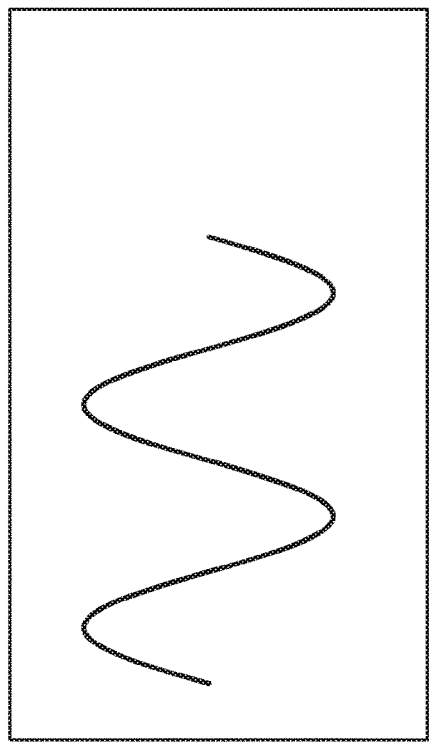

FIGS. 17A-17D depict exemplary voltage and current graphs that may be measured from a piezoelectric transducer. FIGS. 17A and 17B depict a current versus time and a voltage versus time plot, respectively, that may be obtained from a piezoelectric transducer for a reassembled medical device in which the protective sheath 80 has been properly included during reassembly. FIGS. 17C and 17D depict a current versus time and a voltage versus time plot, respectively, that may be obtained from a piezoelectric transducer for a reassembled medical device in which the protective sheath 80 has been omitted during reassembly. It may be recognized that the protective sheath, by providing mechanical damping of the vibrations of a waveguide, may reduce the measured voltage across the piezoelectric transducer due to its ability to absorb the mechanical energy through the waveguide.

Figure 18A:
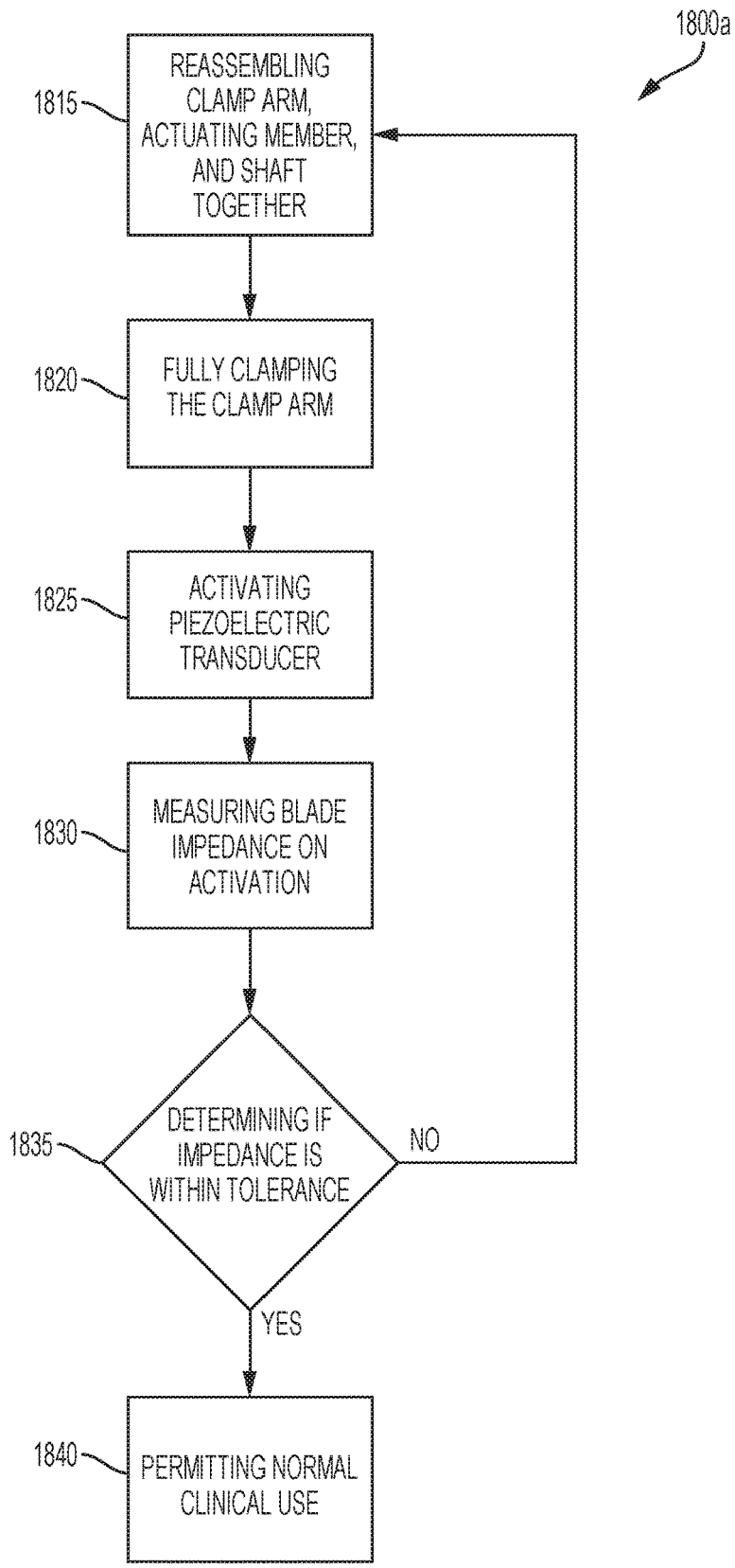
FIG. 18A is a flow chart for a method of determining if a re-assembled clamp arm, extender, and a shaft assembly are within a predetermined tolerance limit based on a piezoelectric transducer impedance value in accordance with the present disclosure.

FIG. 18A is a flow chart depicting a method 1800*a* in which a user may be alerted if a medical device is not properly reassembled based on an impedance measurement of the piezoelectric transducer. A user of the medical device may have disassembled all or part of the medical device in order to provide any type of maintenance including, without limitation, cleaning, sterilizing, replacing, and/or repairing one or more components. The user may then reassemble 1815 the medical device including, without limitation, reassembling a clamp arm, a jaw assembly, a reciprocating tubular actuating member, and a shaft assembly.

After the user forms an appropriate electrical connection between a reassembled ultrasonic medical device and a control system, the control system may prompt the user to depress the trigger fully, thereby clamping 1820 the jaw assembly proximal to the ultrasonic knife. Upon receiving an indication that the jaw assembly is clamped, for example from an output of a trigger sensor, the control system may then activate 1825 the piezoelectric transducer by allowing the generator to supply a current to the piezoelectric transducer. It may be understood that the amount of current supplied to the piezoelectric transducer during the test method may be less than that typically supplied during a medical procedure. In one example, the piezoelectric transducer may induce a transverse mechanical wave into the waveguide. In another example, the piezoelectric transducer may induce a non-transverse mechanical wave into the waveguide. The current may be applied for a predetermined amount of time during the test.

While the generator supplies the activating current to the piezoelectric transducer, one or more electrical components of the medical device, may measure 1830 an impedance of the piezoelectric transducer. It may be understood that such electronics configured to measure the impedance value may be disposed in the medical device handle assembly, the control circuit, or the generator. The electrical components and/or the control system or module may then determine 1835 if the measured impedance value is within a predetermined tolerance limit. If the measured impedance value is within the predetermined tolerance limit, then the control circuit may provide a signal to the user permitting 1840 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

If the measured impedance value is not within the predetermined tolerance limit, then the control circuit may provide a signal to the user to disassemble and reassemble the medical device. Such a signal may include an audio signal or a visual signal. A visual signal may include a text display. In one aspect, the text display may request the user to disassemble and reassemble the device. In another aspect, the text display may suggest that the user check for misaligned or missing components. In one example of this aspect, the display may suggest that the user check to assure that the protective sheath has been included in the reassembly.

Figure 18B:
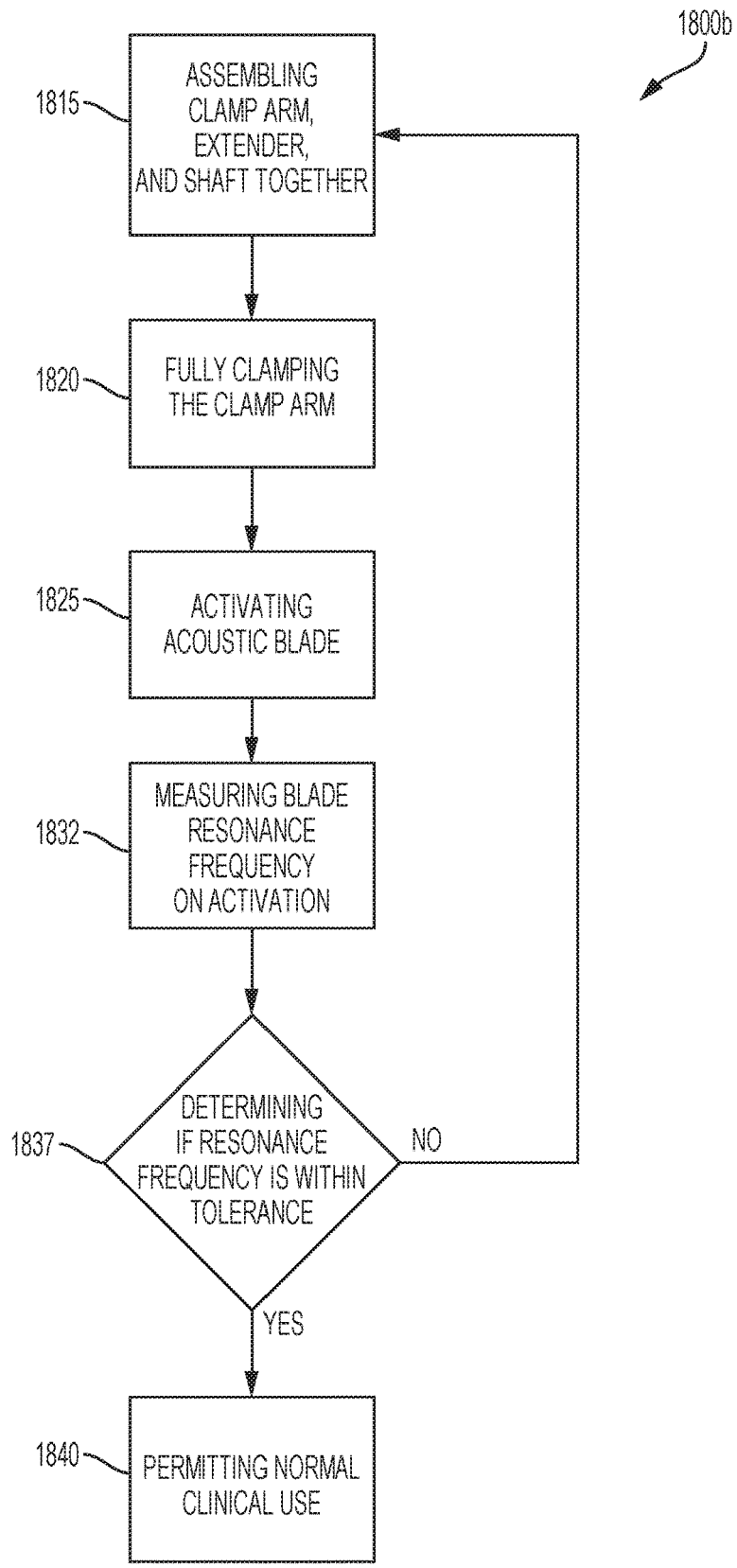
FIG. 18B is a flow chart for a method of determining if a re-assembled clamp arm, extender, and a shaft assembly are within a predetermined tolerance limit based on a piezoelectric transducer resonance frequency value in accordance with the present disclosure.

FIG. 18B is a flow chart depicting a method 1800*b* in which a user may be alerted if a medical device is not properly reassembled based on a measurement of the resonant frequency of the piezoelectric transducer. A user of the medical device may have disassembled all or part of the medical device in order to provide any type of maintenance including, without limitation, cleaning, sterilizing, replacing, and/or repairing one or more components. The user may then reassemble 1815 the medical device including, without limitation, reassembling a clamp arm, a jaw assembly, a reciprocating tubular actuating member, and a shaft assembly.

After the user forms an appropriate electrical connection between a reassembled ultrasonic medical device and a control system, the control system may prompt the user to depress the trigger fully, thereby clamping 1820 the jaw assembly proximal to the ultrasonic knife. Upon receiving an indication that the jaw assembly is clamped, for example from an output of a trigger sensor, the control system may then activate 1825 the piezoelectric transducer by allowing the generator to supply a current to the piezoelectric transducer. It may be understood that the amount of current supplied to the piezoelectric transducer during the test method may be less than that typically supplied during a medical procedure. In one example, the piezoelectric transducer may induce a transverse mechanical wave into the waveguide. In another example, the piezoelectric transducer may induce a non-transverse mechanical wave into the waveguide. The current may be applied for a predetermined amount of time during the test.

While the generator supplies the activating current to the piezoelectric transducer, one or more electrical components of the medical device, may measure 1832 a resonant frequency of the piezoelectric transducer. It may be understood that such electronics configured to measure the resonant frequency may be disposed in the medical device handle assembly, the control circuit, or the generator. For example, the control circuit may include instructions to direct the generator to produce a frequency sweep of current supplied to the piezoelectric transducer while additional electrical components measure an impedance value of the piezoelectric transducer during the frequency sweep. It may be understood that the resonant frequency may correspond to a frequency at which the impedance value is at a minimum. The electrical components and/or the control system or module may then determine 1837 if the resonant frequency is within a predetermined tolerance limit. If the resonant frequency is within the predetermined tolerance limit, then the control circuit may provide a signal to the user permitting 1840 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

If the resonant frequency is not within the predetermined tolerance limit, then the control circuit may provide a signal to the user to disassemble and reassemble the medical device. Such a signal may include an audio signal or a visual signal. A visual signal may include a text display. In one aspect, the text display may request the user to disassemble and reassemble the device. In another aspect, the text display may suggest that the user check for misaligned or missing components. In one example of this aspect, the display may suggest that the user check to assure that the waveguide is properly coupled to the piezoelectric transducer assembly. In another example of this aspect, the display may suggest that the user check to assure that the ultrasonic blade is properly coupled to the waveguide. In yet another example of this aspect, the display may suggest that the user check to assure that the ultrasonic blade is properly spaced with respect to the clamp pad.

It may be recognized that the piezoelectric transducer impedance and the piezoelectric transducer resonant frequency may be measured together during the same test procedure.

Figure 19:
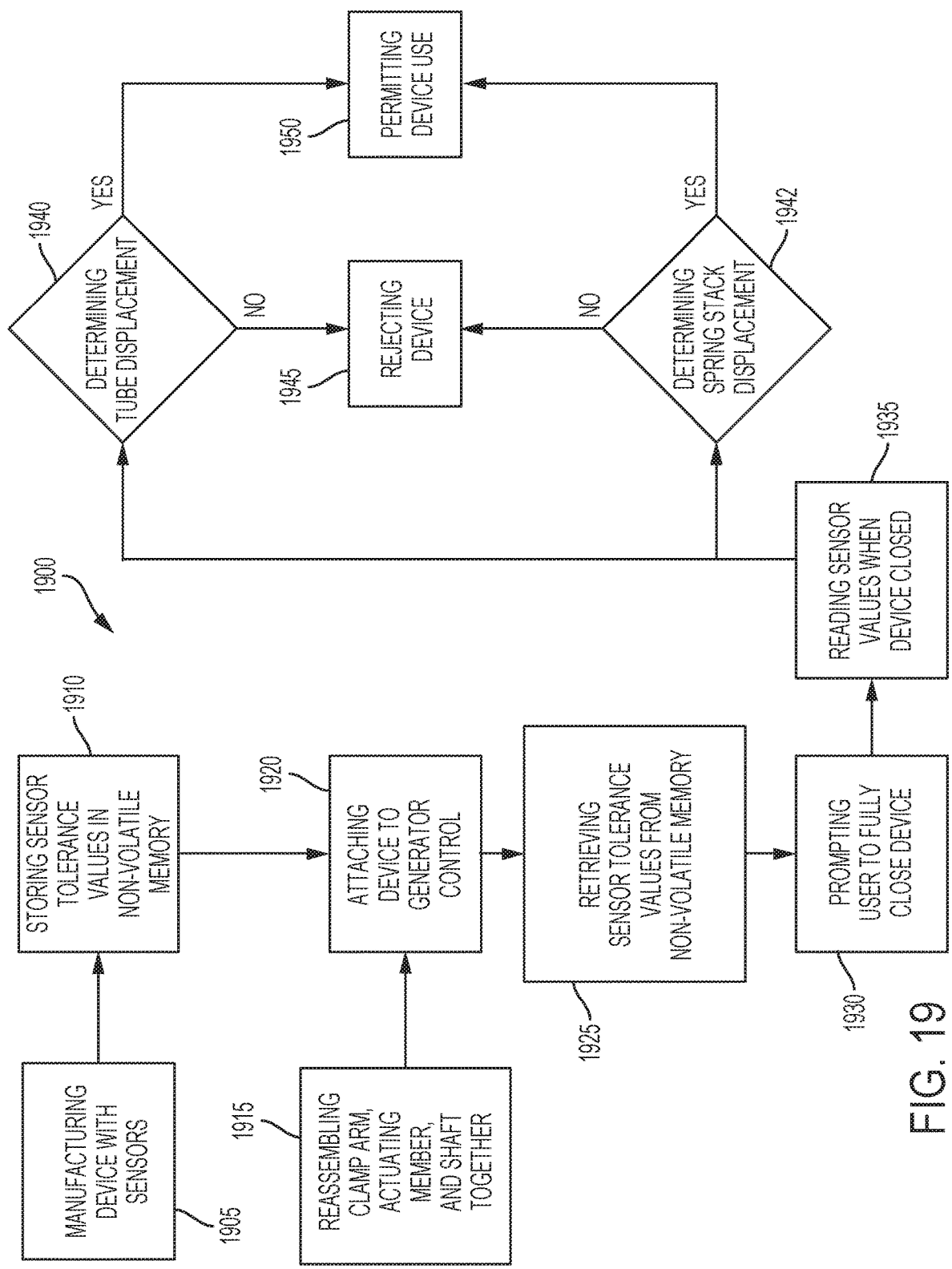
FIG. 19 is a flow chart for a method of determining if a tube displacement and a spring stack displacement are within a predetermined tolerance limit in accordance with the present disclosure.

FIG. 19 is a flow chart depicting a method 1900 in which a user may be alerted if a medical device is not properly reassembled based on data received from a sensor of a mechanical motion of one or more components of the medical device. As disclosed above, an ultrasonic medical device may be manufactured 1905 to incorporate any of a number of sensors configured to measure or detect motions of one or more mechanical components of the medical device. During the manufacture of the device, for example as part of validation and/or verification processes, the manufacturer may store 1910 one or more tolerance limit values in one or more non-volatile memory components. The one or more tolerance limit values may represent values received from one or more of the sensors and may be indicative of correct functioning of one or more of the mechanical components based on the sensor values. The values for correct functioning may include, without limitation, correct mechanical travel, correct mechanical position, and correct applied mechanical pressure. It may be understood that tolerance limit values may also be programmed into the non-volatile memory devices by a repair facility authorized by the manufacturer. The user may then receive the new or refurbished medical device from either the manufacturer or from the authorized facility.

A user of the medical device may have disassembled all or part of the medical device in order to provide any type of maintenance including, without limitation, cleaning, sterilizing, replacing, and/or repairing one or more components. The user may then reassemble 1915 the medical device including, without limitation, reassembling a clamp arm, a jaw assembly, a reciprocating tubular actuating member, and a shaft assembly. Thereafter, before clinical use, the user may attach 1920 the medical device to a control system and/or a device generator. In this manner, the user may form an appropriate electrical connection between a reassembled ultrasonic medical device and a control system. As part of a test method, the control system may retrieve 1925 one or more tolerance limit values from the non-volatile memory.

The control system may prompt 1930 the user to depress the trigger fully, thereby clamping the jaw assembly proximal to the ultrasonic knife. In one aspect, upon receiving an indication that the jaw assembly is clamped, for example from an output of a trigger sensor, the control system may then activate the piezoelectric transducer by allowing the generator to supply a current to the piezoelectric transducer. It may be understood that the amount of current supplied to the piezoelectric transducer during the test method may be less than that typically supplied during a medical procedure. In one example, the piezoelectric transducer may induce a transverse mechanical wave into the waveguide. In another example, the piezoelectric transducer may induce a non-transverse mechanical wave into the waveguide. The current may be applied for a predetermined amount of time during the test.

In another aspect, the control system may not activate the piezoelectric transducer upon receiving an indication that the jaw assembly is clamped, for example from an output of a trigger sensor as part of this test method.

The one or more electrical components of the medical device may measure 1935 one or more values obtained from the one or more sensors. It may be understood that such sensor electronics may be disposed in the medical device handle assembly, the control circuit, or the generator. The sensors may be configured to measure values for correct component functioning which may include, without limitation, correct mechanical travel, correct mechanical position, and correct applied mechanical pressure. In one non-limiting example, the sensors may measure a displacement of the reciprocating tubular actuating member. In another non-limiting example, the sensors may measure a displacement of the spring stack. As disclosed above, such sensors may include, without limitation, an inductive sensor, a resistive sensor, a magnetic sensor, or an optical sensor.

The electrical components and/or the control system or module may then determine 1940 if the measured displacement or position of the reciprocating tubular actuating member is within a predetermined tolerance limit. Alternatively, the electrical components and/or the control system or module may then determine 1942 if the measured displacement or position of the spring stack is within a predetermined tolerance limit. If the measured displacement or position of the reciprocating tubular actuating member or the measured displacement or position of the spring stack is within the predetermined tolerance limit, then the control circuit may provide a signal to the user permitting 1950 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

If the measured displacement or position of the reciprocating tubular actuating member or the measured displacement or position of the spring stack is not within the predetermined tolerance limit, then the control circuit may provide a signal to the user rejecting 1945 the device for clinical use. The control circuit may further provide a signal to the user recommending that the device should be disassembled and reassembled. Such a signal may include an audio signal or a visual signal. A visual signal may include a text display. In one aspect, the text display may request the user to disassemble and reassemble the device. In another aspect, the text display may suggest that the user check for misaligned or missing components, such as the spring stack and/or the reciprocating tubular actuating member.

Figure 20:
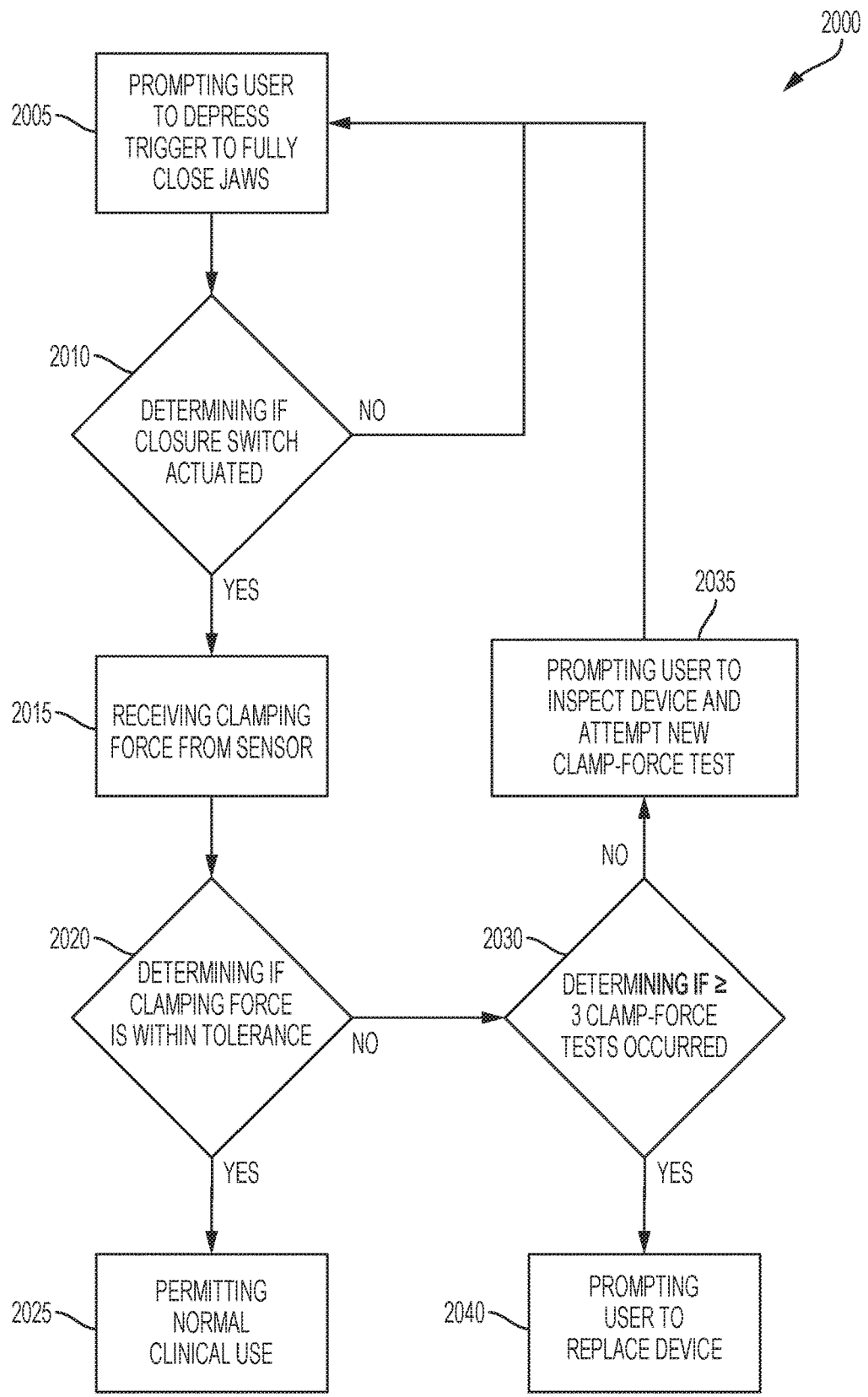
FIG. 20 is a flow chart for a method of determining if a clamping force of a jaw assembly is within a predetermined tolerance limit in accordance with the present disclosure.

FIG. 20 is a flow chart depicting a method 2000 in which a user may be alerted if a medical device is not properly reassembled based on data received from a sensor of a mechanical pressure of one or more components of the medical device. As disclosed above, an ultrasonic medical device may be manufactured to incorporate any of a number of sensors configured to measure or detect motions of one or more mechanical components of the medical device. During the manufacture of the device, for example as part of validation and/or verification processes, the manufacturer may store one or more tolerance limit values in one or more non-volatile memory components. The one or more tolerance limit values may represent values received from one or more of the sensors and may be indicative of correct functioning of one or more of the mechanical components based on the sensor values. The values for correct functioning may include, without limitation, correct mechanical travel, correct mechanical position, and correct applied mechanical pressure. It may be understood that tolerance limit values may also be programmed into the non-volatile memory devices by a repair facility authorized by the manufacturer. The user may then receive the new or refurbished medical device from either the manufacturer or from the authorized facility.

A user of the medical device may have disassembled all or part of the medical device in order to provide any type of maintenance including, without limitation, cleaning, sterilizing, replacing, and/or repairing one or more components. The user may then reassemble the medical device including, without limitation, reassembling a clamp arm, a jaw assembly, a reciprocating tubular actuating member, or any one or more components of a trigger assembly linkage (for example 590 in FIG. 5). Thereafter, before clinical use, the user may attach the medical device to a control system and/or a device generator. In this manner, the user may form an appropriate electrical connection between a reassembled ultrasonic medical device and a control system. As part of a test method, the control system may retrieve one or more tolerance limit values from the non-volatile memory.

The control system may prompt 2005 the user to depress the trigger fully, thereby clamping the jaw assembly proximal to the ultrasonic knife. The control system may then receive sensor data from a trigger sensor (for example, 532 in FIG. 5) configured to measure a position of the trigger or determine if the trigger is fully compressed. The control system may then determine 2010 if the trigger is fully compressed based on a value provided by the trigger sensor. If the trigger sensor indicates that the trigger is not fully compressed, the control system may again prompt 2005 the user to depress the trigger fully.

If the trigger sensor indicates that the trigger is fully compressed, the control system may then receive 2015 data from a force sensor referencing the clamping force of the jaw assembly against the ultrasonic knife. In one non-limiting example, the clamping force may be determined based on a voltage developed between the faces of a piezoelectric spring force sensor. In a non-limiting aspect, the piezoelectric spring force sensor may comprise a piezoelectric disk 575 disposed between the yoke 84 and the spring stack 578 (see, for example, FIG. 5). The voltage between the faces of the piezoelectric spring force sensor may be developed due to a compression of the piezoelectric spring force sensor.

The clamping force of the jaw assembly against the ultrasonic knife may be directly related to the force imparted by the motion of the reciprocating tubular actuating member (see, for example 58 in FIG. 4). The force due to the motion of the reciprocating tubular actuating member may, in turn, result from the motion of the yoke assembly (see, for example, 84 in FIG. 5). The yoke assembly may apply a compressive force to the piezoelectric disk disposed between the yoke and the spring stack due to the force exerted by a user depressing the trigger 32 through the action of the trigger assembly linkage (see, for example, 590 in FIG. 5). Thus, it may be understood that the clamp force of the jaw assembly against the ultrasonic knife may be sensed indirectly by a compressive force applied to the piezoelectric disk.

As disclosed above, during the manufacture of the device, for example as part of validation and/or verification processes, the manufacturer may store one or more tolerance limit values in one or more non-volatile memory components. The one or more tolerance limit values may represent values of a mathematical model relating the voltage developed between the faces of the piezoelectric spring force sensor and a pressure applied to the piezoelectric spring force sensor. Such a mathematical model may then relate the voltage developed between the faces of the piezoelectric spring force sensor and the clamping force of the jaw assembly.

The electrical components and/or the control system or module may then determine 2020 if the clamping force is within a predetermined tolerance limit. If the measured clamping force is within the predetermined tolerance limit, then the control circuit may provide a signal to the user permitting 2025 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

The measurement of the clamping force may be made over a period of time. It may be recognized that the measurement of the clamping force may be made while the user is depressing the trigger, and that the user may not consistently depress the trigger during the measurement. The user's fingers may flex and/or relax during the measurement, and therefore the measured clamping force may reflect the user's ability to depress the trigger with the same amount of force during the measurement. Consequently, if the control system determines 2020 that the clamping force is not within the predetermined tolerance limit, such a determination may be due to the user's inability to maintain consistent clamp force throughout the measurement time. For this test measurement, the control system may be programmed to prompt 2005 the user a predetermined number of times to depress the trigger during the test. In one non-limiting example, the predetermined number of times the user is prompted 2005 to depress the trigger may comprise three times. In other non-limiting examples, the predetermined number of times the user is prompted 2005 to depress the trigger may include one time, two times, three times, four times, five time, or any number of times as may be determined to be applicable.

In the aspect depicted in FIG. 20, the control system may determine 2030 if the user has attempted to depress the trigger for three force measurement tests. If the user has depressed the trigger fewer than three times, the user may be prompted 2035 to inspect the device and attempt a new clamp test. However, if the measured clamping force is not within the predetermined tolerance limit even after the predetermined number of force tests (for example, three clamp tests), then the control circuit may provide a signal to the user rejecting the device for clinical use. For example, the control signal may prompt 2040 the user to replace the device. Alternatively, the control signal may prompt the user to disassemble and reassemble the device. In another alternative, the control signal may prompt the user to send the device to a facility authorized by the manufacturer for additional testing, replacement, and/or repair.

Figure 21:
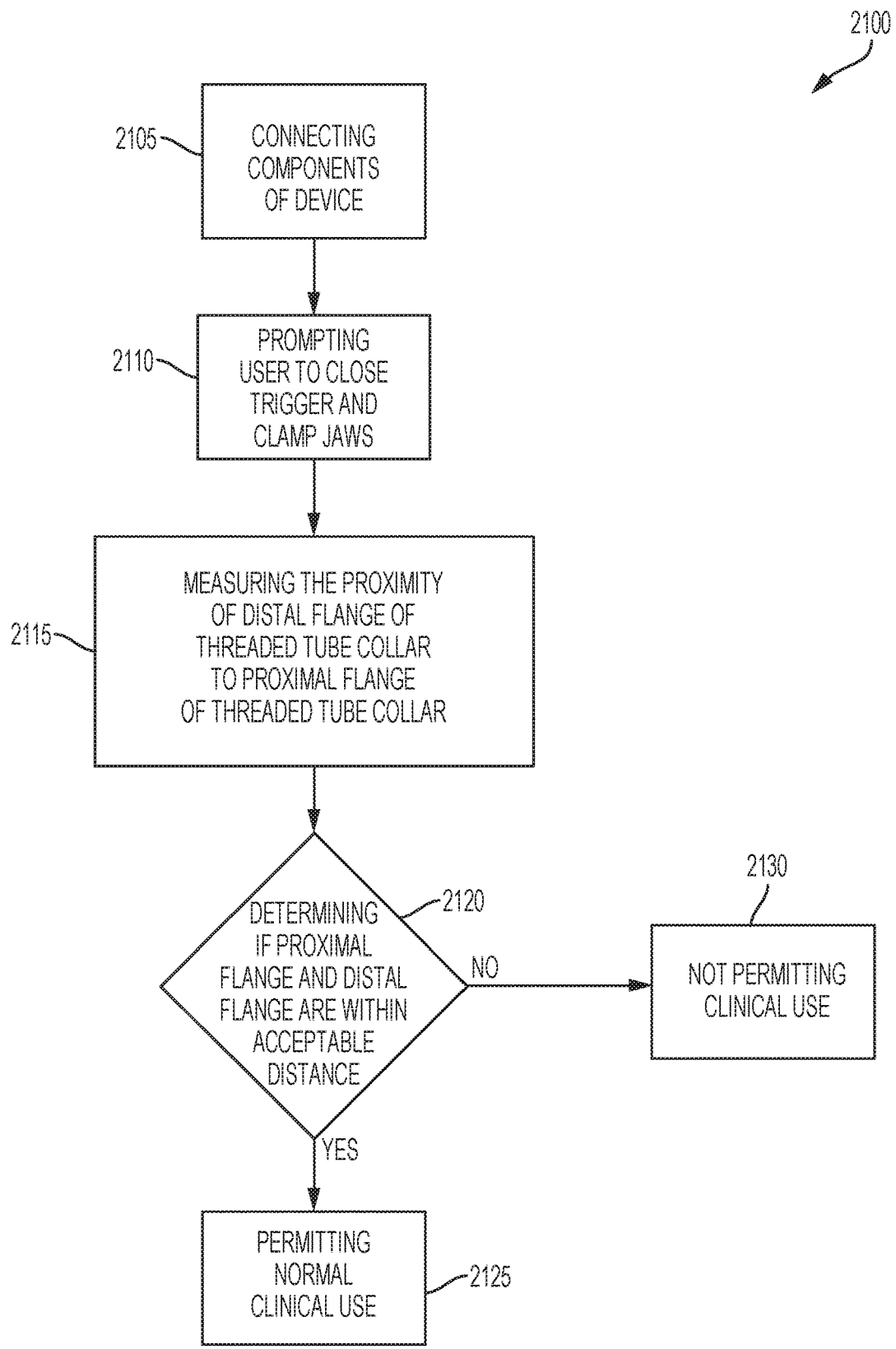
FIG. 21 is a flow chart for a method of determining if a reassembled jaw actuation assembly is within a predetermined tolerance limit in accordance with the present disclosure.

FIG. 21 is a flow chart depicting a method 2100 in which a user may be alerted if a medical device is not properly reassembled based on data received from a sensor of a mechanical motion of one or more components of the medical device. As disclosed above, an ultrasonic medical device may be manufactured to incorporate any of a number of sensors configured to measure or detect motions of one or more mechanical components of the medical device. During the manufacture of the device, for example as part of validation and/or verification processes, the manufacturer may store one or more tolerance limit values in one or more non-volatile memory components. The one or more tolerance limit values received from one or more of the sensors and may be indicative of correct functioning of one or more of the mechanical components based on the sensor values. The values for correct functioning may include, without limitation, correct mechanical travel, correct mechanical position, and correct applied mechanical pressure. It may be understood that tolerance limit values may also be programmed into the non-volatile memory devices by a repair facility authorized by the manufacturer. The user may then receive the new or refurbished medical device from either the manufacturer or from the authorized facility.

A user of the medical device may have disassembled all or part of the medical device in order to provide any type of maintenance including, without limitation, cleaning, sterilizing, replacing, and/or repairing one or more components. The user may then reassemble the medical device including, without limitation, reassembling a clamp arm, a jaw assembly, a reciprocating tubular actuating member, or any one or more components of a trigger assembly linkage (for example 590 in FIG. 5). Thereafter, before clinical use, the user may connect 2105 the medical device to a control system and/or a device generator. In this manner, the user may form an appropriate electrical connection between a reassembled ultrasonic medical device and a control system. As part of a test method, the control system may retrieve one or more tolerance limit values from the non-volatile memory.

The control system may prompt 2110 the user to depress the trigger fully, thereby clamping the jaw assembly proximal to the ultrasonic knife. In one aspect, upon receiving an indication that the jaw assembly is clamped, for example from an output of a trigger sensor, the control system may then activate the piezoelectric transducer by allowing the generator to supply a current to the piezoelectric transducer. It may be understood that the amount of current supplied to the piezoelectric transducer during the test method may be less than that typically supplied during a medical procedure. In one example, the piezoelectric transducer may induce a transverse mechanical wave into the waveguide. In another example, the piezoelectric transducer may induce a non-transverse mechanical wave into the waveguide. The current may be applied for a predetermined amount of time during the test.

In another aspect, the control system may not activate the piezoelectric transducer upon receiving an indication that the jaw assembly is clamped, for example from an output of a trigger sensor as part of this test method.

The one or more electrical components of the medical device may measure 2115 a distance between a distal flange (for example 572a in FIG. 10A) of a threaded tube collar and a proximal flange (for example 572b in FIG. 10A) of the threaded tube collar. It may be understood that such sensor electronics may be disposed in the medical device handle assembly, the control circuit, or the generator. In one non-limiting example, the sensors may measure a distance between a distal flange (for example 572a in FIG. 10A) of a threaded tube collar and a proximal flange (for example 572b in FIG. 10A) of the threaded tube collar. As disclosed above, such sensors may include, without limitation, a resistive sensor, a magnetic sensor, or an optical sensor.

The electrical components and/or the control system or module may then determine 2120 if the measured distance between the distal flange of a threaded tube collar and the proximal flange of the threaded tube collar is within a predetermined tolerance limit. If the measured distance between the distal flange of a threaded tube collar and the proximal flange of the threaded tube collar is within the predetermined tolerance limit, then the control circuit may provide a signal to the user permitting 2125 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

If the measured distance between the distal flange of a threaded tube collar and the proximal flange of the threaded tube collar is not within the predetermined tolerance limit, then the control circuit may provide a signal to the user not permitting 2130 the device for clinical use. The control circuit may further provide a signal to the user recommending that the device should be disassembled and reassembled. Such a signal may include an audio signal or a visual signal. A visual signal may include a text display. In one aspect, the text display may request the user to disassemble and reassemble the device. In another aspect, the text display may suggest that the user check for misaligned or missing components, such as a spring stack, a reciprocating tubular actuating member, the threaded tube collar, or any component thereof.

Figure 22:
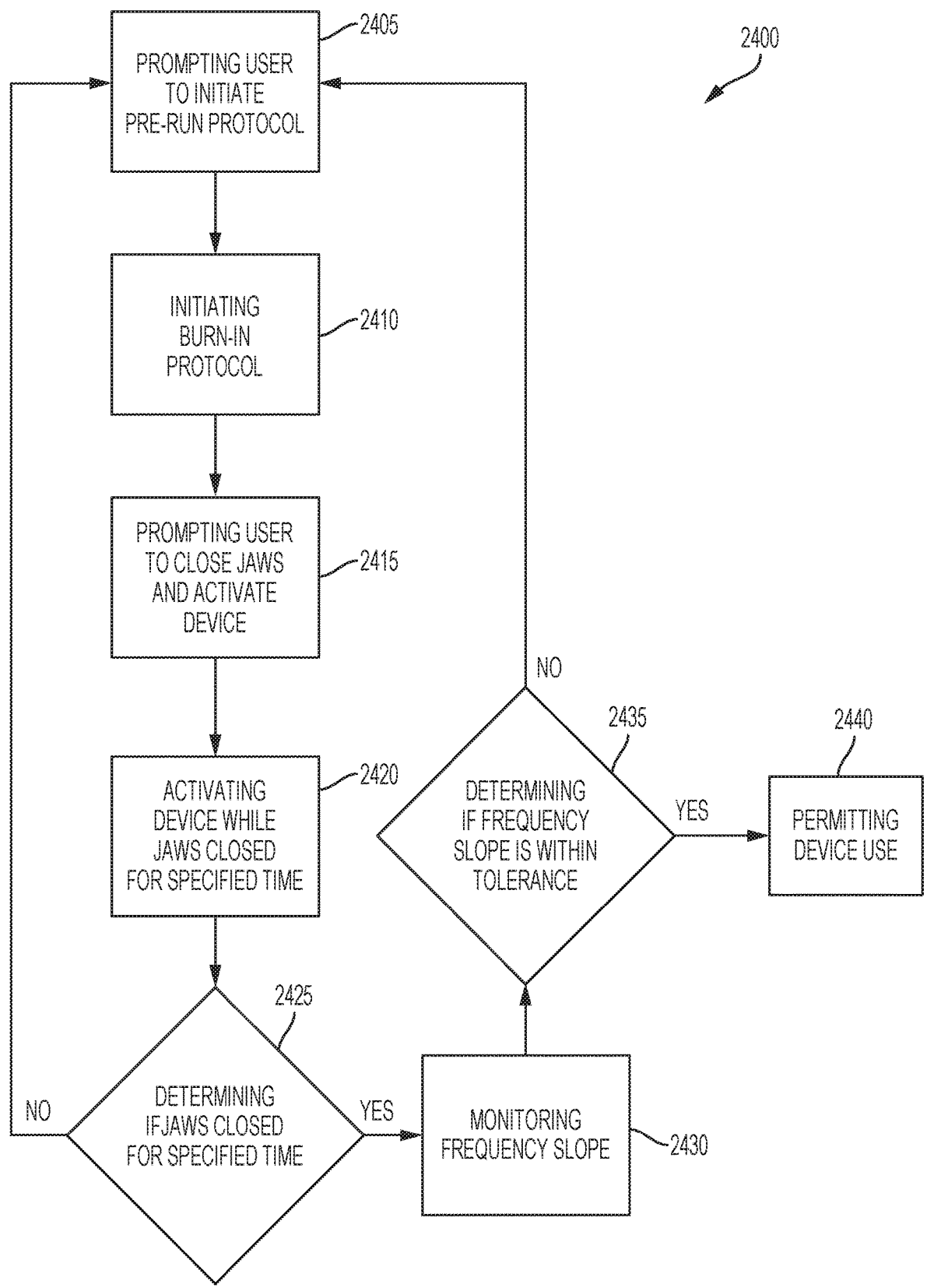
FIG. 22 is a flow chart for a method of pre-testing a function of an ultrasonic medical device prior to its use in a medical procedure in accordance with the present disclosure.

FIG. 22 is a flow chart depicting a method 2400 in which a user may be alerted if a medical device is not properly reassembled prior to a pre-run or burn-in protocol. Such a protocol may be used to test a medical device after replacement of one or more components and before the device is used in a medical procedure. In some non-limiting aspects, components that have been replaced must be burned-in prior to device use. A burn-in protocol may be required for a replacement component that may change its function over time until the component has attained a steady state function or shape. In one non-limiting example, a clamp pad (for example, 330 in FIG. 3) of a clamp arm assembly (for example, 64 in FIG. 3) may be configured to engage tissue between the ultrasonic blade (for example, 66 in FIG. 3) and the clamp arm (for example, 64 in FIG. 3). The clamp pad may comprise a material that may initially wear on contact with the ultrasonic blade during use until it attains a steady-state shape. It may be recognized that the use of a new clamp pad that has not undergone a burn-in protocol during a medical procedure may result in inconsistent results until the clamp pad has attained a steady-state shape. Similarly, the surface of a new ultrasonic blade or knife may require a similar burn-in procedure to assure that the surface does not change during use.

During the manufacture of the device, for example as part of validation and/or verification processes, the manufacturer may store one or more tolerance limit values in one or more non-volatile memory components. In an aspect of a burn-in protocol, the one or more tolerance limit values may represent values that may be indicative of a steady state function of one or more of the medical device components after the component has been successfully burned-in. In another aspect, the one or more tolerance limit values may represent a series of values which may correspond to known, measured, or expected changes in a component function as the burn-in protocol proceeds. It may be understood that tolerance limit values may also be programmed into the non-volatile memory devices by a repair facility authorized by the manufacturer.

A user of the medical device may have disassembled all or part of the medical device in order to provide any type of maintenance including, without limitation, cleaning, sterilizing, replacing, and/or repairing one or more components. The user may then reassemble the medical device including, without limitation, reassembling a clamp arm, an ultrasonic blade, a waveguide, or a clamp pad. Thereafter, before clinical use, the user may attach the medical device to a control system and/or a device generator. In this manner, the user may form an appropriate electrical connection between a reassembled ultrasonic medical device and a control system. As part of a test method, the control system may retrieve one or more tolerance limit values from the non-volatile memory.

After the medical device has been connected to the control system, the control system may prompt 2405 the user to initiate the pre-run protocol. The pre-run protocol may include any number of medical device built in self-tests to test any number of mechanical and/or electrical functions associated with the medical device. The burn-in protocol may be initiated 2410 as part of the initial pre-run protocol. During the burn-in protocol, the user may be prompted 2415 to depress the trigger fully, thereby clamping the jaw assembly proximal to the ultrasonic knife and to actuate the piezoelectric transducer. The control system may then provide a voltage to the piezoelectric transducer, which may in turn induce a mechanical wave in the waveguide and, ultimately, the knife blade. It may be recognized that the voltage applied to the piezoelectric transducer may be less than that normally supplied during a medical procedure.

The system may thus activate 2420 the piezoelectric transducer of the medical device for a set period of time (a burn-in time). In some non-limiting examples, the burn-in time may be for about four seconds. Alternative examples of such a burn-in time may include, without limitation, a burn-in time of about 2 seconds, about 3 seconds, about 4 seconds, about 5 seconds, about 10 seconds, or a value or ranges of values therebetween, including endpoints. Throughout the burn-in time, the control system may receive sensor data from the trigger sensor as it measures the position of the trigger or determines if the trigger is fully compressed. The control system may then determine 2425 if the trigger was fully compressed throughout the burn-in period. It may be recognized that the user may not consistently depress the trigger throughout the burn-in time. The user's fingers may flex and/or relax, and therefore the user may not completely depress the trigger during the entire burn-in time. If the trigger sensor indicates that the trigger was not fully compressed throughout the specified burn-in period, the control system may prompt 2405 the user to re-initiate the pre-run protocol. In an alternative aspect, the control system may also notify the user that the burn-in protocol was not completed due to a fault in the trigger compression. Such a notification may be an audio notification or a visual notification (such as a lighted or flashing LED, or a text message on a screen display).

Throughout the burn-in time, the control system may receive data referencing additional functions of the medical device, in addition to data from the trigger sensor. In one non-limiting example, the control system may receive voltage and current data from the generator during the actuation of the piezoelectric transducer. In some aspects, the control system, along with one or more additional electronic devices, may determine an impedance of the piezoelectric transducer during the burn-in period. Additionally, the generator may sweep an actuation frequency of the piezoelectric transducer during the burn-in time. In this manner, the control system may measure an impedance of the piezoelectric transducer, or a resonant frequency of the piezoelectric transducer throughout the burn-in time.

As disclosed above in reference to FIGS. 17 and 18, the measured impedance and/or resonant frequency of a piezoelectric transducer may be related to the electromechanical coupling factor of the piezoelectric transducer. The electromechanical coupling factor may in turn be related to the acoustic load placed on the transducer, for example from contacts with components such as the clamp pad. It may be understood that wear on the clamp pad and/or the ultrasonic blade during a burn-in protocol may result in a change in the acoustic load on the transducer. During burn-in, the clamp pad may be exposed to wearing conditions by the ultrasonic blade resulting in the clamp pad having a surface optimally contacting the ultrasonic blade. Without being bound by theory, as the surface of the clamp pad adapts to the motion of the ultrasonic blade, the clamp pad may form a better contact with the ultrasonic blade and thus increase the acoustic load on the piezoelectric transducer. The increase in acoustic load may result in an increase in the electromechanical coupling factor which may be detected by a decrease in the resonant frequency.

During the burn-in time, the control system may detect a change in the resonant frequency of the piezoelectric transduce and monitor 2430 a slope of a plot of the resonant frequency over time (that is, a change in resonant frequency per unit time). The control system may then determine 2435 if the slope of the plot of the resonant frequency over the burn-in time is within a range of tolerance limit values. As disclosed above, the tolerance limit values may be stored in a non-volatile memory component in the ultrasonic medical device. In some non-limiting examples, a tolerance limit value may be a minimum value of a change in resonant frequency per unit time. Alternatively, a tolerance limit value may be a steady-state value of the resonant frequency after the burn-in protocol is completed.

If the change in resonant frequency per unit time is within the tolerance limit value or range of values, then the control system may provide a signal to the user that the burn-in protocol is successful, and that the medical device may be permitted 2440 for clinical use. Such a signal may include an audio signal or a visual signal. The audio signal may include, for example, a buzzer or other tone to alert the user. The visual signal may include an illuminated LED (for example, an illuminated LED, or a flashing LED), or a text display. If the change in resonant frequency per unit time is not within the tolerance limit value or range of values, then the control system may provide a signal to the user that the burn-in protocol is unsuccessful, and prompt 2405 the user to re-initiate the pre-run protocol. It may be understood that there may be a predetermined maximum number of times that a user may be prompted to re-initiate the pre-run protocol. In another aspect, the control circuit may track the number of times that a user re-initiates the pre-run protocol and may notify the user to disassemble and reassemble the medical device if the maximum number of re-initiations of the pre-run protocol is exceeded.

Figure 23:
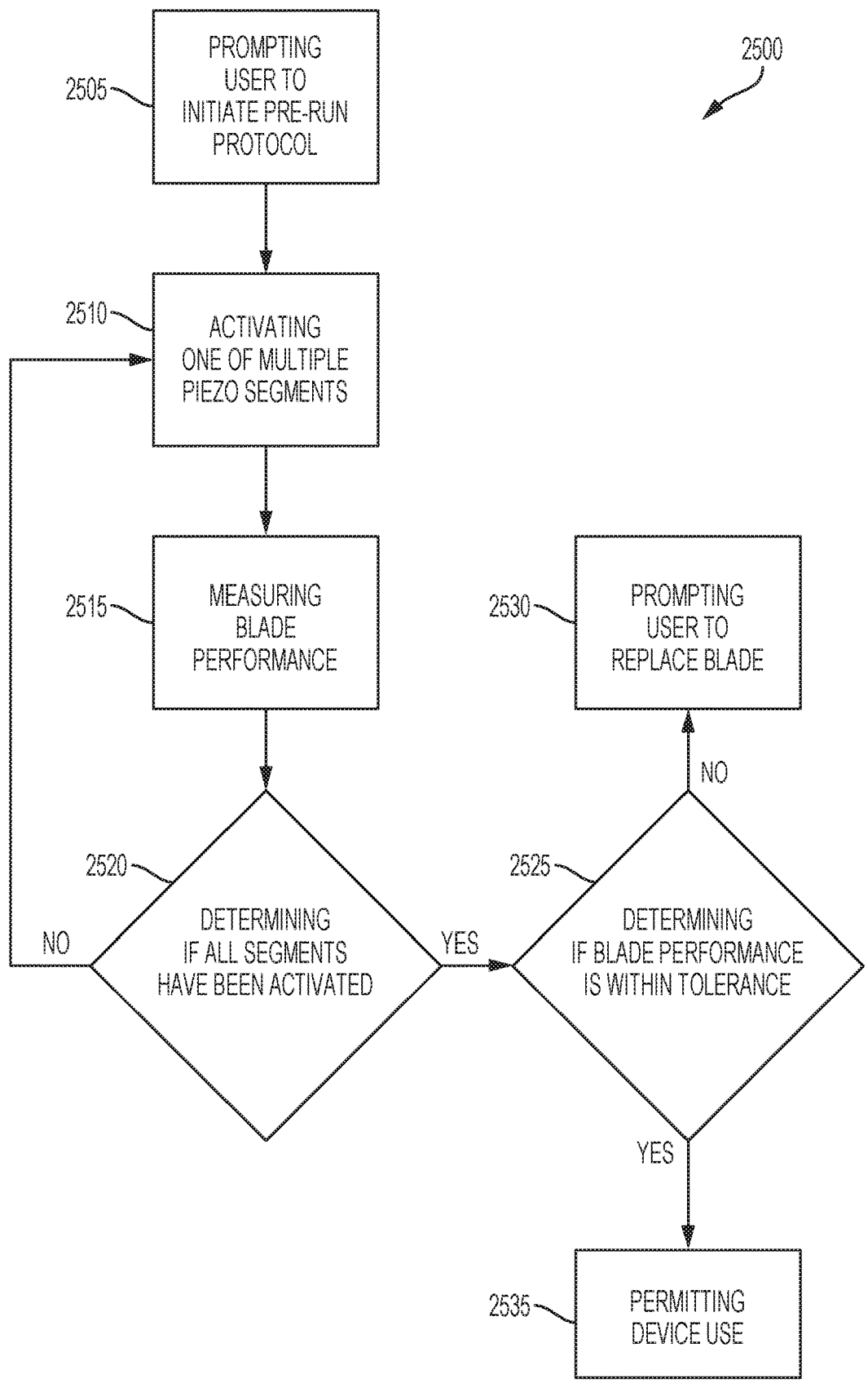
FIG. 23 is a flow chart for a method of determining if a blade of an ultrasonic medical device operates within a predetermined tolerance limit in accordance with the present disclosure.

FIG. 23 is a flow chart depicting a method 2500 in which a user may be alerted if a medical device is not properly reassembled based on data received from a sensor of a mechanical motion of one or more components of the medical device. As disclosed above, an ultrasonic medical device may be manufactured to incorporate any of a number of sensors configured to measure or detect motions of one or more mechanical components of the medical device. During the manufacture of the device, for example as part of validation and/or verification processes, the manufacturer may store one or more tolerance limit values in one or more non-volatile memory components. It may be understood that tolerance limit values may also be programmed into the non-volatile memory devices by a repair facility authorized by the manufacturer. The user may then receive the new or refurbished medical device from either the manufacturer or from the authorized facility.

The one or more tolerance limit values may represent values received from one or more of the sensors and may be indicative of correct functioning of one or more of the mechanical components based on the sensor values. The values for correct functioning may include, without limitation, correct mechanical motion or a correct mechanical position. In some aspects, correct functioning of components may include proper mechanical integrity of the components. As a non-limiting example, mechanical integrity of a waveguide and/or an ultrasonic blade may refer to a waveguide and/or an ultrasonic blade having a proper size and/or shape and lacking physical defects such as pits, cracks, or crazing, A user of the medical device may have disassembled all or part of the medical device in order to provide any type of maintenance including, without limitation, cleaning, sterilizing, replacing, and/or repairing one or more components. The user may then reassemble the medical device including, without limitation, reassembling a piezoelectric transducer, a waveguide, or an ultrasonic blade mechanically coupled to the waveguide. Thereafter, before clinical use, the user may connect the medical device to a control system and/or a device generator. In this manner, the user may form an appropriate electrical connection between a reassembled ultrasonic medical device and a control system. As part of a test method, the control system may retrieve one or more tolerance limit values from the non-volatile memory.

The control system may prompt 2505 the user to initiate a pre-run protocol. In one aspect, the user may be prompted to depress a trigger thereby clamping a jaw assembly proximal to the ultrasonic blade. Upon receiving an indication that the jaw assembly is clamped, for example from an output of a trigger sensor, the control system may then activate a piezoelectric transducer by allowing the generator to supply a current to the piezoelectric transducer. In another aspect, the user is not prompted to depress a trigger to clamp a jaw assembly proximal to the ultrasonic blade. Such an aspect may be appropriate, for example, for an ultrasonic medical device lacking a clamping jaw assembly. In such a pre-run protocol, after the user is prompted 2505 to initiate the pre-run protocol, the control system may activate 2510 one or more piezoelectric transducers and the control system may allow the generator to supply a current to the one or more piezoelectric transducers. It may be understood that the amount of current supplied to the one or more piezoelectric transducers during the test method may be less than that typically supplied during a medical procedure.

One example of a pre-run protocol may be used with an ultrasonic medical device comprising a plurality of piezoelectric transducers as disclosed above with reference to FIG. 9. FIG. 9 illustrates an aspect in which a waveguide is mechanically coupled to a first transducer on a first side and a second transducer on a second and opposing side. Further, the first transducer may comprise a first planar array of first transducer plates and the second transducer may comprise a second planar array of second transducer plates. As illustrated in FIG. 9, the first transducer may comprise a first planar array of first transducer plates indicated by numbers 1, 2, 3, and 4. The second transducer may comprise a second planar array of second transducer plates indicated by numbers in parentheses (5), (6), (7), and (8).

Each transducer or transducer plate illustrated in FIG. 9 may be individually activated. In some aspects, each transducer or transducer plate may be activated by a separate ultrasonic signal generator in which the individual ultrasonic signal generators have a common ground in electrical communication with the acoustic assembly. In such an aspect, each transducer or transducer plate may be activated by a separate electric signal. In some examples, the electrical characteristics of the separate electrical signals may be the same, for example having the same amplitude, frequency, and phase. In alternative examples, the electrical characteristics of the separate electrical signals may differ in one or more of amplitude, frequency, and phase. In alternative aspects, each transducer or transducer plate may be activated by the same ultrasonic signal generator, but may be separately activatable by one or more transducer activation switches. Such switches may direct a first polarity of an ultrasonic signal to one set of transducers or transducer plates and a second polarity of the ultrasonic signal to a second set of transducers or transducer plates.

Further, as disclosed above with respect to FIG. 9, switched activation of the transducers or transducer plates may result in vibrational patterns of the surgical tool that are more complex than a single transverse standing mechanical wave. Such complex mechanical waves may be used to impart complex movement to the end effector of the ultrasonic medical device. For example, with respect to the aspect illustrated in FIG. 9, a predominantly transverse flapping motion may be induced in the end effector if transducer plates 1, 2, (5), and (6) are activated with a first polarity ultrasonic signal while transducer plates 3, 4, (7), and (8) are activated with a second and opposing polarity ultrasonic signal. A predominantly transverse hooking motion may be induced in the end effector if transducer plates 1, (5), 3, and (7) are activated with a first polarity ultrasonic signal while transducer plates 2, (6), 4, and (8) are activated with a second and opposing polarity ultrasonic signal. A predominantly torsional motion may be induced in the end effector if transducer plates 1, (7), 2, and (8) are activated with a first polarity ultrasonic signal while transducer plates 3, (5), 4, and (6) are activated with a second and opposing polarity ultrasonic signal. A combination of torsional and transverse motions may be induced in the end effector if transducer plates 1, (7), 4, and (6) are activated with a first polarity ultrasonic signal while transducer plates (5), 3, 2, and (8) are activated with a second and opposing polarity ultrasonic signal. Additional motions may be achieved through the activation of other groups of transducer plates. Alternatively, each piezoelectric transducer or transducer plate may be individually activated.

For an ultrasonic medical device comprising piezoelectric transducers as disclosed above with respect to FIG. 9, the pre-run protocol may include instructions for the control system to activate 2510 any one or more of the multiple piezoelectric transducers or transducer plates, or any sequence of such activations to induce any of a variety of motions in the waveguide and/or the ultrasonic blade. Thus, as disclosed above, the pre-run protocol may include instructions to activate the transducer plates in order to induce a torsional motion in the waveguide and the ultrasonic blade. The pre-run protocol may include instructions to activate the transducer plates in order to induce a flapping motion in the waveguide and the ultrasonic blade. The pre-run protocol may include instructions to activate the transducer plates in order to induce a hooking motion in the waveguide and the ultrasonic blade. The pre-run protocol may include any sequence or sequences of transducer plate activations required to induce any one or more motions in the waveguide and/or the ultrasonic blade.

During the activation 2510 of any one set of transducer plates, the control system may measure 2515 one or more signals indicative of a waveguide and/or ultrasonic blade function and/or performance. In one non-limiting example, the measurement 2515 of the ultrasonic blade performance may be based on an impedance measurement of the transducer plates. As disclosed above, the impedance measurement may be related to the electromechanical coupling constant which may relate to the ability of the waveguide and/or the ultrasonic blade to store mechanical energy. The ability of the waveguide and/or the ultrasonic blade to store mechanical energy may be altered if any mechanical defect is found in the waveguide, the ultrasonic blade, or the coupling of the ultrasonic blade to the waveguide. In another non-limiting example, the measurement 2515 of the ultrasonic blade performance may be based on a measurement of the resonant frequency of the transducer plates. As disclosed above, the resonant frequency may be related to the electromechanical coupling constant which may relate to the ability of the waveguide and/or the ultrasonic blade to store mechanical energy. In yet another non-limiting example, the measurement 2515 of the ultrasonic blade performance may be based on an optical measurement of a displacement of the waveguide and/or ultrasonic blade during the activation of the piezoelectric plates. In still another non-limiting example, the measurement 2515 of the ultrasonic blade performance may be based on an inductive measurement of a displacement of the waveguide and/or ultrasonic blade during the activation of the piezoelectric plates, in which the waveguide and/or ultrasonic blade are disposed within a solenoid detection system. Such an inductive measurement may be based on the motion of a vibrating reed within the solenoid. Additional sensing mechanisms of movements of the waveguide and/or ultrasonic blade, although not explicitly disclosed herein, may also be used to measure the function and/or performance of the waveguide and/or ultrasonic blade during an activation of one or more piezoelectric transducers or transducer plates. The control system may include instructions to store the measurements of the function and/or performance of the waveguide and/or ultrasonic blade during any activation of one or more piezoelectric transducers or transducer plates.

The control system may then determine 2520 if all of the piezoelectric transducers and/or transducer plate segments have been activated. This determination may include determining if all of the sequences of transducer plate activations required to induce the one or more motions in the waveguide and/or the ultrasonic blade have been run. If all of the sequences of transducer plate activations programmed in the control system have not been run, the controller may then activate 2510 a next sequence of plate activations.

If all of the sequences of transducer plate activations programmed in the control system have been run, the controller may then determine 2525 if the measured blade performance is within the predetermined tolerance limit, then the control circuit may provide a signal to the user permitting 2535 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

Alternatively, if the measured blade performance is not within the predetermined tolerance limit, then the control circuit may provide a signal to the user not to use the surgical device in a clinical procedure. Such a signal may include an audio signal or a visual signal. The audio signal may include, for example, a buzzer or other tone to alert the user. The visual signal may include an illuminated LED (for example, a red LED, or a flashing LED), or a text display. In one non-limiting aspect, the control circuit may prompt 2530 the user to replace the ultrasonic blade, the waveguide, or both the ultrasonic blade and the waveguide.

As disclosed above, an ultrasonic medical device may become fouled with biological material during the course of a medical procedure. In some aspects, the fouling may comprise tissue or fluid from the patient that becomes attached to portions of the ultrasonic medical device that have contacted the patient. In some examples, the tissue or fluid may be observable on the end of the ultrasonic medical device. In such examples, the end of the ultrasonic medical device may be readily cleaned during the procedure. However, in some examples, the tissue or fluid may accumulate in an interior of an elongated shaft assembly, and may not be readily observable. For example, the tissue or fluid may contact the waveguide or the ultrasonic blade. It may be recognized that such tissue or fluid contacting the waveguide and/or ultrasonic blade may reduce the mechanical vibrations induced therein. Consequently, the motion of the ultrasonic blade may be impeded due to the accumulated tissue or fluid.

Figure 24:
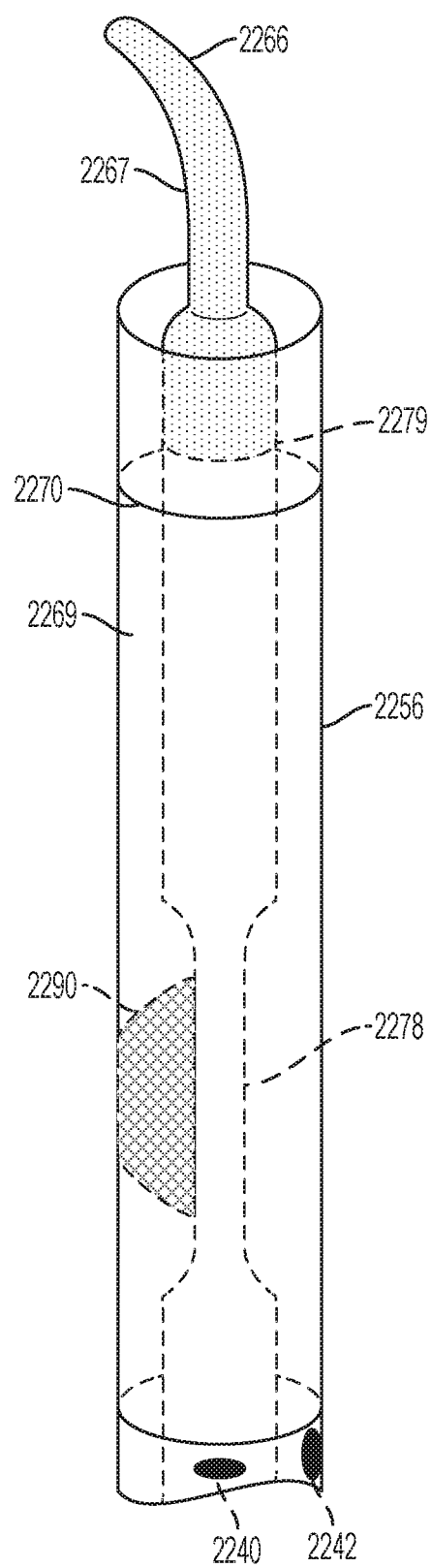
FIG. 24 depicts a longitudinal cross section of an aspect of an ultrasonic medical device in accordance with the present disclosure.

FIG. 24 depicts an aspect of an ultrasonic medical device in which tissue and/or fluid material 2290 has accumulated within an elongated shaft assembly 2256, contacting the waveguide 2278 and potentially preventing the ultrasonic blade 2266 from operating properly. Many aspects of ultrasonic medical devices have been disclosed herein that include a jaw or clamp arm assembly (for example, 64 in FIG. 3) configured to clamp a tissue against an ultrasonic blade to permit cutting the tissue. However, alternative aspects of an ultrasonic medical device may include the ultrasonic blade without a clamp arm or jaw. FIG. 24 depicts such a device.

A method for determining if tissue and/or fluid material 2290 has accumulated within the elongated shaft assembly 2256 of such a medical device may be based on measuring an electrical current that may flow from an electrically conducting waveguide 2278 of an ultrasonic medical device to an electrically conducting and grounded inner surface 2269 of an elongated shaft of the device. For example, the electrically conducting waveguide 2278 may be electrically coupled to a first contact 2240 electrically coupled to a source of an electrical current. Similarly, the electrically conducting inner surface 2269 of the elongated shaft assembly 2256 may be electrically coupled to a second contact 2242 which, in turn, may be electrically coupled to an electrical ground to receive the electrical current.

Without being bound by theory, it may be recognized that biological tissue or fluid (or any aqueous fluid) may conduct an electrical current. Thus, an electrical current flowing from the electrically conducting waveguide 2278 to a conductive inner surface 2269 of the ultrasonic medical device may be an indication that a conductive biological material, such as water, a biological fluid, or a biological tissue 2290, may be disposed on the conductive inner surface 2269 of the elongated shaft assembly 2256 and electrically contacting the electrically conducting waveguide 2278.

It may be understood that an accumulation of tissue and/or fluid 2290 at a distal end of the medical device may be readily observed by a user, and thus the user may remove the observed material during a medical procedure. However, material 2290 deposited in an interior of the elongated shaft assembly 2256 may not be readily observable, and thus a user may not be aware that such material 2290 has accumulated. Therefore, an electrical method to detect an accumulation of material 2290 within such a medical device may require features that would prevent the method from issuing a false-positive indication for readily observable material.

In one non-limiting example, the elongated shaft 2256 may comprise an overmolding of a non-conductive material that may also be disposed partially in the interior distal end of the elongated shaft. The interior edge 2270 of the electrically insulating overmolding material may extend in a proximal direction from the distal edge of the elongated shaft 2256. Portions of the conductive inner surface 2269 proximal to the interior edge 2270 of the electrically insulating overmolding material would be uncoated, and therefore electrically conducting.

Similarly, the ultrasonic knife 2266 may comprise an electrically conducting material and may be electrically coupled to the electrically conducting waveguide 2278. The ultrasonic knife 2266 may also comprise an electrically insulating coating 2267 that extends in a proximal direction from the distal end of the ultrasonic knife 2266. In one non-limiting example, the proximal edge 2279 of the insulating coating 2267 on the ultrasonic knife 2266 may be disposed distal to the interior edge 2270 of the electrically insulating overmolding material of the elongated shaft 2256.

Thus, any accumulated material disposed at the distal end of the ultrasonic medical device—and readily visible to a user of the medical device—may contact electrically insulating material (either the overmolding or the ultrasonic knife coating 2267) and therefore would not be capable of conducting an electrical current. The material 2290 disposed more proximally in the interior of the elongated shaft 2256, however, may contact both the electrically conducting waveguide 2278 and the electrically conducting inner surface 2269 of the elongated shaft 2256. In this manner, a method to determine the presence of a material 2290 within the elongated shaft 2256 may be based on a measurement of a current flow between the electrically conducting waveguide 2278 and the conducting inner surface 2269 of the medical device.

Figure 25:
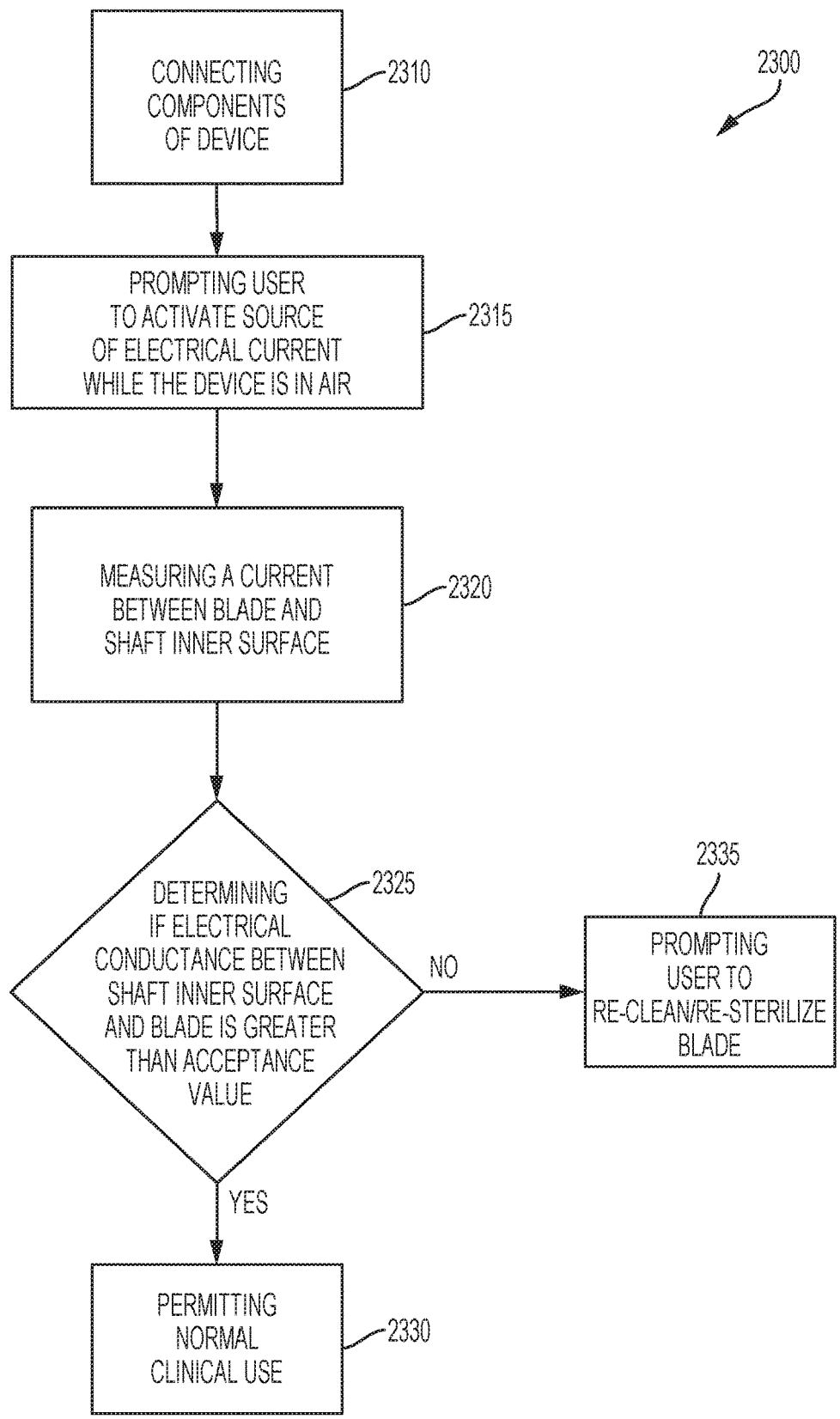
FIG. 25 is a flow chart for a method of determining the presence of undesired material within the ultrasonic medical device depicted in FIG. 24.

FIG. 25 is a flow chart depicting a method 2300 in which a user may be alerted if a biological material or fluid has accumulated in an interior of an elongated shaft assembly of a medical device, such as one depicted in FIG. 24. An ultrasonic medical device may be manufactured to incorporate any of a number of sensors configured to measure a current flow between a conducting waveguide and a conducting and grounded inner surface of the elongated shaft of the medical device. During the manufacture of the device, for example as part of validation and/or verification processes, the manufacturer may store one or more tolerance limit values in one or more non-volatile memory components.

As disclosed above, accumulated material within the elongated shaft of the medical device may result in a current flow between the electrically conducting waveguide and the electrically grounded inner surface of the elongated shaft. The tolerance limit value may include a minimum current flow value. A current flow measured greater than the minimum current flow may be an indication of material accumulated within the elongated shaft assembly. It may be understood that tolerance limit values may also be programmed into the non-volatile memory devices by a repair facility authorized by the manufacturer.

A user of the medical device may have disassembled all or part of the medical device in order to provide any type of maintenance including, without limitation, cleaning, sterilizing, replacing, and/or repairing one or more components.

The user may then connect 2310 the components of the medical device including, without limitation, reassembling a clamp arm, a jaw assembly, a waveguide, or an ultrasonic knife. Thereafter, before clinical use, the user may connect the medical device to a control system and/or a device generator. In this manner, the user may form an appropriate electrical connection between a reassembled ultrasonic medical device and a control system. As part of a test method, the control system may retrieve one or more tolerance limit values from the non-volatile memory.

The control system may prompt 2315 the user to activate a source of an electrical current electrically coupled to the conducting waveguide of the medical device while the device is not in contact with a patient. In some aspects, the medical device may be held by the user so that the distal end of the medical device is in air. It may be understood that the medical device may include user operated controls on a handle of the medical device that are configured to activate the current source. The current may be applied for a predetermined amount of time during the test. In one aspect, a source of the electrical current may be disposed within a handle assembly of the medical device. In another aspect, the source of the electrical current may be disposed in a component exterior to the handle, for example in a power generator.

The one or more electrical components of the medical device may measure 2320 an electrical current passing from the conducting waveguide to the grounded inner conducting surface of the elongated shaft assembly. It may be understood that such sensor electronics may be disposed in the medical device handle assembly, the control circuit, or the generator. The electrical components configured to measure 2320 the electrical current may comprise any such electrical components including, without limitations, resistors, capacitors, inductors, and integrated circuits such as amplifiers and comparators.

The electrical components and/or the control system or module may then determine 2325 if the measured current between the conducting waveguide and the grounded conductive inner surface of the elongated shaft assembly is greater than a predetermined tolerance limit. If the measured current flow is less than the predetermined tolerance limit, then the control circuit may provide a signal to the user permitting 2330 the surgical device to be used in a clinical procedure. Such a signal may include an audio signal or a visual signal. The audio signal may include, for example, a buzzer or other tone to alert the user. The visual signal may include an illuminated LED (for example, a red LED, or a flashing LED), or a text display.

If the measured current flow is greater than the predetermined tolerance limit, then the control circuit may prompt 2335 the user to disassemble the medical device to re-clean and/or re-sterilize the ultrasonic blade and/or the conducting waveguide. The control circuit may issue any signal to prompt the user to re-clean and/or re-sterilize the medical device. Such a signal may include an audio signal or a visual signal. A visual signal may include a text display.

Disclosed above are a number of features for an ultrasonic medical device that may be related to methods to determine if the medical device, having been assembled or reassembled by a user, is in acceptable condition for use during a medical procedure. Although the specific features have been disclosed with reference to a particular device, it may be recognized that such features, and the referenced device, are not limited to the aspects disclosed above.

Disassembly and reassembly of an ultrasonic medical device may include disassembly and reassembly of the entire medical device or one or more parts of the medical device. The one or more parts disassembled and reassembled by a user may include one or more discrete parts and/or one or more subassembly of parts. The one or more subassemblies may be further disassembled and reassembled into one or more constituent parts. The one or more parts disassembled and reassembled by a user may include one or more mechanical parts, one or more electromechanical parts, one or more electrical parts, or any combination or combinations thereof. Disassembly and reassembly may be accomplished through any appropriate means through the use of one or more tools. Alternatively, disassembly and reassembly may be accomplished by hand without the need for any tools.

The ultrasonic medical device may include one or more piezoelectric transducers mechanically coupled to a waveguide. The piezoelectric transducers may include any number, type, or disposition with respect to the waveguide. The piezoelectric transducers may operate in any mechanical mode configured to impart an ultrasonic mechanical wave to the waveguide including, without limitation, a D31 mode and a D33 mode. The one or more piezoelectric transducers may be mechanically affixed to the waveguide, for example by means of an adhesive. Alternatively, the one or more piezoelectric transducers may be incorporated into a piezoelectric transducer assembly comprising the piezoelectric transducers and additional components configured to direct the ultrasonic mechanical wave into the waveguide. Such a piezoelectric transducer assembly may be configured for disassembly and reassembly by the user. A piezoelectric transducer assembly may be reversibly mechanically coupled to the waveguide.

The waveguide may, in turn, be mechanically coupled to an ultrasonic knife or blade. Such mechanical coupling may include any mechanical coupling configured to permit the ultrasonic mechanical wave to be imparted to the ultrasonic knife or blade from the waveguide. In some aspects, the waveguide and the ultrasonic knife or blade may comprise separate components that may be mechanically coupled through any mechanical means including, without limitation, a weld, a stud, or an adhesive. In some alternative aspects, the waveguide and the ultrasonic knife or blade may comprise a single component.

In some aspects, the ultrasonic medical device may include a jaw assembly or a clamp, configured to bring a piece of tissue proximal to the ultrasonic knife or blade for cutting. The jaw assembly or clamp may be actuated by one or more components that move in a reciprocating linear or axial direction. Although the aspect disclosed above is directed to a reciprocating tube component disposed within and coaxial with an outer shaft assembly, it may be understood that any linearly reciprocating component or components may be used to actuate the jaw assembly or clamp. Alternative examples of a linearly reciprocating component that may be used to actuate the jaw assembly or clamp may include, without limitation, a reciprocating rod, one or more reciprocating wires, and one or more reciprocating bands. Thus, the sensors disclosed above that may be used to detect and/or measure a linear displacement of the reciprocating tube component may equally be used to detect and/or measure a linear displacement of any other linearly reciprocating component or components that may be configured to actuate the jaw assembly or clamp. It may be recognized that other sensors than those disclosed above may be incorporated in an ultrasonic medical device that includes one or more alternative linearly reciprocating components to actuate the jaw assembly or clamp.

In the aspects disclosed above, the motion of the reciprocating tube component is directed by the compression of a trigger by a user via a number of mechanical components comprising a trigger assembly linkage. In the aspects disclosed above, a compression of the trigger may cause the reciprocating tube component to move in a proximal direction thereby causing the jaw assembly or clamp to bring the tissue proximal to the ultrasonic knife or blade. In alternative aspects, a compression of the trigger may cause the reciprocating tube component to move in a distal direction thereby causing the jaw assembly or clamp to bring the tissue proximal to the ultrasonic knife or blade. A suitable trigger assembly linkage may be included to cause such a distal motion upon compression of the trigger.

On compression of the trigger, one or more spring assemblies may be disposed to store mechanical energy. When the compression of the trigger is removed, the stored mechanical energy in the one or more spring assemblies may operate to restore the position of the reciprocating tube assembly to an initial position. In the aspects depicted above, such a spring assembly may include a spring stack disposed between a distal flange and a proximal flange of a reciprocating collar. Such a spring stack may comprise a wave spring, as depicted in FIG. 5. Alternative spring assemblies may be disposed among any of the components configured to restore the position of the reciprocating tube assembly to an initial position. Additional examples of such springs may include, without limitation, a helical spring, a leaf spring, and a spiral spring. The sensors disclosed above that may be used to detect and/or measure a displacement of a spring or an amount of a restoration force stored in a spring may equally be used to detect and/or measure a displacement of a spring or an amount of a restoration force stored in a spring for any alternative spring assemblies. It may be recognized that other sensors than those disclosed above may be incorporated in an ultrasonic medical device that includes one or more alternative spring assemblies disposed to restore a reciprocating tube assembly to an initial position.

Further, in some other aspects, the ultrasonic medical device may lack a jaw assembly or clamp configured to bring a piece of tissue proximal to the ultrasonic knife or blade for cutting. Such an ultrasonic medical device may therefor lack those components configured to move a jaw assembly or clamp and may similarly not include sensors configured to detect and/or measure a displacement of such components.

The methods for testing or burning-in a reassembled medical device may be fully automated or partially automated. A fully automated testing method may be actuated after a device user actuates a switch or other control device incorporated in a handle of the medical device or in a medical device controller. In another aspect, a fully automated testing method may be actuated on device power-up. In another aspect, a partially automated testing method may require additional actions on the part of a user such as compressing a trigger to actuate a jaw assembly.

While various details have been set forth in the foregoing description, it will be appreciated that the various aspects of the techniques for operating a generator for digitally generating electrical signal waveforms and surgical devices may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been depicted in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been depicted and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Wth respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

Wth respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered examples:

Example 1

A method of managing a re-usable ultrasonic medical device, the method comprising:
　receiving, by an ultrasonic medical device control module, an electrical connection from an ultrasonic medical device reassembled by a user;
　prompting, by the ultrasonic medical device control module, the user to operate a jaw control component configured to close a jaw of an end effector of the re-assembled ultrasonic medical device;
　receiving, by the ultrasonic medical device control module, closure data from a closure sensor disposed within the ultrasonic medical device indicating that the jaw of the end effector is in a closed configuration;
　receiving, by the ultrasonic medical device control module, functional data from the ultrasonic medical device referencing a functional state of at least one component of the re-assembled ultrasonic medical device;
　comparing, by the ultrasonic medical device control module, a value of the functional data with one or more predetermined acceptance reference values; and
　providing, by the ultrasonic medical device control module, to the user an acceptability indication based on the comparison of the value of the functional data and the one or more predetermined acceptance reference values.

Example 2

The method of Example 1, wherein receiving an electrical connection from an ultrasonic medical device reassembled by a user comprises receiving an electrical connection from an ultrasonic medical device having at least one component re-cleaned or re-sterilized by the user.

Example 3

The method of any one of Example 1 or Example 2, wherein receiving an electrical connection from an ultrasonic medical device reassembled by a user comprises receiving an electrical connection from an ultrasonic medical device having at least one repaired component.

Example 4

The method of any one of Example 1 through Example 3, wherein receiving an electrical connection from an ultrasonic medical device reassembled by a user comprises receiving an electrical connection from an ultrasonic medical device having at least one replaced component.

Example 5

The method of any one of Example 1 through Example 4, further comprising determining, by the ultrasonic medical device control module, that the value of the functional data is within the acceptance range, and
wherein providing to the user an acceptability indication based on the comparison of the value of the functional data and the one or more predetermined acceptance reference values comprises providing to the user an indication of device acceptability for medical use.

Example 6

The method of any one of Example 1 through Example 5, further comprising determining, by the ultrasonic medical device control module, that the value of the functional data is not within the acceptance range, and
wherein providing to the user an acceptability indication based on the comparison of the value of the functional data and the one or more predetermined acceptance reference values comprises providing to the user an indication of device non-acceptability for medical use.

Example 7

The method of any one of Example 1 through Example 6, further comprising receiving, by the ultrasonic medical device control module, the one or more predetermined acceptance reference values from a programmable memory device disposed within the re-assembled ultrasonic medical device.

Example 8

The method of Example 7, further comprising programming the programmable memory device with the one or more predetermined acceptance reference values during an initial manufacture of the re-assembled ultrasonic medical device.

Example 9

The method of any one of Example 1 through Example 8, wherein receiving functional data from the ultrasonic medical device comprises receiving functional data from the ultrasonic medical device referencing a displacement value of a tubular actuating member configured to actuate a jaw of the re-assembled ultrasonic medical device.

Example 10

The method of Example 9, wherein receiving functional data from the ultrasonic medical device referencing a displacement value of a tubular actuating member comprises receiving data from a Hall Effect sensor configured to measure a displacement value of the tubular actuating member.

Example 11

The method of any one of Example 1 through Example 10, wherein receiving functional data from the ultrasonic medical device comprises receiving functional data from the ultrasonic medical device referencing a displacement value of a spring stack in mechanical communication with a tubular actuating member configured to actuate the jaw of the re-assembled ultrasonic medical device.

Example 12

The method of Example 11, wherein receiving functional data from the ultrasonic medical device referencing a displacement value of a spring stack comprises receiving data from a Hall Effect sensor configured to measure a displacement value of the spring stack.

Example 13

The method of any one of Example 1 through Example 12, further comprising:
providing, by the ultrasonic medical device control module, a current to a piezoelectric actuator acoustically coupled to an ultrasonic waveguide, and
wherein receiving functional data from the ultrasonic medical device comprises receiving functional data from the ultrasonic medical device referencing an impedance associated with the ultrasonic waveguide.

Example 14

The method of Example 13, wherein providing, to a user, an acceptability indication based on the comparison of the value of the functional data and the one or more predetermined acceptance reference values comprises providing an indication of the presence of a vibration damping membrane in the re-assembled ultrasonic medical device.

Example 15

The method of any one or more of Example 13 through Example 14, wherein providing a current to a piezoelectric actuator acoustically coupled to an ultrasonic waveguide comprises providing a current to a piezoelectric actuator configured to induce a transverse mechanical wave in the ultrasonic waveguide.

Example 16

The method of any one or more of Example 13 through Example 14, wherein providing a current to a piezoelectric actuator acoustically coupled to an ultrasonic waveguide comprises providing a current to a piezoelectric actuator configured to induce a non-transverse mechanical wave in the ultrasonic waveguide.

Example 17

The method of Example 16, wherein providing a current to a piezoelectric actuator acoustically coupled to an ultrasonic waveguide comprises providing a current to one or more of a plurality of piezoelectric elements acoustically coupled to the ultrasonic waveguide, wherein each of the one or more of the plurality of piezoelectric actuators is configured to induce a non-transverse mechanical wave in the ultrasonic waveguide.

Example 18

The method of any one of Example 13 through Example 17, wherein providing, to a user, an acceptability indication based on the comparison of the value of the functional data and the one or more predetermined acceptance reference values comprises prompting the user to replace the ultrasonic waveguide or replace an ultrasonic knife acoustically coupled to the ultrasonic waveguide.

Example 19

The method of any one of Example 1 through Example 18, further comprising:
  providing, by the ultrasonic medical device control module, a current to a piezoelectric actuator acoustically coupled to an ultrasonic waveguide, and
  receiving, by the ultrasonic medical device control module, functional data from the ultrasonic medical device referencing a mechanical resonant frequency associated with an ultrasonic waveguide acoustically coupled to the ultrasonic waveguide.

Example 20

The method of Example 19, wherein providing, to the user, an acceptability indication comprises prompting the user to re-assemble the re-assembled ultrasonic medical device.

Example 21

The method of any one of Example 1 through Example 20, wherein receiving functional data from the ultrasonic medical device comprises receiving functional data from the ultrasonic medical device referencing a clamp force value of a pad in mechanical communication with the jaw of the ultrasonic medical device against an ultrasonic knife of the re-assembled ultrasonic medical device.

Example 22

The method of Example 21, wherein receiving functional data from the ultrasonic medical device referencing a clamp force value comprises receiving data from a piezoelectric force sensor mechanically coupled to a component of an actuating member drive assembly configured to actuate the jaw of the re-assembled ultrasonic medical device.

Example 23

The method of any one of Example 1 through Example 22, wherein receiving functional data from the ultrasonic medical device comprises receiving functional data from the ultrasonic medical device referencing a distance between a distal flange in mechanical communication with an extension tube and a proximal flange in mechanical communication with the extension tube, wherein the extension tube is configured to actuate a jaw of the re-assembled ultrasonic medical device.

Example 24

The method of any one of Example 1 through Example 23, further comprising:
  prompting, by the ultrasonic medical device control module, the user to initiate a pre-run process comprising a burn-in process;
  activating, by the ultrasonic medical device control module, the pre-run process for a pre-determined period of time; and
  determining, by the ultrasonic medical device control module, from the closure data, that the jaw of the end effector is in a closed configuration for the pre-determined period of time,
  wherein receiving functional data from the ultrasonic medical device referencing a functional state of at least one component of the ultrasonic medical device comprises receiving functional data referencing a resonant frequency of an ultrasonic knife over the pre-determined period of time.

Example 25

A re-usable ultrasonic medical device comprising:
  a handle assembly;
  an elongated shaft assembly, mechanically coupled to the handle assembly, having an interior distal portion over-molded with an electrically insulating material, wherein at least a portion of a proximal interior surface of the elongated shaft assembly is electrically conducting;
  a first electrical contact electrically coupled to the electrically conducting interior surface of the elongated shaft assembly;
  an electrically conducting waveguide disposed within the elongated shaft assembly;
  a second electrical contact electrically coupled to the electrically conducting waveguide;
  an electrically conducting ultrasonic knife acoustically and electrically coupled to the waveguide, having a distal portion coated with an electrically insulating coating;
  a generator configured to deliver power to an ultrasonic transducer acoustically coupled to the waveguide; and
  a controller module configured to control the generator, wherein the controller module comprises:
    a processor; and
    a memory circuit configured to contain instructions which, when executed by the processor, causes the processor to:
      apply an electrical potential between the first contact and the second contact;
      measure an electrical current flowing between the first contact and the second contact; and
      notify a user of the re-usable ultrasonic medical device when the voltage has a value outside a tolerance range.

Example 26

The ultrasonic medical device of Example 25, wherein the electrically insulating coating of the distal portion of the electrically conducting ultrasonic blade has a proximal coating edge that is distal to a distal edge of the electrically insulating material over-molded on the interior distal portion of the elongated shaft assembly.

Example 27

A method of managing a re-usable ultrasonic medical device, the method comprising:
receiving, by an ultrasonic medical device control module, an electrical connection from an ultrasonic medical device reassembled by a user;
applying, by the ultrasonic medical device control module, an electrical potential between a first contact electrically coupled to an electrically conducting waveguide and a second contact electrically coupled to an electrically conducting inner surface of an elongated shaft assembly, wherein the waveguide is disposed in an interior space within the elongated shaft assembly;
measuring, by the ultrasonic medical device control module, an electrical current flowing between the first contact and the second contact;
comparing, by the ultrasonic medical device control module, a value of the electrical current with one or more values of an acceptance range; and
providing, by the ultrasonic medical device control module, to the user an acceptability indication based on the comparison of the value of the electrical current and the one or more predetermined acceptance reference values.

Example 28

The method of Example 27, further comprising determining, by the ultrasonic medical device control module, that the value of the electrical current is within the acceptance range, and
wherein providing to the user an acceptability indication based on the comparison of the value of the electrical current and the one or more predetermined acceptance reference values comprises providing to the user an indication of device acceptability for medical use.

Example 29

The method of any one of Example 27 through Example 28, further comprising determining, by the ultrasonic medical device control module, that the value of the electrical current is not within the acceptance range, and
wherein providing to the user an acceptability indication based on the comparison of the value of the electrical current and the one or more predetermined acceptance reference values comprises providing to the user an indication of device non-acceptability for medical use.

Example 30

The method of Example 29, further comprising prompting, by the ultrasonic medical device control module, the user to clean or re-sterilize a component of the reassembled ultrasonic medical device.

Example 31

A re-usable ultrasonic medical device comprising:
a handle assembly comprising:
a trigger assembly;
a trigger sensor configured to determine a position of the trigger assembly;
a yoke mechanically coupled to the trigger assembly;
an actuating member drive assembly comprising:
a coupling assembly, comprising a tube collar having a distal flange and a proximal flange, a spring stack disposed between the distal flange and the proximal flange, and a force sensor mechanically coupled to the spring stack,
wherein the coupling assembly is configured to receive the yoke between the distal flange and the proximal flange;
an elongated shaft assembly, mechanically coupled to the handle assembly at a proximal end, comprising:
an outer sheath;
a tubular actuating member disposed within the outer sheath, wherein a proximal portion of the tubular actuating member is mechanically coupled to the actuating member drive assembly; and
an end effector assembly mechanically coupled at a distal end of the elongated shaft assembly, wherein the end effector assembly comprises:
an ultrasonic knife; and
a jaw assembly configured to releasably engage the ultrasonic knife, wherein the jaw assembly is mechanically coupled to a distal end of the tubular actuating member; and
a controller module configured to receive trigger position data from the trigger sensor and force data from the force sensor,
wherein one or more components of the re-usable ultrasonic medical device is configured to be replaceable by a user of the medical device.

Example 32

The re-usable ultrasonic medical device of Example 31, wherein the force sensor comprises a piezoelectric disk.

Example 33

The re-usable ultrasonic medical device of Example 32, wherein the controller module comprises:
a processor; and
a first memory circuit configured to contain instructions which, when executed by the processor, causes the processor to:
determine a value of an electrical potential between a first contact disposed on a first side of the piezoelectric disk and a second contact disposed on a second side of the piezoelectric disk;
calculate a force value based on the electrical potential; and
notify a user of the re-usable ultrasonic medical device when the force value is outside a tolerance range.

Example 34

The re-usable ultrasonic medical device of Example 33, wherein the handle assembly further comprises a programmable memory circuit configured to contain stored values corresponding to the tolerance range, and
wherein the controller module is configured to receive the stored valued from the memory circuit.

Example 35

The re-usable ultrasonic medical device of any one of Example 33 through Example 34, wherein the handle assembly further comprises a programmable memory circuit configured to contain potential/force standardization data, and
  wherein the instructions which, when executed by the processor, causes the processor to calculate a force value based on the electrical potential comprise instructions which, when executed by the processor, causes the processor to calculate a force value based on the electrical potential and the potential/force standardization data.

What is claimed is:

1. A method of managing a re-usable ultrasonic medical device, the method comprising:
  receiving, by an ultrasonic medical device control module, an electrical connection from an ultrasonic medical device reassembled by a user;
  prompting, by the ultrasonic medical device control module, the user to operate a jaw control component configured to close a jaw of an end effector of the re-assembled ultrasonic medical device;
  receiving, by the ultrasonic medical device control module, closure data from a closure sensor disposed within the re-assembled ultrasonic medical device indicating that the jaw of the end effector is in a closed configuration;
  receiving, by the ultrasonic medical device control module, functional data from the re-assembled ultrasonic medical device referencing a functional state of at least one component of the re-assembled ultrasonic medical device;
  comparing, by the ultrasonic medical device control module, a value of the functional data with one or more predetermined acceptance reference values; and
  providing, by the ultrasonic medical device control module to the user, an acceptability indication based on the comparison of the value of the functional data and the one or more predetermined acceptance reference values,
  wherein receiving functional data from the re-assembled ultrasonic medical device comprises receiving functional data from the re-assembled ultrasonic medical device referencing a displacement value of a tubular actuating member configured to actuate the jaw of the re-assembled ultrasonic medical device, and
  wherein receiving functional data from the re-assembled ultrasonic medical device referencing a displacement value of a tubular actuating member comprises receiving data from a Hall Effect sensor configured to measure the displacement value of the tubular actuating member.

2. The method of claim 1, wherein receiving an electrical connection from an ultrasonic medical device reassembled by a user comprises receiving the electrical connection from an ultrasonic medical device having at least one component re-cleaned or re-sterilized by the user.

3. The method of claim 1, wherein receiving an electrical connection from an ultrasonic medical device reassembled by a user comprises receiving the electrical connection from an ultrasonic medical device having at least one repaired component.

4. The method of claim 1, wherein receiving an electrical connection from an ultrasonic medical device reassembled by a user comprises receiving the electrical connection from an ultrasonic medical device having at least one replaced component.

5. The method of claim 1, further comprising determining, by the ultrasonic medical device control module, that the value of the functional data equals one of the one or more predetermined acceptance reference values, and
  wherein providing to the user an acceptability indication based on the comparison of the value of the functional data and the one or more predetermined acceptance reference values comprises providing to the user an indication of device acceptability for medical use.

6. The method of claim 1, further comprising determining, by the ultrasonic medical device control module, that the value of the functional data does not equal one of the one or more predetermined acceptance reference values, and
  wherein providing to the user an acceptability indication based on the comparison of the value of the functional data and the one or more predetermined acceptance reference values comprises providing to the user an indication of device non-acceptability for medical use.

7. The method of claim 1, further comprising receiving, by the ultrasonic medical device control module, the one or more predetermined acceptance reference values from a programmable memory device disposed within the re-assembled ultrasonic medical device.

8. The method of claim 7, further comprising programming the programmable memory device with the one or more predetermined acceptance reference values during an initial manufacture of the re-assembled ultrasonic medical device.

9. The method of claim 1, further comprising receiving functional data from the re-assembled ultrasonic medical device referencing a displacement value of a spring stack in mechanical communication with the tubular actuating member.

10. The method of claim 9, wherein receiving functional data from the re-assembled ultrasonic medical device referencing a displacement value of a spring stack comprises receiving data from a Hall Effect sensor configured to measure the displacement value of the spring stack.

11. The method of claim 1, further comprising:
  providing, by the ultrasonic medical device control module, a current to a piezoelectric actuator acoustically coupled to an ultrasonic waveguide, and
  receiving functional data from the re-assembled ultrasonic medical device referencing an impedance associated with the ultrasonic waveguide.

12. The method of claim 11, wherein providing, to the user, an acceptability indication based on the comparison of the value of the functional data and the one or more predetermined acceptance reference values comprises providing an indication of a presence of a vibration damping membrane in the re-assembled ultrasonic medical device.

13. The method of claim 11, wherein providing a current to a piezoelectric actuator acoustically coupled to an ultrasonic waveguide comprises providing a current to a piezoelectric actuator configured to induce a transverse mechanical wave in the ultrasonic waveguide.

14. The method of claim 11, wherein providing a current to a piezoelectric actuator acoustically coupled to an ultrasonic waveguide comprises providing the current to a piezoelectric actuator configured to induce a non-transverse mechanical wave in the ultrasonic waveguide.

15. The method of claim 14, wherein providing a current to a piezoelectric actuator acoustically coupled to an ultrasonic waveguide comprises providing the current to one or more of a plurality of piezoelectric elements acoustically coupled to the ultrasonic waveguide, wherein each of the one or more of the plurality of piezoelectric elements is configured to induce the non-transverse mechanical wave in the ultrasonic waveguide.

16. The method of claim 11, wherein providing, to the user, an acceptability indication based on the comparison of the value of the functional data and the one or more predetermined acceptance reference values comprises prompting the user to replace the ultrasonic waveguide or replace an ultrasonic knife acoustically coupled to the ultrasonic waveguide.

17. The method of claim 1, further comprising:
providing, by the ultrasonic medical device control module, a current to a piezoelectric actuator acoustically coupled to an ultrasonic waveguide, and
receiving, by the ultrasonic medical device control module, functional data from the re-assembled ultrasonic medical device referencing a mechanical resonant frequency associated with an ultrasonic waveguide acoustically coupled to the piezoelectric actuator.

18. The method of claim 17, wherein providing, to the user, an acceptability indication comprises prompting the user to re-assemble the re-assembled ultrasonic medical device.

19. The method of claim 1, further comprising receiving functional data from the re-assembled ultrasonic medical device referencing a clamp force value of a pad in mechanical communication with the jaw of the re-assembled ultrasonic medical device against an ultrasonic knife of the re-assembled ultrasonic medical device.

20. The method of claim 19, wherein receiving functional data from the re-assembled ultrasonic medical device referencing a clamp force value comprises receiving data from a piezoelectric force sensor mechanically coupled to a component of an actuating member drive assembly configured to actuate the jaw of the re-assembled ultrasonic medical device.

21. The method of claim 1, further comprising receiving functional data from the re-assembled ultrasonic medical device referencing a distance between a distal flange in mechanical communication with the tubular actuating member and a proximal flange in mechanical communication with a reciprocating collar body.

22. The method of claim 1, further comprising:
prompting, by the ultrasonic medical device control module, the user to initiate a pre-run process comprising a burn-in process;
activating, by the ultrasonic medical device control module, the pre-run process for a pre-determined period of time; and
determining, by the ultrasonic medical device control module, from the closure data, that the jaw of the end effector is in the closed configuration for the pre-determined period of time,
wherein receiving functional data from the re-assembled ultrasonic medical device referencing a functional state of at least one component of the re-assembled ultrasonic medical device comprises receiving functional data referencing a resonant frequency of an ultrasonic knife over the pre-determined period of time.

23. A method of managing a re-usable ultrasonic medical device, the method comprising:
receiving, by an ultrasonic medical device control module, an electrical connection from an ultrasonic medical device reassembled by a user;
applying, by the ultrasonic medical device control module, an electrical potential between a first contact electrically coupled to an electrically conducting waveguide and a second contact electrically coupled to an electrically conducting inner surface of an elongated shaft assembly, wherein the electrically conducting waveguide is disposed in an interior space within the elongated shaft assembly;
measuring, by the ultrasonic medical device control module, an electrical current flowing between the first contact and the second contact;
comparing, by the ultrasonic medical device control module, a value of the electrical current with one or more values of an acceptance range; and
providing, by the ultrasonic medical device control module, to the user an acceptability indication based on the comparison of the value of the electrical current and the one or more values of the acceptance range.

24. The method of claim 23, further comprising determining, by the ultrasonic medical device control module, that the value of the electrical current is within the one or more values of the acceptance range, and
wherein providing to the user an acceptability indication based on the comparison of the value of the electrical current and the one or more values of the acceptance range comprises providing to the user an indication of device acceptability for medical use.

25. The method of claim 23, further comprising determining, by the ultrasonic medical device control module, that the value of the electrical current is not within the one or more values of the acceptance range, and
wherein providing to the user an acceptability indication based on the comparison of the value of the electrical current and the one or more values of the acceptance range comprises providing to the user an indication of device non-acceptability for medical use.

26. The method of claim 25, further comprising prompting, by the ultrasonic medical device control module, the user to clean or re-sterilize a component of the reassembled ultrasonic medical device.

* * * * *